US005877019A

United States Patent [19]
Silverman et al.

[11] Patent Number: 5,877,019
[45] **Date of Patent: *Mar. 2, 1999**

[54] ANIMAL 2-5A-DEPENDENT RNASES AND ENCODING SEQUENCES THEREFOR

[75] Inventors: Robert H. Silverman, Shaker Heights; Bret A. Hassel, Chagrin Falls; Aimin Zhou, Solon, all of Ohio

[73] Assignee: Cleveland Clinic Foundation, Cleveland, Ohio

[ * ] Notice: The term of this patent shall not extend beyond the expiration date of Pat. No. 5,840,577.

[21] Appl. No.: 701,005

[22] Filed: Aug. 21, 1996

Related U.S. Application Data

[63] Continuation of Ser. No. 141,304, Oct. 22, 1993, abandoned, which is a continuation-in-part of Ser. No. 28,086, Mar. 8, 1993.

[51] Int. Cl.[6] ................................ C12N 5/16; C12N 9/22

[52] U.S. Cl. ........................... 435/348; 435/199; 435/325

[58] Field of Search ................................ 435/240.2, 325, 435/348, 199

[56] References Cited

U.S. PATENT DOCUMENTS

| | | | |
|---|---|---|---|
| 5,063,159 | 11/1991 | Revel et al. | 435/252.3 |
| 5,589,625 | 12/1996 | Saarma et al. | 800/205 |

FOREIGN PATENT DOCUMENTS

WO 93/19187 9/1993 WIPO .

OTHER PUBLICATIONS

Gura: Science, 270:575–577 (Oct. 27, 1995).
Nejidat et al.: Physiologia Plantarum, 80:662–668 (1990).
Gergerich et al.: Phytopathology, 78(3):270–272 (1988).
Cuozzo et al.: Bio/Technology, 6:549–557 (May 1988).
Jacobsen, H. et al.: Virology, 125:496–501 (1983).
Jacobsen, H. et al.: *Proc. Natl. Acad. Sci. USA*, 80:4954–4958 (Aug. 1983).
Silverman, R.H. et al.: *Local Organ. Comm. of 5th Ann. Meeting of Interf. Res.* (*The Biol. of Interf. Syst. 1988*), 183–186 (1989).
Ferbus, D. et al.: *Mol. & Cell. Biochem.*, 62:51–55 (1984).
Eppstein D.A. et al.: *J. Biol. Chem.*, 257(22):13390–13397 (1982).
Hovanessian, A.G. et al.: *J. Biol. Chem.*, 263(10):4945–4949 (1988).
Hovanessian, A.G. et al.: *EMBO J.*, 6(5):1273–1280 (1987).
Hearl, W.G. et al.: *J. Virol.* 61(5):1586–1592 (1987).
Wreschner, D.H. et al.: *Nature*, 289(5796):414–417 (Jan. 29, 1981).

(List continued on next page.)

*Primary Examiner*—Eric Grimes
*Attorney, Agent, or Firm*—Rothwell, Figg, Ernst & Kurz

[57] ABSTRACT

2-5A-dependent RNase, an endoribonuclease that requires 5'-phosphorylated 2',5'-linked oligoadenylates (2-5A), functions in the molecular mechanism of interferon action. Recombinant, 2-5A-dependent RNase was expressed to high levels (at least 10% of the soluble protein) in insect cells by infecting with baculovirus containing human cDNA to 2-5A-dependent RNase. In contrast, there was no 2-5A-dependent RNase present in control insect cells infected with nonrecombinant baculovirus. The purified, recombinant enzyme eluted from a gel-filtration column as a monomer that showed potent and highly specific, 2-5A-dependent RNase activity. Precise activitor requirements were determined using the purified enzyme of a variety of 2',5'-linked oligonucleotides. The activated enzyme was capable of cleaving both poly(rU) and, to a lesser extent, poly(rA) but not poly(rC), poly(rG), or poly(dT. Interestingly, poly(rU) was cleaved to a series of discrete products ranging between 5 and 22 nucleotides in length. Furthermore, whereas manganese and magnesium stimulated 2-5A-dependent RNase activity, the enzyme was capable of cleaving RNA in the absence of divalent cations.

16 Claims, 26 Drawing Sheets

OTHER PUBLICATIONS

Debois, M.F. et al.: *Ann. Inst. Pasteur/Virol.,* 1987.
Yang–Feng, T.L. et al.: *Genomics* 19:173–176 (1994).
Dong, B. et al.: *J. Biol. Chem.* 269(19):14153–14158 (May 3, 1994).
Hassel, H.A. et al.: *EMBO J.,* 12(8):3297–3304 (1993).
Zhou, A. et al.: *Cell,* 72:753–765 (Mar. 12, 1993).
William, B.R.G. et al.: *Local Org. Comm. of 5th Ann. Meet. of Interf. Res.* (*The Biol. of Interf Syst.*), 159–162 (1988).
Sawai, H. et al.: *J. Biol. Chem,* 288(3):1671–1677 (Feb. 10, 1983).
Torrence, P.F. et al.: *J. Biol. Chem.,* 263(3):1131–1139 (Jan. 25, 1988).
Lesiak, K. et al.: *J. Biol. Chem.* 258(21):13082–13088 (Nov.10, 1983).
Black, R.J. et al.: *FEBS Letters,* 191(1):154–158 (Oct. 1985).
Torrence, P.F. et al.: *Proc. Natl. Acad. Sci. USA,* 78(1):5993–5997 (Oct. 1981).
Lesiak, K. et al.: *J. Biol. Chem.,* 262(5):1961–1965 (Feb. 15, 1987).
Lesiak, K. et al.: *Bioconjugate Chem,* 467–472 (Nov./Dec., 1993).
SenGupta, D.N. et al.: *Proc. Natl. Acad. Sic. USA,* 87:7492–7496 (Oct. 1990).
Silverman, R.H.: *Anal. Biochem,* 144:450–460 (1985).
Krause, D. et al.: *J. Interf. Res.,* 13:13–16 (1993).
Krause, D. et al.: *J. Biol. Chem.*, 260(16):9501–9507 (Aug. 5, 1985).
Kraus, D. et al.:*J. Biol. Chem.*, 261(15):6836–6839 (May 25, 1986).
Maheshwari, R.K. et al.: *Science,* 219:1339–1341 (Mar. 18, 1983).
Silverman, R.H.:*Eur. J. Biochem.,* 126:333–341 (1982).
Ryseicki, G.: *J. Interf. Res.,* 9:649–657 (1989).
Wreshcner, D.H. et al: *Nucleic Acids Res.*, 9(7):1571–1581 (1981).
Cayley, P.J. et al.: *Cell Resp. to Mol. Modul.,* 347–360 (1982).
Torrence, P.F. et al.: *Proc. Natl. Acad. Sci. USA,* 90:1300–1304 (Feb. 1993).
Silverman, R.H. et al.: *Biol. of Interf. System,* 189–200 (1983).
Silverman, R.H. et al.: *J. Virology,* 46(3):1051–1055 (Jun. 1983).
Grimley, P.M. et al.: *Cancer Res.,* 144:3480–3488 (Aug. 1984).
SenGupta, D.N. et al.: *Nuclei Acids Res.,* 17(3):969–978 (1989).
Silverman, R.H.: *J. Interf. Res.,* 14:101–104 (1994).
Kerr, I.M.: *Phil. Trans. R. Soc. Lond.,* B299:59–67 (1982).
Meurs, E. et al.: *Ann. Inst. Pasteur/Virol.,* 137E:251–272 (1986).
Schmidt, A. et al.: *Nat. Immun. Cell Growth Regul.,* 6:19–27 (1987).
Dieffenbach, C.W. et al.: *J. Biol. Chem.,* 264(22):13281–13288 (1989).
Suhadolnik, R.J. et al.: *Biochem.,* 27:8846–8851 (1988).
Wells, A.J. et al.: *J. Biol. Chem.,* 259(2):1363–1370 (Jan. 25, 1984).
Reid, T.R. et al.: *Anal. Biochem.,* 136:136–141 (1984).
Hersh, C.L. et al.: *J. Biol. Chem.,* 259(3):1727–1730 (Feb. 10, 1984).
Iwata, A. et al.: *J. Biochem.* 104:247–250 (1988).
Shimizu, N. et al.: *J. Biochem,* 94:1421–1428 (1983).
Orlic, D. et al.: *Exp. Hematol.,* 13:821–826 (1985).
Orlic, D. et al.: *Blood Cells,* 10:193–210 (1984).
Lewis, J.A. et al.: *Viology,* 133:464–469 (1984).
Mengheri, E. et al.: *FEBS,* 157(2):301–305 (Jul. 1983).
Lewis, J.A. et al.: *Eur. J. Biochem.,* 86:497–509 (1978).
Lewis, J.A. et al.: *Proc. Natl. Acad. Sci. USA,* 80:26–30 (Jan. 1983).
Schattner, A. et al.: *J. Interf. Res.,* 1(4):587–594 (1981).
Weissenbach, J. et al.: *Proc. natl. Acad. Sci. USA,* (77)(12):7152–7156 (Dec. 1980).
Revel, M. et al.: *Texas Reports on Biology and Medicine,* 41:452–462 (1981–1982).
Revel, M.: "*Molecular Mechanisms Involved in the Intiviral Effects of Interferon,*" 101–163.
Revel, M et al.: *Cell Resp. Mol. Modul.,* 361–384 (1982).
Wallach, D. et al.: *Nature,* 287:68–90 (Sep. 1980).
Revel, M. et al.: *Ann. Rev. Biochem,* 47:1079–1126 (1978).
Chernajovsky, Y. et al.: *Eur. J. Biochem.,* 96:35–41 (1979).
Wallach, D. et al.: *Interferons,* 449–463 (1982).
Kimchi, A. et al.: *Proc. Natl. Acad. Sci. USA,* 76(7):3208–3212 (Jul. 1979).
Kimchi, A. et al.: *Anti–Mitogenic Func. of Interf.–Induced (2′–5′)Oligo(adenylate . . . ,* 5–10 (1980).
Zilberstein, A. et al.: *Proc. natl. Acad. Sci. USA,* 75(1):4734–4738 (Oct. 1978).
Kimchi, A. et al.: *FEBS,* 134(2):212–216 (Nov. 1981).
Chebath, J. et al.: *J. Biol. Chem.,* 262(8):3852–3857 (Mar. 15, 1987).
Rappoport, S. et al.: *FEBS,* 149(1):47–50 (Nov. 1982).
Panet, A. et al.: *Virology,* 114:567–572 (1981).
Epstein, D.A. et al.: *Eur. J. Biochem.,* 118:9–15 (1981).
Sen, G.C.: *Pharmac. Ther.,* 24:235–257 (1984).
Kumar, R. et al.: *J. Virol.,* 62(2):641–643 (Feb. 1988).
Salzberg, S. et al.: *Mol. Cell. Biol.,* 3(10):1759–1765 (Oct. 1983).
Panet, A.: *Mol. Cell. Biochem.,* 52:153–160 (1983).
Lewis, J.A.: *Virology,* 162:118–127 (1988).
Neth, R. et al.: Reprint from *Modern Trends in Human Leukemia III* (Springer–Verlag Berlin Heidelberg Ny 1979).
Kemchi, A. et al.: *Nature,* 282:20–27 (Dec. 1979).
Sen, G.C. et al.: *J. Biol. Chem.,* 253(17):5915–5921 (Sep. 10, 1978).
Shimizu, N. et al.: *J. Biol. Chem.,* 254(23):12034–12037 (Dec. 10, 1979).
Schmidt, A. et al.: *Proc. natl. Acad. Sci. USA,* 76(10):4788–4792 (Oct. 1979).
Revel, M. et al.: *Studies on Interef. Action: Synth., Degrad. & Biol. Act. of (2′–5′) Oligo–Isoadenylate,* Res. of Macromolecular Synth. by Low Mol. Weight Mediators, Academic Press, NY, pp. 341–359 (1979).
Lengyel, P. et al.: *J. Interf. Res.,* 7:511–519 (1987).
Floyd–Smith, G. et al.: *J. Interf. Res.,* 8:517–525 (1988).
Kerr, I.M. et al.: *Proc. Natl. Acad. Sci. USA,* 75(1):256–260 (Jan. 1978).
Salehzada, T. et al.: *J. Biol. Chem.,* 266(9):5808–5813 (Mar. 25, 1991).
Salehzada, T. et al.: *Anal. Biochem.,* 196:410–414 (1991).
Williams, B.R.G. et al.: *Nature,* 276:88–90 (Nov. 1978).
Roberts, W.K. et al.: *Proc. Natl. Acad. Sci. USA,* 73(9):3136–3140 (Sep. 1976).
Kerr, I.M. et al.: *Nature,* 268:537–542 (1977).
Salehzada, T. et al.: *J. Biol. Chem.,* 268(11):7733–7740 (Apr. 15, 1993).

Lengyel, P.: *Proc. Natl. Acad. Sci. USA,* 90:5893–5895 (Jul. 1993).
Cayley, P.J. et al.: *Piochem. Biophys. Res. Comm.,* 108(3):1243–1250 (Oct. 15, 1982).
Kerr, I.M. et al.: *Eur. J. Biochem.,* 69:551–561 (1976).
Kumar, R. et al.: *J. Virol.,* 62(9):3175–3181 (Sep. 1988).
Shaila, S. et al.: *gen. Virol.,* 37:535–546 (1977).
Brown, G.E. et al.: *Biochem. Biophys. Res. Commun.,* 69(1):114–122 (1976).
Sen, G.C. et al.: *Nature,* 264:370–373 (Nov. 25, 1976).
Hanks, S.K. et al.: *Science,* 241:42–52 (Jul. 1988).
Singh, H. et al.: *Cell,* 52:415–423 (Feb. 12, 1988).
Singh, H. et al.: *BioTech.,* 7(3):252–261 (1989).
Baglioni, C. et al.: *Nature,* 273:684–687 (Jun. 1978).
Apirion, D.: "Isolation, Genetic Mappern and Some Characterization of a Mutation in *Escherichia Coli . . . ,*" 659–671 (Dec. 1978).
Goldblum, K. et al.: *J. Bacteriology,* 146:128–132 (Apr. 1981).
Slattery, E. et al.: *Proc. natl. Acad. Sci. USA,* 76(10):4778–4782 (Oct. 1979).
Nilsen, T.W. et al.: *J. Biol. Chem.,* 256(21):10751–10754 (Nov. 10, 1981).
Williams, B.R.G. et al.: *FEBS,* 105(1):47–52 (Sep. 1979).
Floyd–Smith, G.: *J. Cell Biochem.,* 38:13–21 (1988).
Schmidt, A. et al.: *FEBS,* 95(2):257–264 (Nov. 1978).
Hoyanessian, A.G. et al.: *Eur. J. Biochem.,* 84:149–159 (1978).
Clemens, M.J. et al. *Cell,* 13:565–572 (Mar. 1978).
Sen, G.C. et al.: *J. Biol. Chem.,* 267(8):5017–5020 (Mar. 15, 1992).
Nilsen, T.W. et al.: *Proc. Natl. Acad. Sci. USA,* 76(6):2600–2604 (Jun. 1979).
Ratner, L. et al.: *Eur. J. Biochem,* 79:565–577 (1977).
Baglioni, C. et al.: *J. Biol. Chem.,* 255(18):8390–8393 (Sep. 25, 1980).
Williams, B.R.G. et al.: *Nature,* 282(5739):582–586 (Dec. 6, 1979).
Kerr I.M. et al.: "*The 2–5A (pppA2′ p5′A2′ p5′A) System in Interferon–treated and Control Cells*", Biochem. Soc. Trans. 9:54(P) (1981).
Floyd–Smith, G. et al.: *Science,* 212:1030–1032 (May 1981).
Ratner, L. et al.: *Biochem. Biophys. Res. Commun.,* 81(3):947–954 (Apr. 14, 1978).
Coccia, E.M. et al.: *Virology,* 179:228–233 (1990).
Berg, J.M.: *J. Biol. Chem.,* 265(12):6513–6516 (Apr. 25, 1990).
Evans, R.M. et al.: *Cell,* 52:1–3 (Jan. 15, 1988).
Belasco, J. et al.: *Gene,* 72:15–23 (1988).
Fry, D.C. et al.: *Proc. Natl. Acad. Sci. USA,* 83:907–911 (Feb. 1986).
Walker, J.E. et al.: *EMBO,* 1(8):945–951 (1982).
Krupinski, J. et al.: *Science,* 244:1558–1564 (1989).
Au, D.C. et al.: *Biochem.,* 28:2772–2776 (1989).
Glaser, P. et al.: *EMBO,* 8(3):967–972 (1989).
Imai, J. et al.: *J. Biol. Chem.,* 260(3):1390–1393 (Feb. 10, 1985).
Watling, D. et al.: *EMBO,* 4(2):431–436 (1985).
Pestka, S. et al.: *Ann. Rev. Biochem.,* 56:727–777 (1987).
Lengyel, P.: *Ann. Rev. Biochem.,* 51:251–282 (1982).
Night, M. et al.: *Nature,* 288(5787):189–192 (Nov. 13, 1980).
Deutscher, M.P. et al.: *J. Biol. Chem.,* 268(18):13011–13014 (Jun. 25, 1993).
Cedergren, R. et al.: *FEBS,* 226(1)63–66 (Dec. 1987).
Floyd–Smith, G. et al.: *Meth. Enzymology,* 119:489–499 (1986).
Farrell, P.J. et al.: *Proc. Natl. Acad. Sci. USA,* 75(12):5893–5897 (Dec. 1978).
Bisbal, C. et al.: *Eur. J. Biochem.,* 179:595–602 (1989).
Brawerman, G.: *Cell,* 57:9–10 (Apr. 7, 1989).
Mackie, G.A.: *J. Bacteriology,* 178(8)2488–2497 (Apr. 1991).
Xia, Z. et al.: *J. Biol. Chem.,* 265(12):6517–6520 (Apr. 25, 1990).
Deutscher, M.P. et al.: *Cell,* 40:731–732 (Apr. 1985).
Cormack, R.S. et al.: *Proc. natl. Acad. Sci. USA,* 90:9006–9010 (Oct. 1993).
Bouvet, P. et al.: *Nature,* 360:488–491 (Dec. 3, 1992).
Claverie–Martin, F. et al.: *J. Biol. Chem.,* 266(5):2843–2851 (Feb. 15, 1991).
Mudd, E.A. et al.: *EMBO,* 7(11):3601–3607 (1988).
Ehretsmann, C.P. et al.: *Genes & Develop.,* 6:149–159 (1992).
Taraseviciene, L. et al.: *Mol. Microbiol.,* 5(4):851–855 (1991).
Chauhan, A.K. et al.: *Nucleic Acids Res.,* 19(1):125–129 (1991).
Babitzke, P. et al.: *Proc. Natl. Acad. Sci. USA,* 88:1–5 (Jan. 1991).
Mudd, E.A. et al.: *Mol. Microbiol.,* 4(12):2127–2135 (1990).
Silverman, R.H. et al.: *Eur. J. Biochem.,* 124:131–138 (1982).
Hovanessian, A.G. et al.: *Meth. Enzymol.,* 79:184–199 (1981).
Goswami, B.B. et al.: *J. Biol. Chem.,* 259(3):1371–1374 (Feb. 10, 1984).
Sharma, O.K. et al.: *Proc. Natl. Acad. Sci. USA,* 78(4):2221–2224 (Apr. 1981).
Goswami, B.B. et al.: *J. Biol. Chem.,* 257(12):6867–6870 (Jun. 25, 1982).
Sharma, O.K. et al.: *FEBS 0601,* 158(2):298–300 (Jul. 1983).
Sen, G.C. et al.: *J. Virology,* 45(3):1017–1027 (Mar. 1983).
Sen, G.C. et al.: *J. gen Virol.,* 64:2213–2220 (1983).
Sawai, H. et al.: *J. Biochem.,* 101:339–346 (1987).
Taira, H. et al.: *J. Interf. Res.,* 5:583–596 (1985).
Salzberg, S. et al.: *Mol. Cell. Biol.,* 3(10):1759–1765 (Oct. 1983).
David, S. et al.: *J. Virology,* 63(3):1116–1122 (Mar. 1989).
.Affabris, E. et al.: *Virology,* 125:508–512 (1983).
Mechti, N. et al.: *J. Biol. Chem.,* 259(5):3261–3265 (Mar. 10, 1984).
Miyamoto, N.G. et al.: *Virology,* 107:461–475 (1980).
Miyamoto, N.G. et al.: *J. Biol. Chem.,* 258(24):15232–15237 (Dec. 25, 1983).
Eppstein, D.A. et al.: *Virology,* 98:9–19 (1979).
Benech, P. et al.: *Mol. Cell. Biol.,* 7(12):4498–4504 (Dec. 1987).
Cohen, B. et al.: *EMBO,* 7(5):1411–1419 (1988).
Mory, Y. et al.: *J. Interf. Res.,* 9:295–304 (1989).
Imai, J. et al.: *J. Biol. Chem.,* 257(21):12739–12745 (Nov. 10, 1982).
Krause, D. et al.: *Eur. J. Biochem.,* 146:611–618 (1985).
Silverman, R.H. et al.: *Eur. J. Biochem.,* 115:79–85 (1981).
Wreschner, D.H. et al.: *Eur. J. Biochem.,* 172:333–340 (1988).

Penn, L.J.Z. et al.: *J. Virology,* 49(3):748–753 (Mar. 1984).
Saunders, M.E. et al.: *EMBO,* 4(7):1761–1768 (1985).
Lesiak, K. et al.: *Biochem. Biophys. Res. Commun.,* 126(2):917–921 (Jan. 31, 1985).
Kitade, Y. et al.: *Nucl. Acids Res.,* 19(15):4103–4108 (1991).
Torrence, P.F. et al.: *FEB 04463,* 212(2):267–270 (Feb. 1987).
Alster, D. et al.: *Biochem. Biophys. Res. Commun.,* 141(2):555–561 (Dec. 15, 1986).
Lesiak, K. et al.: *J. Med. Chem.,* 1015–1022 (Jun. 1986).
Torrence, P.F. et al.: *FEB 04463*, 212(2):267–270 (Feb. 1987).
Ilson, D.H. et al.: *J. Interf. Res.,* 6:05–12 (1986).
Jamoulle, J.C. et al.: *Biochem.,* 23:3063–3069 (1984).
Imai, J. et al.: *Biochem.,* 23:766–774 (1984).
Eppstein, D.A. et al.: *J. Biol. Chem.,* 260(6):3666–3671 (Mar. 25, 1985).
Johnston, M.I. et al.: *Biochem. Biophys. Res. Commun.,* 97(2):375–383 (Nov. 28, 1980).
Torrence, P.F. et al.: *J. Med. Chem.,* 27:726–733 (1984).
Imai, J. et al.: *Org. Chem.,* 1418–1420 (May 3, 1985).
Silverman, R.H. et al.: *The Biology of the Interferon System 1984,* Kirchner et al., eds. 1985 Elsevier Science Publishers B.V., pp. 141–145.
Silverman, R. et al.: In, *Interferons as cell growth inhibitors & antitumor factors.* (Friedman et al, eds.) A.R. Liss, NY, NY pp. 143–150 (1986).
Williams BRG, (1983). *The Biochemical action of interferon. In: Interferon and Cancer,* K Sikors ed, Elsevier, Amsterdam, pp. 33–52.
Doetsch, P.W. et al.: *Proc. Natl. Acad. Sci. USA,* 78:1–9 (1981).
Henderson, E.E. et al.: *Virology,* 122:198–201 (1982).
Wu, J.M. et al.: *Biochem. & Biophys. Res. Comm.,* 86(3):648–653 (1979).
Lee, C. et al.: *FEBS.* 157(1):205–209 (Jun. 1983).
Doetsch, P. et al.: *Nature*, 291:355–358 (May 1981).
Suhadolnik, R.J. et al.: *Biochemistry,* 22:4153–4158 (1983).
Kariko, K. et al.: *Biochemistry,* 26:7127–7135 (1987).
Kariko, K. et al.: *Biochemistry,* 26:7136–7142 (1987).
Suhadolnik, R.J. et al.: *Biochemistry,* 26:7143–7149 (1987).
Suhadolnik, R.J. et al.: *Biochemistry,* 27:8840–8846 (1988).
Suhadolnik, R.J. et al.: *Biochem. & Biophys. Res. Comm.,* 111(1):205–212 (1983).
Black, P.L. et al.: *J. Immun.,* 135(5):2773–2777 (Nov. 1984).
Lee, C. et al.: *Biochemistry,* 24(3):551–555 (Jan. 1985).
Knight, M. et al.: *Meth. Enzymology,* 79:217–227 (1981).
Williams, B.R.G. et al.: *Meth. Enzymology,* 79:199–208 (1981).
Kerr, I.M. et al.: *Adv. Cyclic Nucleo. Res.,* 14:469–478 (1981).
Gribaudo, G. et al.: *J. Virol.,* 65(4):1478–1757 (Apr. 1991).
Suhadolnik, R.J. et al.: *Biochemistry,* 22(?):4153–4157 (1983).
Justesen, J. et al.: *Proc. Natl. Acad. Sci. USA,* 77:4618–4622 (1980).
Ono, M. et al.: *J. Mol. Biol.,* 129:343–357 (1979).
LeBleu, B. et al.: *Mechanisms of Interferon Action: Biochem. & Genetic Appr.,* Interferon 4: 47–94 (1982).
Pai, E.F. et al.: *Nature,* 341:209–214 (Sep. 1989).
St. Laurent, G. et al.: *Cell,* 95–102 (1983).
Saraste, M. et al.: *TIBS,* 15:430–434 (Nov. 1990).
Rozen, F. et al.: *Mol. & Cell. Biol.,* 9(9):4061–4063 (Sep. 1989).
Schroder, H.C. et al.: *FASEB J.,* 4:3124–3130 (Oct. 1990).
Suhadolnik, R.J. et al.: *Nucleosides, Nucleotides, and their Biol. Appl.,* pp. 147–179 (Academic Press 1983).
Torrence, P.F. et al.: *Proc. Natl. Acad. Sci. USA,* 78(10):5993–5997 (Oct. 1981).
Torrence, P.F. et al.: *FEBS,* 130(2): 291–296 (Aug. 1981).
Imai, J. et al.: *J. Biol. Chem.,* 257(21):12739–12745 (Nov. 1982).
Morag, A. et al.: *Lancet,* p. 744 (Mar. 27, 1982).
Shulman, L. et al.: *Nature,* 288:98–100 (Nov. 1980).
Lesiak, K. et al.: *FEBS,* 151(2):291–296 (Jan. 1983).
de Clercq, E. et al.: *IUPHAR 9th Int'l Congress of Pharma.,* London, 1984, Paton et al. eds. (vol. 1), pp. 307–317.
Williams, B.R.G. et al.: *Biol. of Interf. Syst.,* 1981 Elsevier, De Mayer et al. eds., pp. 111–114.
Silverman, R.H. et al.: In *Lymphokines & Interf.: A Practical Approach,* Clemens et al. eds., IRL Press, Wash. D.C. 1987, pp. 149–193.
Justesen, J. et al.: *Nucleic Acids Res.,* 8(14):3073–3085 (1980).
Torrence, P.F. et al.: *Chemica Scripta,* 26:191–197 (1986).
Torrence, P.F. et al.: *Molec. Aspects Med.,* 5:129–171 (1982).
Chousterman, S. et al.: *J. Biol. Chem.,* 262(10):4806–4811 (Apr. 1987).
Chelbi–Alix, M.K. et al.: *J. Biol. Chem.,* 260(13):7960–7964 (Jul. 1985).
Besancon, F. et al.: *Biochem. Biophys. Res. Comm.,* 103(1):16–24 (Nov. 1981).
Lab, M. et al.: *Biochem. & Biophys. Res. Comm.,* 105(2):412–418 (Mar. 1982).
Dougherty, J.P. et al.: *J. Biol. Chem.,* 255(9):3813–3816 (May 1980).
Mory, Y. et al.: *J. Interf. Res.,* 9:295–304 (1989).
Ghosh, S.K. et al.: *J. Biol. Chem.,* 266(23):15293–15299 (Aug. 1991).
Minks, M.A. et al.: *J. Biol. Chem.,* 254(20):10180–10183 (Oct. 1979).
Wu, J.M. et al.: *AIDS Res.,* 2(2):127–131 (1986).
Schroder, H.C. et al.: *J. Biol. Chem.,* 264(10):5669–5673 (Apr. 1989).
Schroder, H.C. et al.: *AIDS Res. & Human Retrov.,* 6(5):659–672 (1990).
Schroder, H.C. et al.: *Biol. Chem. Hoope–Seyler,* 369:985–995 (Sep. 1988).
Agy, M.B. et al.: *Virology,* 177:251–258 (1990).
Suhadolnik, R.J. et al.: *Photoaffinity,* 27(24):8840–8846 (1988).
Read, S.E. et al.: *J. Interf. Dis.,* 152(3):466–472 (Sep. 1985).
Ghora, B.K. et al.: *Cell,* 15:1055–1066 (Nov. 1978).
Samanta, H. et al.: *J. Biol. Chem.,* 255(20)9807–9813 (Oct. 1980).
Broeze, R.J. et al.: *J. Interf. Res.,* 1(2):191–201 (1981).
Yang, K. et al.: *J. Biol. Chem.,* 256(17):9324–9328 (Sep. 1981).
Cayley, P.J. et al.: *Eur. J. Biochem.,* 143:165–174 (1984).
Brown, R.E. et al.: *Meth. in Enzymology,* 79:208–216 (1981).
Hersh, C.L. et al.: *J. Biol. Chem.,* 259(3):1731–1737 (Feb. 1984).
Rice, A.P. et al.: *J. Virol.,* 50(1):220–228 (Apr. 1984).
Rice, A.P. et al.: *J. Virol.,* 56(3):1041–1044 (Dec. 1985).
Williams, B.R.G. et al.: *Eur. J. Biochem.,* 92:455–462 (1978).
Cayley, P.J. et al.: *Eur. J. Biochem.,* 122:601–608 (1982).
Reid, T.R. et al.: *Anal. Biochem.,* 136:136–141 (1984).

Williams, B.R.G. et al.: *Nucleic Acids Res.,* 6(4):1335–1350 (Apr. 1979).
Foster, G.R. et al.: *Proc. natl. Acad. Sci. USA,* 88:2888–2892 (Apr. 1991).
Cayley, P.J. et al.: *Interferons,* pp. 143–157 (Academic Press 1992).
Lebleu, B. et al.: *Proc. Natl. Acad. Sci. USA,* 73(9):3107–3111 (Sep. 1976).
Bisbal, C. et al.: *Biochemistry,* 26:5172–5178 (1987).
Mechti, N. et al.: *Differentiation,* 29:136–139 (1985).
Bayard, B. et al.: *Biochemistry,* 25:3730–3736 (1986).
Stark, G.R. et al.: *Nature,* 278:471–473 (Mar. 1979).
Hovanessian, A.G. et al.: *Proc. Natl. Acad. Sci. USA,* 76(&):3261–3265 (Jul. 1979).
Buffet–Janvrease, C. et al.: *J. Interf. Res.,* 6:85–96 (1986).
Ogunkolade, W. et al.: *J. Interf. Res.,* 7:245–254 (1987).
Riviere, Y. et al.: *Ann. Immunol.* (*Inst. Pasteur*), 135(C):333–343 (1984).
Marcovistz, R. et al.: *J. gen. Virol.,* 65:995–997 (1984).
Hovanessian, A.G. et al.: *Virology,* 104:195–204 (1980).
Laurence, L. et al.: *Virology,* 143:290–299 (1985).
Chapekar, M.S. et al.: *Biochem & Biophys. Res. Commun.,* 151(3):1180–1187 (Mar. 1988).
Floyd–Smith, G. et al.: *Proc. of Soc. for Exper. Bio. & Medicine,* 189:329–337 (1988).
Esteban, M. et al.: *J. gen. Virol.,* 67:801–808 (1986).
Paez, E. et al.: *J. Virol.,* 56(1):75–84 (Oct. 1985).
Paez, E. et al.: *Virology,* 134:12–28 (1984).
Paez, E. et al.: *Virology* 134:29–39 (1984).
Esteban, M. et al.: *Virology,* 134:40–51 (1984).
Santoro, M.G. et al.: *Biochem. & Biophys. Res. Commun.,* 116(2):442–448 (Oct. 1983).
Benavente, J. et al.: *J. Virol.,* 51(3):866–871 (Sep. 1984).
Eppstein, D.A. et al.: *Nature,* 302:723–724 (Apr. 1983).
Eppstein, D.A. et al., *Virology,* 131:341–354 (1983).
Eppstein, D.A. et al.: *J. Interf. Res.,* 3(3):305–311 (1983).
Eppstien, D.A. et al.: *J. Biol. Chem.,* 261(13):5999–6003 (May 1986).
Drocourt, J. et al.: *Nucleic Acids Res.*, 10(6):2163–2174 (1982).
Rice, A.P. et al.: *J. Virol.,* 54(3):894–898 (Jun. 1985).
Jamoulle, J.–C. et al.: *Biochemistry,* 26:376–383 (1987).
Torrence, P.F. et al.: *Anaylt. Biochem.,* 129:103–110 (1983).
Johnston, M.I. et al.: *J. Biol. Chem.,* 262(17):8377–8382 (Jun. 1987).
Mittnacht, S. et al.: *J. gen. Virol.,* 68:2945–2951 (1987).
Defilippi, P. et al.: *FEBS 3525,* 198(2):326–332 (Mar. 1986).
Ankel, H. et al.: *J. gen. Virol.,* 66:2355–2364 (1985).
Hovanessian, A.G.: *J. Interf. Res.,* 11:199–205 (1991).
Marie, L. et al.: *J. Biol. Chem.,* 267(14):9933–9939 (1992).
Hovanessian, A.G. et al.: *Virology,* 101:81–90 (1980).
Flenniken, A.M. et al.: *J. Virol.,* 62(9):3077–3083 (Sep. 1988).
Wood, J.N. et al.: *Nature,* 282:74–76 (Nov. 1979).
Hovanessian, A.G. et al.: *J. Interf. Res.,* 1(2):179–190 (1981).
Hovanessian, A.G. et al.: *Proc. Natl. Acad. Sci. USA,* 76(7):3261–3265 (Jul. 1979).
Galabru, J. et al.: *J. gen. Virol.,* 66:711–718 (1985).
Buffet–Janvresse, C. et al.: *Proc. of Soc. for Exp. Biol. & Medicine,* 175:169–175 (1984).
Knight, Jr., E. et al.: *Proc. Natl. Acad. Sci. USA,* 82:1151–1154 (Feb. 1985).
Kimchi, A.: *J. Interf. Res.,* 1(4):559–569 (1981).
Cleveland, D.W. et al.: *J. Biol. Chem.,* 252(3):1102–1106 (Feb. 1977).
Bayard, B. et al.: *Eur. J. Biochem.,* 142:291–298 (1984).
Bisbal, C. et al.: *Biochemistry,* 26:5172–5178 (1987).
Bayard, B. et al.: *Eur. J. Biochem.,* 151:319–325 (1985).
Bayard, B. et al.: *Biochemistry,* 25:3730–3736 (1986).
Baglioni, C. et al.: *Biochemistry,* 18(9):1765–1770 (1979).
Nilsen, T.W. et al.: *J. Virol.,* 42(3):1039–1045 (Jun. 1982).
Baglioni, C. et al.: *J. Biol. Chem.,* 256(7):3253–3257 (Apr. 1981).
Nilsen, T.W. et al.: *Biochemsitry,* 19:5574–5579 (1980).
Baglioni, C. et al.: *Biochemistry,* 20:758–762 (1981).
Nilsen, T.W. et al.: *Virology,* 122:498–502 (1982).
Nilsen, T.W. et al.: *Molecular & Cellular Biol.,* 3(1):64–69 (Jan. 1983).
Baglioni, C. et al.: *Cell,* 17:255–264 (Jun. 1979).
Nilsen, T.W. et al.: *Molecular & Cellular Biol.,* 2(2):154–160 (Feb. 1982).
Baglioni, C. et al.: *J. Virol.,* 52(3):865–871 (Dec. 1984).
Williams, G.J. et al.: *Virology,* 151:233–242 (1986).
Minks, M.A. et al.: *Nucleic Acids Res.,* 6(2):767–780 (Feb. 1979).
Baglioni, C.: Chapter 8, *The Molecular Mediators of Interferon Action,* pp. 153–168 (1982).
Nilsen, T.W. et al.: *J. Biol. Chem.,* 256(15):7806–7811 (Aug. 1981).
Nilsen, T.W. et al.: *J. Biol. Chem.,* 257(4):1602–1605 (Feb. 1982).
Verhaegen, M. et al.: *Proc. Natl. Acad. Sci. USA,* 77(8):4479–4483 (Aug. 1980).
Verhaegen–Lewalle, M. et al.: *Eur. J. Biochem.,* 126:639–643 (1982).
Vandenbussche, P. et al.: *Virology,* 111:11–22 (1981).
Chebath, J. et al.: *Nature,* 330:587–588 (Dec. 1987).
Chebath, J. et al.: *J. Biol. Chem.,* 262(8):3852–3857 (1987).
Sperling, J. et al.: *Proc. Natl. Acad. Sci. USA,* 88:10377–10381 (Dec. 1991).
Alarcon, B. et al.: *J. Virol.,* 52(1):183–187 (Oct. 1984).
Cailla, H. et al.: *Radiommunoassay and Related Procedures in Medicine 1982,* Int'l Atomic Energy Agency Vienna, 1982.
Cailla, H. et al.: *Proc. Natl. Acad. Sci. USA,* 79:4742–4746 (Aug. 1982).
Marti, J. et al.: *Nucleosides & Nucleotides*, 7(4):479–495 (1988).
Trujillo, M.A. et al.: *Eur. J. Biochem.,* 169:167–173 (1987).
Laurence, L. et al.: *Proc. Natl. Acad. Sci. USA*, 81:2322–2326 (Apr. 1984).
Hovanessian, A.G. et al.: *Eur. J. Biochem.,* 93:515–526 (1979).
Kerr, I.M. et al.: *The Biology of the Interferon System 1983,* Elsevier: De Maeyer et al. eds., pp. 213–222.
Etienne–Smekens, M. et al.: *FEBS L.,* 125(2):146–150 (Mar. 1981).
Smekens–Etienne, M. et al.: *Eur. J. Biochem.,* 130:269–273 (1983).
Wathelet, M. et al.: *FEBS L.,* 196(1):113–120 (Feb. 1986).
Verhaegen–Lewalle, M. et al.: *Virol.,* 117:425–434 (1982).
Haugh, M.C. et al.: *Eur. J. Biochem.,* 132:77–84 (1983).
Martin, E.M. et al.: *Eur. J. Biochem.,* 95:295–307 (1979).
Squire, J. et al.: *Genomics,* 19:174–175 (1994).
Fujihara, M. et al.: *J. Interf. Res.,* 9:691–707 (1989).
Hassel, B.A. et al.: *EMBO,* 12(8):3297–3304 (1993).
Nilsen, T.W. et al.: *Nature,* 286:178–181 (Jul. 1980).
Krishnan, I. et al.: *Nature,* 285:485–488 (Jun. 1980).

Krishnan, I. et al.: *Mol. & Cell. Biol.,* 1(10):932–938 (Oct. 1981).
Krishnan, I. et al.: *Proc. Natl. Acad. Sci. USA,* 77(11):6506–6510 (Nov. 1980).
Krishnan, I. et al.: *Virology,* 111:666–670 (1981).
Minks, M.A. et al.: *J. Biol. Chem.,* 254(12):5058–5064 (Jun. 1979).
Minks, M.A. et al.: *J. Biol. Chem.,* 255(13):6403–6407 (Jul. 1980).
West, D.K. et al.: *Mol. & Cell. Biol.,* 2(11):1436–1443 (Nov. 1982).
Ball, L.A.: *Virology,* 94:282–296 (1979).
Ball, L.A. et al.: *Proc. Natl. Acad. Sci. USA,* 75(3):1167–1171 (Mar. 1978).
Creasey, A.A. et al.: *Molecular and Cellular Biology,* (1983) pp. 1–28.
Eds. Williams, B.R.G. and Silverman, R.H.: *The 2–5A System,* Proc. of 6th Int'l Symp. of Res. Inst. Hosp. for Sick Children, Toronto, Ontario, Canada, Jun. 3–5, 1985.
Hassel, et al.: *J. Interferon Res.,* 12(Suppl. 1):S42 (1992).
Zhou, et al.: *J. Interferon Res.,* 12(Suppl. 1):S57 (1992).
Young et al., Science 222:778–782 (1983).
Gerald et al., Biochem. Biophys. Acta 866:1–14 (1986).
Nolan–Sorden et al., Anal. Biochem. 184:298–304 (1990).
Wreschner et al., Eur. J. Biochem. 124:261–268 (1982).
Murhammer et al., Appl. Biochem. Biotechnol. 31:283–310 (1991).
Silverman et al., J. Cellular Biochem., Supplement 16B, p. 163, Abstract G520 (1992).
Hassel et al., J. Cellular Biochem., Supplement 17C, p. 177, Abstract K405 (1993).
Luckow et al., Biotechnology 6:47–55 (1988).
Silverman et al., J. Biol. Chem. 263:7336–7341 (1988).
Seidah et al., DNA Cell Biol. 11:283–289 (1992).
Webster's II New Riverside Univ. Dictionary, Riverside Publishing Co., 1988, p. 1068.
U.S. application No. 07/914674, Silverman et al.

FIG. 3B1

```
                                          -103 aatcccaacttacactcaaagctt
ctttgattaagtgctaggagataaatttgcattttctcaaggaaaaggctaaaagtggtagcaggtggcatttaccgtc

ATG GAG AGC AGG GAT CAT AAC AAC CCC CAG GAG GGA CCC ACG TCC TCC AGC GGT AGA AGG    60
Met Glu Ser Arg Asp His Asn Asn Pro Gln Glu Gly Pro Thr Ser Ser Ser Gly Arg Arg    20

GCT GCA GTG GAA GAC AAT CAC TTG CTG ATT AAA GCT GTT CAA AAC GAA GAT GTT GAC CTG   120
Ala Ala Val Glu Asp Asn His Leu Leu Ile Lys Ala Val Gln Asn Glu Asp Val Asp Leu    40

GTC CAG CAA TTG CTG GAA GGT GGA GCC AAT GTT AAT TTC CAG GAA GAG GAA GGG GGC TGG   180
Val Gln Gln Leu Leu Glu Gly Gly Ala Asn Val Asn Phe Gln Glu Glu Glu Gly Gly Trp    60

ACA CCT CTG CAT AAC GCA GTA CAA ATG AGC AGG GAG GAC ATT GTG GAA CTT CTG CTT CGT   240
Thr Pro Leu His Asn Ala Val Gln Met Ser Arg Glu Asp Ile Val Glu Leu Leu Leu Arg    80

CAT GGT GCT GAC CCT GTT CTG AGG AAG AAG AAT GGG GCC ACG CTT TTT ATC CTC GCA GCG   300
His Gly Ala Asp Pro Val Leu Arg Lys Lys Asn Gly Ala Thr Leu Phe Ile Leu Ala Ala   100

ATT GCG GGG AGC GTG AAG CTG CTG AAA CTT TTC CTT TCT AAA GGA GCA GAT GTC AAT GAG   360
Ile Ala Gly Ser Val Lys Leu Leu Lys Leu Phe Leu Ser Lys Gly Ala Asp Val Asn Glu   120

TGT GAT TTT TAT GGC TTC ACA GCC TTC ATG GAA GCC GCT GTG TAT GGT AAG GTC AAA GCC   420
Cys Asp Phe Tyr Gly Phe Thr Ala Phe Met Glu Ala Ala Val Tyr Gly Lys Val Lys Ala   140

CTA AAA TTC CTT TAT AAG AGA GGA GCA AAT GTG AAT TTG AGG CGA AAG ACA AAG GAG GAT   480
Leu Lys Phe Leu Tyr Lys Arg Gly Ala Asn Val Asn Leu Arg Arg Lys Thr Lys Glu Asp   160

CAA GAG CGG CTG AGG AAA GGA GGG GCC ACA GCT CTC ATG GAC GCT GCT GAA AAA GGA CAC   540
Gln Glu Arg Leu Arg Lys Gly Gly Ala Thr Ala Leu Met Asp Ala Ala Glu Lys Gly His   180

GTA GAG GTC TTG AAG ATT CTC CTT GAT GAG ATG GGG GCA GAT GTA AAC GCC TGT GAC AAT   600
Val Glu Val Leu Lys Ile Leu Leu Asp Glu Met Gly Ala Asp Val Asn Ala Cys Asp Asn   200
```

FIG. 3B2

```
ATG GGC AGA AAT GCC TTG ATC CAT GCT CTC CTG AGC TCT GAC GAT AGT GAT GTG GAG GCT   660
Met Gly Arg Asn Ala Leu Ile His Ala Leu Leu Ser Ser Asp Asp Ser Asp Val Glu Ala   220

ATT ACG CAT CTG CTG CTG GAC CAT GGG GCT GAT GTC AAT GTG AGG GGA GAA AGA GGG AAG   720
Ile Thr His Leu Leu Leu Asp His Gly Ala Asp Val Asn Val Arg Gly Glu Arg Gly Lys   240

ACT CCC CTG ATC CTG GCA GTG GAG AAG AAG CAC TTG GGT TTG GTG CAG AGG CTT CTG GAG   780
Thr Pro Leu Ile Leu Ala Val Glu Lys Lys His Leu Gly Leu Val Gln Arg Leu Leu Glu   260

CAA GAG CAC ATA GAG ATT AAT GAC ACA GAC AGT GAT GGC AAA ACA GCA CTG CTG CTT GCT   840
Gln Glu His Ile Glu Ile Asn Asp Thr Asp Ser Asp Gly Lys Thr Ala Leu Leu Leu Ala   280

GTT GAA CTC AAA CTG AAG AAA ATC GCC GAG TTG CTG TGC AAA CGT GGA GCC AGT ACA GAT   900
Val Glu Leu Lys Leu Lys Lys Ile Ala Glu Leu Leu Cys Lys Arg Gly Ala Ser Thr Asp   300

TGT GGG GAT CTT GTT ATG ACA GCG AGG CGG AAT TAT GAC CAT TCC CTT GTG AAG GTT CTT   960
Cys Gly Asp Leu Val Met Thr Ala Arg Arg Asn Tyr Asp His Ser Leu Val Lys Val Leu   320

CTC TCT CAT GGA GCC AAA GAA GAT TTT CAC CCT CCT GCT GAA GAC TGG AAG CCT CAG AGC  1020
Leu Ser His Gly Ala Lys Glu Asp Phe His Pro Pro Ala Glu Asp Trp Lys Pro Gln Ser   340

TCA CAC TGG GGG GCA GCC CTG AAG GAT CTC CAC AGA ATA TAC CGC CCT ATG ATT GGC AAA  1080
Ser His Trp Gly Ala Ala Leu Lys Asp Leu His Arg Ile Tyr Arg Pro Met Ile Gly Lys   360

CTC AAG TTC TTT ATT GAT GAA AAA TAC AAA ATT GCT GAT ACT TCA GAA GGA GGC ATC TAC  1140
Leu Lys Phe Phe Ile Asp Glu Lys Tyr Lys Ile Ala Asp Thr Ser Glu Gly Gly Ile Tyr   380

CTG GGG TTC TAT GAG AAG CAA GAA GTA GCT GTG AAG ACG TTC TGT GAG GGC AGC CCA CGT  1200
Leu Gly Phe Tyr Glu Lys Gln Glu Val Ala Val Lys Thr Phe Cys Glu Gly Ser Pro Arg   400

GCA CAG CGG GAA GTC TCT TGT CTG CAA AGC AGC CGA GAG AAC AGT CAC TTG GTG ACA TTC  1260
Ala Gln Arg Glu Val Ser Cys Leu Gln Ser Ser Arg Glu Asn Ser His Leu Val Thr Phe   420
```

```
TAT GGG AGT GAG AGC CAC AGG GGC CAC TTG TTT GTG TGT GTC ACC CTC TGT GAG CAG ACT  1320
Tyr Gly Ser Glu Ser His Arg Gly His Leu Phe Val Cys Val Thr Leu Cys Glu Gln Thr   440

CTG GAA GCG TGT TTG GAT GTG CAC AGA GGG GAA GAT GTG GAA AAT GAG GAA GAT GAA TTT  1380
Leu Glu Ala Cys Leu Asp Val His Arg Gly Glu Asp Val Glu Asn Glu Glu Asp Glu Phe   460

GCC CGA AAT GTC CTG TCA TCT ATA TTT AAG GCT GTT CAA GAA CTA CAC TTG TCC TGT GGA  1440
Ala Arg Asn Val Leu Ser Ser Ile Phe Lys Ala Val Gln Glu Leu His Leu Ser Cys Gly   480

TAC ACC CAC CAG GAT CTG CAA CCA CAA AAC ATC TTA ATA GAT TCT AAG AAA CGT GCT CAC  1500
Tyr Thr His Gln Asp Leu Gln Pro Gln Asn Ile Leu Ile Asp Ser Lys Lys Arg Ala His   500

CTG GCA GAT TTT GAT AAG AGC ATC AAG TGG GCT GGA GAT CCA CAG GAA GTC AAG AGA GAT  1560
Leu Ala Asp Phe Asp Lys Ser Ile Lys Trp Ala Gly Asp Pro Gln Glu Val Lys Arg Asp   520

CTA GAG GAC CTT GGA CGG CTG GTC CTC TAT GTG GTA AAG AAG GGA AGC ATC TCA TTT GAG  1620
Leu Glu Asp Leu Gly Arg Leu Val Leu Tyr Val Val Lys Lys Gly Ser Ile Ser Phe Glu   540

GAT CTG AAA GCT CAA AGT AAT GAA GAG GTG GTT CAA CTT TCT CCA GAT GAG GAA ACT AAG  1680
Asp Leu Lys Ala Gln Ser Asn Glu Glu Val Val Gln Leu Ser Pro Asp Glu Glu Thr Lys   560

GAC CTC ATT CAT CGT CTC TTC CAT CCT GGG GAA CAT GTG AGG GAC TGT CTG AGT GAC CTG  1740
Asp Leu Ile His Arg Leu Phe His Pro Gly Glu His Val Arg Asp Cys Leu Ser Asp Leu   580

CTG GGT CAT CCC TTC TTT TGG ACT TGG GAG AGC CGC TAT AGG ACG CTT CGG AAT GTG GGA  1800
Leu Gly His Pro Phe Phe Trp Thr Trp Glu Ser Arg Tyr Arg Thr Leu Arg Asn Val Gly   600

AAT GAA TCC GAC ATC AAA ACA CGA AAA TCT GAA AGT GAG ATC CTC AGA CTA CTG CAA CCT  1860
Asn Glu Ser Asp Ile Lys Thr Arg Lys Ser Glu Ser Glu Ile Leu Arg Leu Leu Gln Pro   620

GGG CCT TCT GAA CAT TCC AAA AGT TTT GAC AAG TGG ACG ACT AAG ATT AAT GAA TGT GTT  1920
Gly Pro Ser Glu His Ser Lys Ser Phe Asp Lys Trp Thr Thr Lys Ile Asn Glu Cys Val   640
```

FIG. 3B3

```
ATG AAA AAA ATG AAT AAG TTT TAT GAA AAA AGA GGC AAT TTC TAC CAG AAC ACT GTG GGT  1980
Met Lys Lys Met Asn Lys Phe Tyr Glu Lys Arg Gly Asn Phe Tyr Gln Asn Thr Val Gly   660

GAT CTG CTA AAG TTC ATC CGG AAT TTG GGA GAA CAC ATT GAT GAA GAA AAG CAT AAA AAG  2040
Asp Leu Leu Lys Phe Ile Arg Asn Leu Gly Glu His Ile Asp Glu Glu Lys His Lys Lys   680

ATG AAA TTA AAA ATT GGA GAC CCT TCC CTG TAT TTT CAG AAG ACA TTT CCA GAT CTG GTG  2100
Met Lys Leu Lys Ile Gly Asp Pro Ser Leu Tyr Phe Gln Lys Thr Phe Pro Asp Leu Val   700

ATC TAT GTC TAC ACA AAA CTA CAG AAC ACA GAA TAT AGA AAG CAT TTC CCC CAA ACC CAC  2160
Ile Tyr Val Tyr Thr Lys Leu Gln Asn Thr Glu Tyr Arg Lys His Phe Pro Gln Thr His   720

AGT CCA AAC AAA CCT CAG TGT GAT GGA GCT GGT GGG GCC AGT GGG TTG GCC AGC CCT GGG  2220
Ser Pro Asn Lys Pro Gln Cys Asp Gly Ala Gly Gly Ala Ser Gly Leu Ala Ser Pro Gly   740

TGC 2223  tgatggactgatttgctggagttcagggaactacttattagctgtagagtccttggcaaatcacaacat 2292
Cys  741

tctgggccttttaactcaccaggttgcttgtgagggatgagttgcatagctgatatgtcagtccctggcatcgtg    2367
tattccatatgtctataacaaaagcaatatatacccagactacactagtccataagctttacccactaactggga    2442
ggacattctgctaagattccttttgtcaattgcaccaaaagaatgagtgccttgacccctaatgctgcatatgtt    2517
acaattctctcacttaatttcccaatgatcttgcaaaacagggattatcatccccatttaagaactgaggaacc    2592
tgagactcagagagtgtgagctactggcccaagattattcaatttatacctagcactttataaatttatgtggtg    2667
ttattggtacctctcatttgggcaccttaaaacttaactatcttccagggctcttccagatgaggcccaaaacat    2742
atataggggttccaggaatctcattcattcattcagtatttattgagcatctagtataagtctgggcactggatg    2817
catgaatt  2825
```

P-loop cores- Cys-rich- PK homology-

```
Human  - MESRDHNNPQ EGPTSSSGRR AAVEDNHLLI KAVQNEDVDL VQQLLEGGAN VNFQEEEGGW  60
Murine - METPDYNTPQ GGTPSAGSQR TVVEDDSSLI KAVQKGDVVR VQQLLEKGAD ANACEDTWGW  60

Human  - TPLHNAVQMS REDIVELLLR HGADPVLRKK NGATLFILAA IAGSVKLLKL FLSKGADVNE 120
Murine - TPLHNAVQAG RVDIVNLLLS HGADPHRRKK NGATPFIIAG IQGDVKLLEI LLSCGADVNE 120

Human  - CDFYGFTAFM EAAVYGKVKA LKFLYKRGAN VNLRRKTKED QERLRKGGAT ALMDAAEKGH 180
Murine - CDENGFTAFM EAAERGNAEA LRFLFAKGAN VNLRRQTTKD KRRLKQGGAT ALMSAAEKGH 180

Human  - VEVLKILLDE MGADVNACDN MGRNALIHAL LSSDDSDVEA ITHLLLDHGA DVNVRGERGK 240
Murine - LEVLRILLND MKAEVDARDN MGRNALIRTL LNWDCENVEE ITSILIQHGA DVNVRGERGK 240

Human  - TPLILAVEKK HLGLVQRLLE QEHIEINDTD SDGKTALLLA VELKLKKIAE LLCKRGASTD 300
Murine - TPLIAAVERK HTGLVQMLLS REGINIDARD NEGKTALLIA VDKQLKEIVQ LLLEKGA-DK 299

Human  - CGDLVMTARR NYDHSLVKVL LSHGAKEDFH PPAEDWKPQS SHWGAALKDL HRIYRPMIGK 360
Murine - CDDLVWIARR NHDYHLVKLL LPYVANPDTD PPAGDWSPHS SRWGTALKSL HSMTRPMIGK 359

Human  - LKFFIDEKYK IADTSEGGIY LGFYEKQEVA VKTFCEGSPR AQREVSCLQS SRENSHLVTF 420
Murine - LKIFIHDDYK IAGTSEGAVY LGIYDNREVA VKVFRENSPR GCKEVSCLRD CGDHSNLVAF 419
```

```
Human  -  YGSESHRGHL FVCVTLCEQT LEACLDVHRG EDVENEEDEF ARNVLSSIFK AVQELHLSCG  480
Murine -  YGREDDKGCL YVCVSLCEWT LEEFLRLPRE EPVENGEDKF AHSILLSIFE GVQKLHLH-G  478

Human  -  YTHQDLQPQN ILIDSKKRAH LADFDKSIKW AGDPQEVKRD LEDLGRLVLY VVKKGSISFE  540
Murine -  YSHQDLQPQN ILIDSKKAVR LADFDQSIRW MGESQMVRRD LEDLGRLVLY VVMKGEIPFE  538

Human  -  DLKAQSNEEV VQLSPDEETK DLIHRLFHPG EHVRDCLSDL LGHPFFWTWE SRYRTLRNVG  600
Murine -  TLKTQNDEVL LTMSPDEETK DLIHCLFSPG ENVKNCLVDL LGHPFFWTWE NRYRTLRNVG  598

Human  -  NESDIKTRKS ESEILRLLQP GPSEHSKSFD KWTTKINECV MKKMNKFYEK R-GNFYQNTV  659
Murine -  NESDIKVRKC KSDLLRLLQH QTLEPPRSFD QWTSKIDKNV MDEMNHFYEK RKKNPYQDTV  658

Human  -  GDLLKFIRNL GEHIDEEKHK KMKLKIGDPS LYFQKTFPDL VIYVYTKLQN TEYRKHFPQT  719
Murine -  GDLLKFIRNI GEHINEEKKR G--------- ---------- ---------- ----------  679

Human  -  HSPNKPQCDG AGGASGLASP GC  741
```

```
HUMAN 2-5A dep. RNase    DQERLRKGGA  TALMDAAEKG  HVEVLKILLD  EMGADVNACD  NMGRNALIHA  209
    * E. coli RNase E    DRRKPRQNNR  ---RDRNERR  DTRSERTEGS  DNREE-NRRN  R--RQAQQQT  650
MURINE 2-5A dep. RNase   DKRRLKQGGA  TALMSAAEKG  HLEVLRILLN  DMKAEVDARD  NMGRNALIRT  209

HUMAN 2-5A dep. RNase    LLSSDDSDVE  AITHLLLDHG  ADVNVRGERG  KTPLILAVEK  KHLGLVQRLL  259
      E. coli RNase E    AETRESRQQA  EVTEKARTAD  EQQAPRRERS  RRRNDDKRQA  QQEA-KALNV  699
MURINE 2-5A dep. RNase   LLNWDCENVE  EITSILIQHG  ADVNVRGERG  KTPLIAAVER  KHTGLVQMLL  259

HUMAN 2-5A dep. RNase    EQEHIEINDT  DSDGKTALLL  AVELKLKKIA  EL---LCKRG  --ASTDCGDL  304
      E. coli RNase E    EEQSVQETEQ  EERVRPVQPR  RKQRQLNQKV  RYEQSVAEEA  VVAP-VVEET  748
MURINE 2-5A dep. RNase   SREGINIDAR  DNEGKTALLI  AVDKQLKEIV  QL---LLEKG  --AD-KODDL  303

HUMAN 2-5A dep. RNase    VMTARRNYD--  ---HSLVKVL  LSHGAKEDFH  PPAEDWKPQ  SSHWGAALKD  349
      E. coli RNase E    VAAEPIVQEAP  APRTELVKVP  LPVVAQ--TA  PEQQEENNA  DNRDNGGMPS  796
MURINE 2-5A dep. RNase   VWIARRNHD--  ---YHLVKLL  LPYVANPDTD  PPAGDWSPH  SSRWGTALKS  348
```

*ID SEQ NO:5:

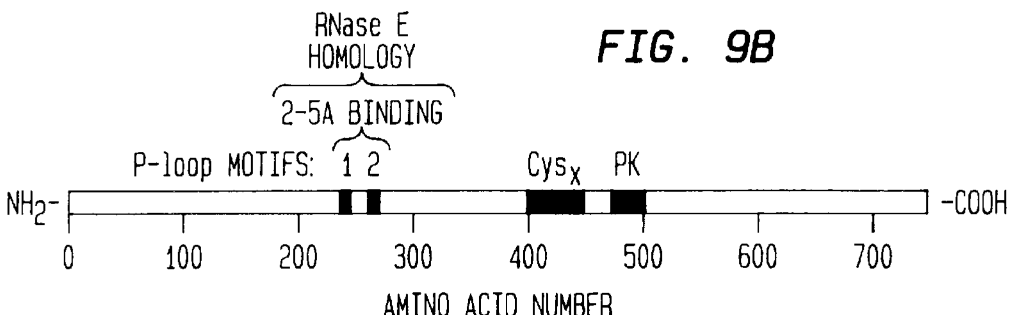

```
ANKYRIN CONSENSUS:        - G - T P L H Ψ A A - - G H - - Ψ V - - L L - - G A - - D - - - -
                                S A                           A                 N

REPEAT 1  *HUMAN    58   G G W T P L H N A V Q M S R E D I V E L L L R H G A D P V L R K K   90
          @MURINE        W G W T P L H N A V Q A G R V D I V N L L L S H G A D P H R R K K

REPEAT 2   HUMAN    91   N G A T L F I L A A I A G S V K L L K L F L S K G A D V N E C D F   123
           MURINE        N G A T P F I I A G I Q G D V K L L E I L L S C G A D V N E C D E

REPEAT 3   HUMAN   124   Y G F T A F M E A A V Y G K V K A L K F L Y K R G A N V N L R R K   156
           MURINE        N G F T A F M E A A E R G N A E A L R F L F A K G A N V N L R R Q

REPEAT 4   HUMAN   238   R G K T P L I L A V E K K H L G L V Q R L L E Q E H I E I N D T D   270
           MURINE        R G K T P L I A A V E R K H T G L V Q M L L S R E G I N I D A R D
```

*ID SEQ NO:6
@ID SEQ NO:7

FIG. 10B

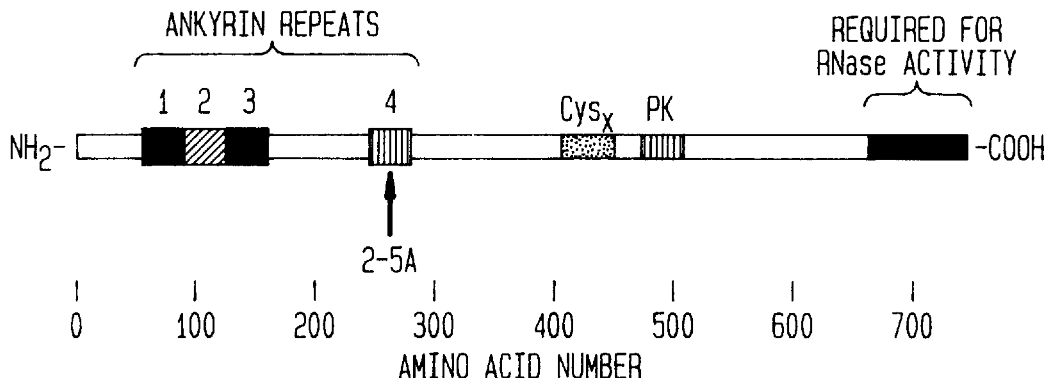

200 kDa
81 kDa
29 kDa
12.4 kDa
Absorbance
2–5A–Dependent RNase Activity, units (■)
12
8
4
2–5A–Binding Activity, counts per min X 10⁻³ (●)
4
3
2
1
0
Fraction Number
2
4
6
8
10
12
14
16
18
20
22
24
26
28
30
32
34
36
38
40

ANIMAL 2-5A-DEPENDENT RNASES AND ENCODING SEQUENCES THEREFOR

RELATED APPLICATIONS

This is a continuation Ser. No. 08/141,304 filed on Oct. 22, 1993, now abandoned which is a CIP of Ser. No. 08/028,086 filed on Mar. 8, 1993.

FIELD OF THE INVENTION

The present invention relates to isolated 2-5A-dependent RNases having the ability to bind 2-5A and/or cleave single stranded RNA when bound to 2-5A, encoding sequences therefor, recombinant nucleotide molecules, recombinant vectors and recombinant cells.

BACKGROUND

Control of RNA degradation is a critical cell function, and gene expression is often regulated at the level of RNA stability. See, e.g., Shaw, G. and Kamen, R., *Cell,* 46:659–667 (1986). Nevertheless, relatively little is known about the bio-chemical pathways that mediate RNA degradation in mammalian systems. For instance, most if not all of the ribonucleases responsible for mRNA turnover in mammalian cells remain unidentified. This was reviewed in Brawerman, G., *Cell,* 57:9–10 (1989). Presently, the 2-5A system is believed to be the only well-characterized RNA degradation pathway from higher animals including man. See FIG. 1. See also, e.g., Kerr, I. M. and Brown, R. E., *Proc. Natl. Acad. Sci. U.S.A.,* 75:256–260 (1978) and Cayley, P. J. et al., *Biochem. Biophys Res. Commun.,* 108:1243–1250 (1982); reviewed in Sen, G. C. and Lengyel, P., *J. Biol. Chem.,* 267:5017–5020 (1992). The activity of the 2-5A system is believed to be mediated by an endoribonuclease known as 2-5A-dependent RNase. See Clemens, M. J. and Williams, B. R. G., *Cell,* 13:565–572 (1978). 2-5A-dependent RNase is a unique enzyme in that it requires 2-5A, unusual oligoadenylates with 2', 5' phosphodiester linkages, $p_n(A2'p)_nA$, for ribonuclease activity. See Kerr, I. M. and Brown, R. E., *Proc. Natl. Acad. Sci. U.S.A.,* 75:256–260 (1978). 2-5A is produced from ATP by a family of synthetases in reactions requiring double-stranded RNA (dsRNA). See FIG. 1. See also Hovanessian, A. G. et al., *Nature,* 268:537–539 (1977); Marie, I. and Hovanessian, A. G., *J. Biol. Chem.,* 267:9933–9939 (1992). 2-5A is unstable in cells and in cell-free systems due to the combined action of 2', 5'-phosphodiesterase and 5'-phosphatase. See Williams, B. R. G. et al.; *Eur. J. Biochem.,* 92:455–562 (1978); and Johnson, M. I. and Hearl, W. G., *J. Biol. Chem.,* 262:8377–8382 (1987). The interaction of 2-5A-dependent RNase and 2-5A($k_d$=4×$10^{-11}$M), Silverman, R. H. et al., *Biol. Chem.,* 263:7336–7341 (1988), is highly specific. See Knight, M. et al., *Nature,* 288:189–192 (1980). 2-5A-dependent RNase is believed to have no detectable RNase activity until it is converted to its active state by binding to 2-5A. See Silverman, R. H., *Anal. Biochem.,* 144:450–460 (1985). Activated 2-5A-dependent RNase cleaves single-stranded regions of RNA 3' of UpNp, with preference for UU and UA sequences. See Wreschner, D. H. et al., *Nature,* 289:414–417 (1981a); and Floyd-Smith, G. et al., *Science,* 212:1020–1032 (1981). Analysis of inactive 2-5A-dependent RNase from mouse liver revealed it to be a single polypeptide of approximately 80 kDa. See Silverman, R. H. et al., *Biol. Chem.,* 263:7336–7341 (1988).

Although the full scope and biological significance of the 2-5A system remains unknown, studies on the molecular mechanisms of interferon action have provided at least some of the functions. Interferons α, β or γ are believed to induce the accumulation of both 2-5A-dependent RNase, Jacobsen, H. et al., *Virology,* 125:496–501 (1983A) and Floyd-Smith, G., *J. Cellular Biochem.,* 38:12–21 (1988), and 2-5A synthetases, Hovanessian, A. G. et al., *Nature,* 268:537–539 (1977), reviewed in Sen, G. C. and Lengyel, P., *J. Biol. Chem.,* 267:5017–5020 (1992). Furthermore, several investigations have implicated the 2-5A system in the mechanism by which interferon inhibits the replication of picornaviruses. Indeed, 2-5A per se and highly specific 2-5A mediated rRNA cleavage products were induced in interferon-treated, encephalomyocarditis virus (EMCV)-infected cells. See Williams, B. R. G., *Nature,* 282:582–586 (1979); Wreschner, D. H. et al., *Nucleic Acids Res.,* 9:1571–1581 (1981b); and Silverman, R. H. et al., *Eur. J. Biochem.,* 124:131–138 (1982a). In addition, expression of 2-5A synthetase cDNA inhibited the replication of picornaviruses, Chebath, J., *Nature,* 330:587–588 (1987) and Rysiecki, E. F. et al., *J. Interferon Res.,* 9:649–657 (1989), and the introduction of a 2-5A analogue inhibitor of 2-5A-dependent RNase into cells reduced the interferon-mediated inhibition of EMCV replication. See Watling, D. et al., *EMBO J.,* 4:431–436 (1985). Further, 2-5A-dependent RNase levels were correlated with the anti-EMCV activity of interferon, Kumar, R. et al., *J. Virol.,* 62:3175–3181 (1988), and EMCV-derived dsRNA both bound to and activated 2-5A synthetase in interferon-treated, infected cells. See Gribaudo, G. et al., *J. Virol.,* 65:1948–1757 (1991).

The 2-5A system, however, almost certainly provides functions beyond the antipicornavirus activity of interferons. For instance, introduction of 2-5A into cells, Hovanessian, A. G. and Wood, J. N., *Virology,* 101:81–90 (1980), or expression of 2-5A synthetase cDNA, Rysiecki, G. et al., *J. Interferon Res.,* 9:649–657 (1989), inhibits cell growth rates. Moreover, 2-5A-dependent RNase levels are elevated in growth arrested cells, Jacobsen, H. et al., *Proc. Natl. Acad. Sci. U.S.A.,* 80:4954–4958 (1983b), and 2-5A synthetase, Stark, G. et al., *Nature,* 278:471–473 (1979), and 2-5A-dependent RNase levels are induced during cell differentiation. See, e.g., Krause, D. et al., *Eur. J. Biochem.,* 146:611–618 (1985). Therefore, interesting correlations exist between 2-5A-dependent RNase and the fundamental control of cell growth and differentiation suggesting that the 2-5A system may function in general RNA metabolism. The ubiquitous presence of the 2-5A system in reptiles, avians and mammalians certainly supports a wider role for the pathway. See, for example, Cayley, P. J. et al., *Biochem. Biophy. Res. Commun.,* 108:1243–1250 (1982).

Notwithstanding the importance of 2-5A-dependent RNase to the 2-5A system, 2-5A-dependent RNase enzymes having ribonuclease function have not been isolated, purified or sequenced heretofore. Consequently, there is a demand for isolated, active 2-5A-dependent RNases and their complete amino acid sequences, as well as a demand for encoding sequences for active 2-5A-dependent RNases.

SUMMARY OF THE INVENTION

In brief, the present invention alleviates and overcomes certain of the above-mentioned problems and shortcomings of the present state of the art through the discovery of novel, isolated 2-5A-dependent RNases and encoding sequences therefor.

Broadly speaking, the novel 2-5A dependent RNases of the instant invention are involved in the fundamental control of single stranded RNA decay in animal cells, such as mammals, and are also present in animal cells, such as avian and reptilian cells. More particularly, the novel 2-5A dependent RNases of the present invention have the ability to degrade single stranded RNA, mainly 3' of UpUp or UpAp sequences, after they are activated by binding to 5'-phosphorylated,2',5'-linked oligoadenylates (hereinafter "2-5A"). As a result, it is believed that the novel 2-5A dependent RNases are useful in connection with inhibition of cell growth rates, viral replication and in connection with interferon treatment of viral infection and cancer. As used herein, the term "2-5A-dependent RNase(s)" is used in a broad sense and is meant to include any amino acid sequence which includes a 2-5A binding domain and/or ribonuclease function when the 2-5A-dependent RNase is activated by 2-5A.

The novel 2-5A dependent RNases of the present invention are protein enzymes having molecular weights on the order of between about 74 KDa (murine) and about 84 KDa (human), as determined by gel electrophoresis migration and/or prediction from their respective encoding nucleotide sequences. For example, a human 2-5A-dependent RNase of the instant invention has a molecular weight of about 83,539 Da as determined from the amino acid sequence predicted from the encoding sequence therefor, whereas the murine 2-5A-dependent RNase has a molecular weight of about 74 KDa as determined by gel electrophoresis migration and from prediction of the amino acid sequence from the encoding sequence. While an about 74 KDa molecular weight is reported herein for a murine 2-5A-dependent RNase, it should nevertheless be appreciated that the reported molecular weight is for an incomplete murine 2-5A-dependent RNase. It is nevertheless believed that once completely sequenced, i.e., when an about 84 amino acid end region is identified, the molecular weight of a complete murine 2-5A-dependent RNase will be similar to that of human, i.e., about 84 KDa.

It should also be readily apparent to those versed in this art, however, that since gel electro-phoresis migration has been employed to determine molecular weight of a murine 2-5A-dependent RNase, the 74 KDa molecular weight is only an estimate based upon relative migration.

The amino acid sequence for human 2-5A-dependent RNase protein (SEQ ID NO: 2) is depicted in FIG. 3 and Table 1. The encoding sequence (SEQ ID NO: 1) for the human 2-5A-dependent RNase protein is also set forth in Table 1. The mRNA for human 2-5A-dependent RNase is about 5.0 Kb in size. The virtually complete amino acid sequence for the murine 2-5A-dependent RNase protein (SEQ ID NO: 4) and the encoding sequence (SEQ ID NO: 3) therefore is depicted in Table 2. The mRNA for murine 2-5A-dependent RNase is about 5.7 Kb in size.

Analysis of the amino acid sequences of the 2-5A-dependent RNases of the present invention have revealed several characteristics unique to the 2-5A-dependent RNases. For example, it has been discovered that the novel 2-5A dependent RNases of the instant invention include the following unique domains which span between the amino terminus and the carboxy terminus. For instance, it has been discovered that there are at least four ankyrin repeats, of which three lie closest to the amino terminus. However, while four ankyrin repeats have been discovered, it is believed that there may be additional ankyrin repeats that may total, for instance, about eight or more when the amino acid sequences of the 2-5A-dependent RNases of the present invention are further analyzed. It is believed that these ankyrin repeats may possibly function in protein-protein interaction. Ankyrin repeat 1 generally lies between amino acids designated as 58–90 in Tables I (SEQ ID NO: 2) and II (SEQ ID NO: 4). Ankyrin repeat 2 generally lies between amino acids designated as 91–123 in Tables I (SEQ ID NO: 2) and II (SEQ ID NO: 4). Ankyrin repeat 3 generally lies between amino acids designated as 124–156 in Tables I (SEQ ID NO: 2) and II (SEQ ID NO: 4). Ankyrin repeat 4 generally lies between amino acids designated as 238 and 270 in Tables I (SEQ ID NO: 2) and II (SEQ ID NO: 4). See also FIGS. 10A and 10B.

It has also been discovered that the novel 2-5A dependent RNases include a cysteine rich region (which has homology to zinc fingers) that lies closer to the carboxy terminus than the amino terminus which may possibly function in RNA recognition or in formation of protein dimers. The cysteine rich region is believed to include about 5 or 6 cysteine residues which generally lie between amino acids designated as 395–444 in the human sequence (SEQ ID NO: 2) as reported in Table I and FIG. 4, or between amino acids designated as 401–436 in the murine sequence (SEQ ID NO: 4) as reported in Table II and FIG. 4.

Still further, it has been discovered that the novel 2-5A dependent RNases include a duplicated phosphate binding (2 P-loops) motif which lies generally between the three ankyrin repeats motif and the cysteine-rich region. Even though the phosphate binding P-loop motifs generally follow the three ankyrin repeats, the fourth ankyrin repeat is contained within the repeated P-loop motifs. It is believed that the two P-loops are in the same orientation and constitute the binding domain necessary for binding 2-5A. It is further believed that each P-loop motif includes a lysine residue which is essential for maximum 2-5A binding activity. The lysine residues are designated as 240 and 274 in Tables I and II.

It has been further discovered that the 2-5A-dependent RNase proteins contain an amino acid region which follows the cysteine rich region that is believed to be homologous to protein kinases. Within this region, there is believed to be separate domains designated as domains VI and VII which generally lie between amino acid residues designated as 470–504 in Tables I (SEQ ID NO: 2) and II (SEQ ID NO: 4). More particularly, as to the human sequence of 2-5A-dependent RNase, domain VI generally lies between amino acid residues designated as 471–491 (of SEQ ID NO: 2) and domain VII generally lies between amino acid residues designated as 501–504(of SEQ ID NO: 2), as reported in Table I and FIG. 4. As to the murine sequence of the 2-5A-dependent RNase, domain VI generally lies between amino acids designated as 470–489 (of SEQ ID NO: 4) and domain VII generally lies between amino acid residues designated as 499–502(of SEQ ID NO: 4), as reported in Table II and FIG. 4.

It has also been discovered that there is limited homology between the amino acid sequences for the 2-5A-dependent RNases of the present invention and RNase E (SEQ ID NO: 5), encoded by the altered mRNA stability (ams)/rne gene of *E. Coli*. Uniquely, the limited homology is generally conserved between the murine and human amino acid sequences for 2-5A-dependent RNases and generally lies between a 200 amino acid region. More particularly, for the human sequence, the amino acid region spans amino acid residues designated as 160–349 in Table I (SEQ ID NO: 2) and FIGS. 9A and 9B. With respect to the murine sequence, the amino acid region spans amino acid residues designated as 160–348 in Table II (SEQ ID NO: 4) and FIGS. 9A and 9B.

It has been further discovered and is believed that almost the entire, if not complete, amino acid sequences of the novel 2-5A-dependent RNase proteins of the instant invention are necessary for ribonuclease function. For example, it is believed that, when an about 84 amino acid region at the carboxy terminus is present in the human 2-5A-dependent RNase, the human 2-5A-dependent RNase has ribonuclease function in the presence of 2-5A. In contrast, when the murine 2-5A-dependent RNase lacks the about 84 amino acid region at the carboxy terminus, it lacks ribonuclease function.

With respect to the binding activity of a murine 2-5A-dependent RNase protein to 2-5A, it has been discovered that, when one P-loop is deleted from the repeated P-loop motif of a murine 2-5A-dependent RNase protein, nearly all 2-5A binding activity is lost, and that when both P-loops are deleted, virtually complete activity is lost. However, it has been found that, even though the carboxy terminus portion of the amino acid sequence of a murine 2-5A-dependent RNase protein following the repeated P-loop motif has been deleted, partial 2-5A binding activity is maintained.

It has been further discovered that when lysine residues 240 and 274 are replaced with asparagine residues in both P-loop motifs, significant 2-5A binding activity of a murine 2-5A-dependent RNase protein is lost. It has been further discovered, however, that when either lysine residue 240 or 274 is replaced in either P-loop motif, only partial 2-5A binding activity is lost. It is therefore believed that the presence of both P-loop motifs in the amino acid sequences for the 2-5A dependent RNases of the present invention plays an important role in 2-5A binding activity. It is further believed that the presence of lysine residues 240 and 274 in each P-loop motif plays an important role for enhanced 2-5A binding activity. It is also believed that the presence of virtually the entire amino acid sequence of the 2-5A-dependent RNases of the present invention provides for even further enhanced 2-5A binding activity, as well as provides for ribonuclease function.

In addition, the present invention relates to the cloning of murine and human 2-5A-dependent RNases and novel murine and human clones. Recombinant and naturally occurring forms of 2-5A-dependent RNase displayed virtually identical 2-5A binding properties and ribonuclease specificities.

The present invention further contemplates the use of the novel isolated, 2-5A-dependent RNases and encoding sequences therefor, as well as analogs and active fragments thereof, for use, for instance, 1.) in gene therapy for human and animal diseases including viral disease and cancer, 2.) as genetic markers for human disease due to perhaps cancer or viral infection, 3.) to develop plants and animals resistant to certain viruses, and 4.) as enzymes in connection with research and development, such as for studying the structure of RNA. In one manner to accomplish the above, and as contemplated by the present invention, the encoding sequences of the instant invention may be utilized in ex vivo therapy, i.e., to develop recombinant cells using the encoding sequence of the present invention using techniques known to those versed in this art. In another manner which may be employed to accomplish the above, the encoding sequences of the present invention may be combined with an appropriate promoter to form a recombinant molecule and inserted into a suitable vector for introduction into an animal, plant, or other lower life forms also using techniques known to those skilled in this art. Of course, other suitable methods or means known to those versed in this art may be selected to accomplish the above-stated objectives or other objectives for which the novel 2-5A-dependent RNases and encoding sequences of the present invention are suited.

While the present invention is described herein with reference to the particular sequences disclosed, it should nevertheless be understood by those skilled in this art that the present invention contemplates variations to the amino acid and/or nucleotide sequences which do not destroy 2-5A binding activity and/or ribonuclease activity. Therefore, the present invention contemplates any analogs or fragments of the 2-5A-dependent RNases or the encoding sequences therefor which are active. In other words, the present invention includes any amino acid or nucleotide sequence which has the ability to accomplish the objectives of the instant invention, i.e., any amino acid sequence which has 2-5A binding activity and/or ribonuclease activity and any nucleotide sequence which encodes for an amino acid sequence having 2-5A binding activity and/or ribonuclease activity.

The present invention is also directed to the baculovirus expression and purification of recombinant human 2-5A-dependent RNase. The recombinant enzyme is expressed in insect cells in a soluble and fully functional form. The insect cell expression system also has the advantage of having no endogenous 2-5A-dependent RNase. The levels of 2-5A-dependent RNase which were obtained are several orders of magnitude higher than those present in normal mammalian cells and tissues. Therefore, it is now feasible to produce and purify tens of milligrams of 2-5A-dependent RNase. Such levels of purified enzyme will allow meaningful biophysical studies to be conducted on 2-5A-dependent RNase. Such studies could provide the eventual elucidation of the molecular mechanisms of 2-5A activation of ribonuclease activity and the selection of RNA cleavage sites.

The above features and advantages of the present invention will be better understood with reference to the accompanying FIGS., Detailed Description and Example. It should also be understood that the particular methods, proteins, encoding sequences and compositions illustrating the invention are exemplary only and not to be regarded as limitations of the invention.

BRIEF DESCRIPTION OF THE FIGURES

Reference is now made to the accompanying FIGS. in which is shown illustrative embodiments of the present invention from which its novel features and advantages will be apparent.

FIG. 2A is a specific affinity of truncated murine 2-5A-dependent RNase for 2-5A. UV covalent crosslinking of the $^{32}$P-2-5A probe (lanes 1–7) to protein is performed after translation reactions in wheat germ extract (5 $\mu$l) with murine 2-5A-dependent RNase mRNA (from clone ZB1) (lanes 1–3) or without added RNA (lane 4) or in extract of interferon treated mouse L cells (100 $\mu$g of protein) (lanes 5–7). Reactions are without added competitor (lanes 1, 4, and 5) or in the presence of either trimer core. $(A2'p)_2A$, (100 nM) (lanes 2 and 6) or trimer 2-5A, $p_3(A2'p)_2A$ (100 nM) (lanes 3 and 7). Lanes 8 and 9 are produced by incubating the wheat germ extract with $^{35}$S-methionine in the absence or presence of 2-5A-dependent RNase mRNA, respectively.

FIG. 2B are identical chymotrypsin cleavage products and are obtained from recombinant and naturally occurring form of 2-5A-dependent RNase. Partial chymotrypsin digests (arrows) are performed on truncated 2-5A-dependent RNase (clone ZB1) produced in wheat germ extract ("Recombinant") and murine L cell 2-5A-dependent RNase ("Naturally Occurring") after crosslinking to the 2-5A probe and purification from gels.

FIG. 3A is the construction of a human 2-5A-dependent RNase clone. The initial human 2-5A-dependent RNase cDNA clone, HZB1, is isolated from an adult human kidney cDNA library in λgt10 using radiolabeled murine 2-5A-dependent RNase cDNA (clone ZB1) as probe. See Example. Radiolabeled HZB1 DNA is used to isolate a partially overlapping cDNA clone, HZB22, which is fused to HZB1 DNA at the NcoI site to form clone ZC1. The 5'-region of the coding sequence is obtained from a genomic SacI fragment isolated using a radiolabeled HZB22 DNA fragment as probe. Fusion of the genomic SACI fragment with ZC1 at the indicated SacI site produces clone ZC3. The coding sequence with some flanking sequences is then subcloned as a HindIII fragment into pBluescript KS(+) (Stratagene) resulting in clone ZC5. The restriction map for the composite clone, ZC5, is shown. Clone HZB1 includes nucleotides designated as 658–2223 in Table I which encode for amino acids designated as 220–741 in Table I. Clone HZB22 includes a nucleotide sequence which encodes for amino acids designated as 62–397 in Table I. Clone ZC1 includes a nucleotide sequence which encodes for amino acids designated as 62–741 in Table I. Clones ZC3 and ZC5 both include nucleotide sequences which encode for amino acids designated as 1–741 in Table I.

FIGS. 3B1, 3B2, 3B3 and 3B4 are the nucleotide sequence predicted amino acid sequence of human 2-5A-dependent RNase with flanking nucleotide sequences. The numbers to the right on each of FIGS. 3B1–3B4 indicate the positions of nucleotides and amino acid residues.

FIG. 3B shows the sequential order of FIGS. 3B1–3B4for human 2-5A-dependent RNase.

FIGS. 4A and 4B are the is alignment of the predicted amino acid sequences for murine and human forms of 2-5A-dependent RNase. The positions of the repeated P-loop motifs, the cysteine (Cys)-rich regions with homology to zinc fingers, and the regions of homology to protein kinase domains VI and VII are indicated. Amino acids residues which are important components of the indicated domains are represented in bold type and are italicized. Identical amino acid residues in murine and human 2-5A-dependent RNase are indicated with colon (:) symbols adjacent therebetween.

FIG. 4 shows the sequential order of FIGS. 4A and 4B for murine and human forms of 2-5A-dependent RNase.

FIG. 5A is specific affinity of recombinant human 2-5A-dependent RNase for 2-5A. Crosslinking of the 2-5A probe (lanes 1–7) to protein is performed after translation reactions in wheat germ extract (5 μl) with human 2-5A-dependent RNase mRNA (lanes 1–3) or without added RNA (lane 4) or in extract of human interferon α treated (1000 units per ml for 16 h) human HeLa cells (350 μg of protein) (lanes 5–7). Reactions were without added competitor (lanes 1, 4, and 5) or in the presence of either trimer core, $(A2'p)_2A$, (100 nM) (lanes 2 and 6) or trimer 2-5A, $p_3(A2'p)_2A$ (100 nM) (lanes 3 and 7). Incubations with $^{35}$S-methionine are shown in lanes 8 to 12. Lane 8 is with wheat germ extract and human 2-5A-dependent RNase mRNA. Reticulocyte lysate preadsorbed to 2-5A-cellulose is incubated with human 2-5A-dependent RNase mRNA in the absence (lane 9) or presence (lane 10) of cycloheximide, or in the absence of added mRNA (lane 11). Lane 12 shows human 2-5A-dependent RNase which is produced in the nonadsorbed, crude reticulocyte lysate. The positions and relative molecular masses (in kDa) of the marker proteins are indicated.

FIG. 5B is reticulocyte lysate pretreated to remove endogeous 2-5A-dependent RNase and is incubated in the absence of added mRNA (■), in the presence of human 2-5A-dependent RNase mRNA without inhibitor (●, ■) or in the presence of both 2-5A-dependent RNase mRNA and cycloheximide (50 μg per ml (●). See Example. Subsequently, the recombinant 2-5A-dependent RNase (or controls) is adsorbed to 2-5A-cellulose and ribonuclease assays are performed after extensive washing of the matrix to reduce general nuclease activity. Radiolabeled substrate RNA was either poly(U) (○, ●, ■) or poly(C) (■).

FIG. 6A is a northern blot prepared with poly(A)$^+$RNA (4 μg per lane) that is isolated from murine L929 cells treated with murine interferon (α+β) (1000 units per ml) and/or cycloheximide (50 μg per ml) for different durations (indicated) which is probed with radiolabeled murine 2-5A-dependent RNase cDNA. Interferon, IFN; cycloheximide, CHI.

FIG. 6B shows levels of 2-5A-dependent RNase which are estimated from the autoradiogram shown in panel (a) with a video camera and QuickCapture and Image computer programs.

FIG. 6C shows levels of glyceraldehyde-3-phosphate dehydrogenase (GAPDH) mRNA as determined in the same blot shown in panel (A).

FIG. 7A shows incubations of truncated 2-5A-dependent RNase, clone ZB1, ("Recombinant") which is produced in wheat germ extract (upper panel) or of murine L cell 2-5A-dependent RNase (labeled "Naturally Occurring," lower panel) with the $^{32}$P-2-5A probe, (2.4 nM), are in the absence of presence of unlabeled 2',5'-phosphodiester linked oligonucleotides (as indicated) followed by uv covalent crosslinking. Autoradiograms of the dried SDS/10% polyacrylamide gels are shown. Concentrations of the oligonucleotide competitors are indicated. I is inosine.

FIG. 7B shows a truncated series of murine 2-5A-dependent RNase mutants (ZB1 to ZB15) which is produced in wheat germ extract which are assayed for 2-5A binding activity by a filter binding method. See Example and Knight et al. (1980). The positions of the P-loop motifs and the lengths of the translation products are indicated. Clone ZB1 encodes for amino acids designated as 1–656 in Table II, except for the last 5 amino acid residues which are Lys, Pro, Leu, Ser, and Gly. Clone ZB2 encodes for amino acids designated as 1–619 in Table II. Clone ZB3 encodes for amino acids designated as 1–515 in Table II. Clone ZB5 encodes for amino acids designated as 1–474 in Table II. Clone ZB9 encodes for amino acids designated as 1–403 in Table II. Clone ZB10 encodes for amino acids designated as 1–365 in Table II. Clone ZB13 encodes for amino acids designated as 1–294 in Table II. Clone ZB14 encodes for amino acids designated as 1–265 in Table II. Clone ZB15 encodes for amino acids designated as 1–218 in Table II.

FIG. 8A shows the truncated murine 2-5A-dependent RNase, clone ZB1, and lysine to asparagine substitution mutants of clone ZB1, which are synthesized in wheat germ extract. In (A) unlabeled translation products are covalently crosslinked to the bromine-substituted, $^{32}$P-labeled 2-5A probe, Br-2-5A-[$^{32}$P]pCp. See Nolan-Sorden, N. L., et al., *Anal. Biochem.,* 184:298–304, 1990.

FIG. 8B shows the mRNA species which are translated in the presence of $^{35}$-S-methionine in separate reactions. Autoradiograms of the dried, SDS/polyacrylamide gels are shown. The order and positions of the translation products (labelled "RNase") and the relative molecular masses (in kDa) of the protein markers are indicated.

FIGS. 9A and 9B are a comparison of the amino acid sequences of RNase E and 2-5A-dependent RNase.

FIG. 9A shows identical and conservative matches which are shown between *E. coli* RNase E (SEQ ID NO: 5) and the murine and human forms of 2DR the *E.coli* RNase E sequence is identified as ID SEQ NO:5:.

FIG. 9B is a model for the structure and function of 2DR. Abbreviations: P-loop motifs, a repeated sequence with homology to P-loops; Cys$_x$, a cysteine-rich region with homology to certain zinc fingers; PK, homology to protein kinase domains VI and VII.

FIGS. 10A and 10B are a comparison of the amino acid sequences of the ankyrin repeats in the human and murine 2-5A-dependent RNase proteins.

FIG. 10A shows murine and human forms of 2-5A-dependent RNases containing four ankyrin repeats. Homology between the ankyrin consensus sequence (SEQ ID NO: 6)and the murine and human forms of 2-5A-dependent RNase are indicated. ψ, hydrophobic amino acids.

FIG. 10B is a model showing the relative positions of the four ankyrin repeats in 2-5A-dependent RNase in comparison to the position of the proposed 2-5A binding domain (↑) (the repeated P-loop motif); Cys$_x$, the cysteine-rich region; PK, the protein kinase homology region, and the carboxy-terminal region required for RNase activity.

DETAILED DESCRIPTION

By way of illustrating and providing a more complete appreciation of the present invention and many of the attendant advantages thereof, the following Detailed Description and Example is given concerning the novel 2-5A-dependent RNases, encoding sequences therefore, recombinant nucleotide molecules, vectors and cells.

Because 2-5A-dependent RNase is very low in abundance (one five-hundred-thousandth of the total protein in mouse liver, Silverman, R. H. et al., *J. Biol. Chem.,* 263:7336–7341 (1988)), its cloning requires the development of a sensitive screening method. Murine L929 cells are selected as the source of mRNA due to high basal levels of 2-5A-dependent RNase. A protocol to enhance 2-5A-dependent RNase mRNA levels is developed based on the observation that optimal induction of 2-5A-dependent RNase is obtained by treating cells with both interferon and cycloheximide, then with medium alone. See Example. The cDNA library is screened by an adaptation of techniques developed for cloning DNA binding proteins, Singh, H. et al., *Cell,* 52:415–423 (1988); Singh H. et al., *BioTechniques,* 7:252–261 (1989), in which a bromine-substituted $^{32}$P-labeled 2-5A analogue ("2-5A probe"), Example and Nolan-Sorden, N. L. et al., *Anal. Biochem.,* 184:298–304 (1990), replaced a radiolabeled oligodeoxyribonucleotide. A single clone (ZB1) is thus isolated from about three million plaques. The protein expressed from the ZB1 clone, transferred from plaques to filter-lifts, shows reactivity to both the 2-5A probe and to a highly purified polyclonal antibody directed against 2-5A-dependent RNase.

Figure 2A:
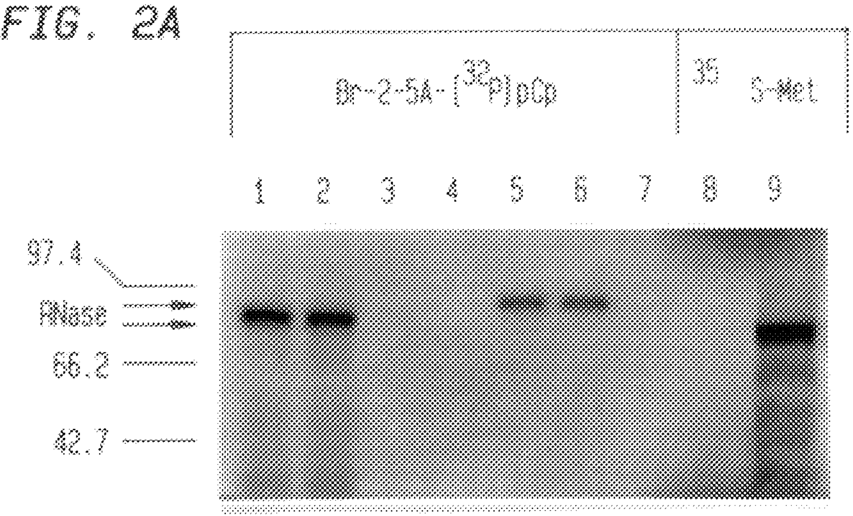
FIGS. 2A and 2B is a comparison of 2-5A binding activity of recombinant and naturally occurring forms of murine 2-5A-dependent RNase.
Figure 2B:
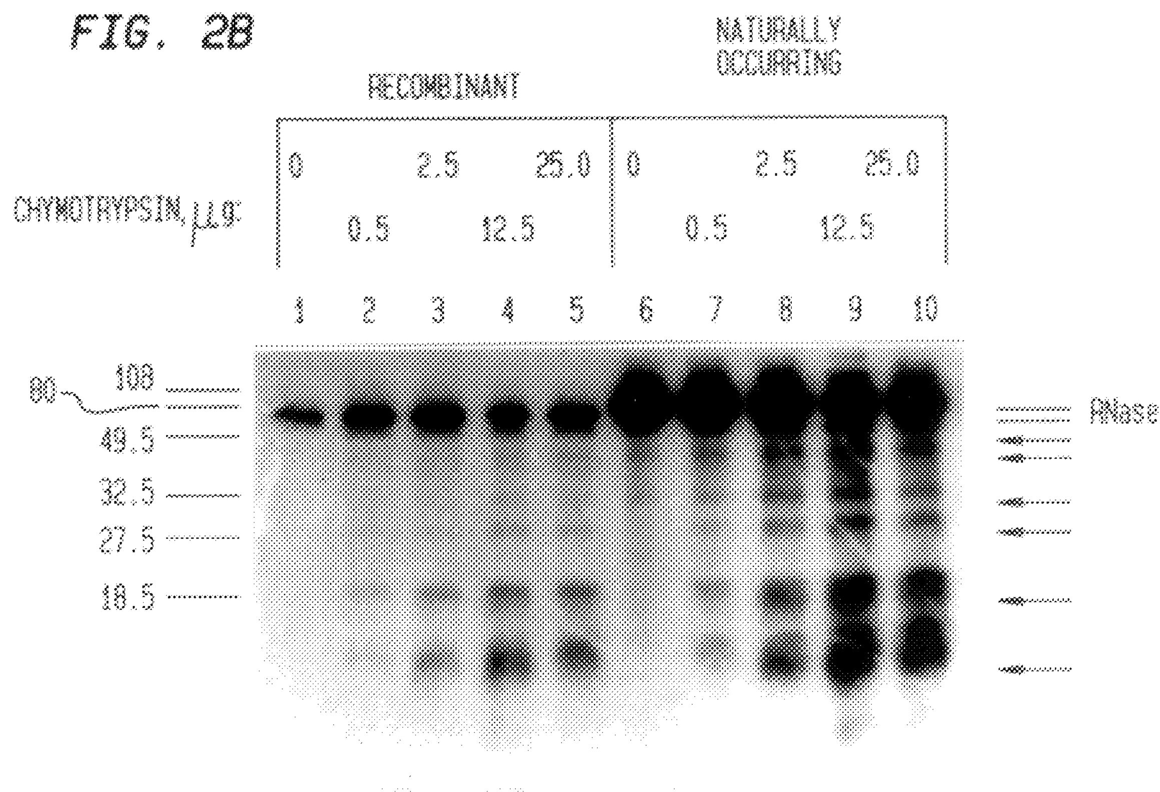

To obtain recombinant protein for characterization, the cDNA is transcribed and translated in cell-free systems. See Example. 2-5A binding activity is then determined by covalently crosslinking the 2-5A probe to the protein with uv light, for example, Nolan-Sorden, N. L. et al., *Anal. Biochem.,* 184:298–304 (1990). The recombinant 74 kDa protein produced in a wheat germ extract shows specific affinity for the 2-5A probe. See FIG. 2A, lanes 1 to 3. A core derivative of 2-5A lacking 5'-phosphoryl groups, $(A2'p)_2A$, fails to interfere with binding of the protein to the 2-5A probe whereas trimer 205A, $p_3(A2'p)_2A$, completely prevents probe binding. See FIG. 2A, lanes 2 and 3, respectively. There is no detectable 2-5A binding proteins in the wheat germ extract as shown in the incubation without added RNA, FIG. 2A, lane 4. For comparison, a similar profile of 2-5A binding activity is obtained for the 80 kDa 2-5A-dependent RNase from murine L929 cells, incubated without added oligonucleotide or with $(A2'p)_2A$ or $p_3(A2'p)_2A$ as competitors. See FIG. 2A, lanes 5 to 7. The $^{35}$S-labeled translation product is shown in FIG. 2A, lane 9. In a further comparison, covalent linkage of the 2-5A probe to the about 74 kDa protein and to murine L929 cell 2-5A-dependent RNase followed by partial digestion with chymotrypsin produces an identical pattern of six labeled peptides. See FIG. 2B. Similarly, partial digestion of the two labeled proteins with *S. aureus* V8 protease also produces identical patterns of labeled cleavage products. These results and the apparent molecular weight of about 74 kDa for the recombinant protein, as compared to about 80 kDa for 2-5A-dependent RNase, see FIG. 2A, suggests that the about 74 kDa protein is a truncated, or partial clone for 2-5A-dependent RNase.

Figure 3A:
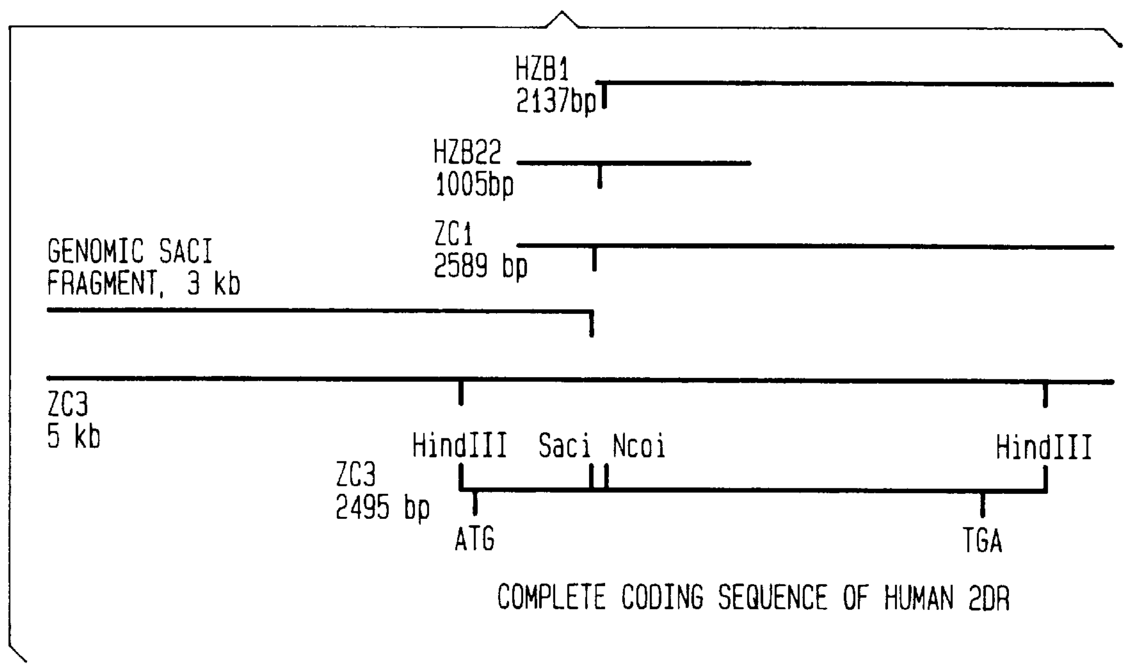
FIGS. 3A and 3B are clonings of the complete coding sequence for human 2-5A-dependent RNase.
Figure 3B:
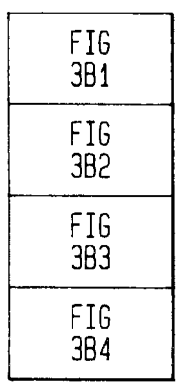

To obtain the entire coding sequence for human 2-5A-dependent RNase, a composite DNA containing genomic and cDNA is constructed. See FIG. 3A. The initial cDNA portion of the human 2-5A-dependent RNase clone (HZB1) is obtained by screening a human kidney cDNA library with radiolabeled murine 2-5A-dependent RNase cDNA. See Example. A genomic clone, containing the 5'-part of the coding sequence, is isolated with radiolabeled human 2-5A-dependent RNase cDNA. The nucleotide and predicted amino acid sequences of human 2-5A-dependent RNase are determined, FIG. 3B, resulting an open reading frame encoding a protein of 83,539 Da.

Figure 4:
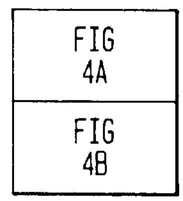

A comparison is made between the predicted amino acid sequences of the human and murine forms of 2-5A-dependent RNase in order to identify and evaluate the conserved regions of the proteins. See FIG. 4. The murine cDNA, clone ZB1, contains about 88% of the coding sequence for 2-5A-dependent RNase to which an additional twenty-eight 3'-codons are added from a murine genomic clone. Alignment of the murine and human forms of 2-5A-dependent RNase indicates about 65% identity between the overlapping regions. See FIG. 4. In addition, there is 73% identity between the corresponding nucleotide sequences for murine and human 2-5A-dependent RNase. The apparent translation start codons for both the murine and human 2-5A-dependent RNases, are in an appropriate context for translational initiation, namely ACC<u>ATG</u>G and GTC <u>ATG</u>G, respectively. See FIG. 3B. See also, for example, Kozak, M., *Cell,* 44:283–292 (1986). In addition, both the human and murine 2-5A-dependent RNase sequences contain in-frame stop codons upstream of the translation start sites. See FIG. 3B.

The 2-5A binding properties of the recombinant and naturally occurring forms of human 2-5A-dependent RNase are compared by uv covalent crosslinking to the 2-5A probe. The recombinant human 2-5A-dependent RNase produces in wheat germ extract shows specific affinity for 2-5A. See FIG. 5A, lanes 1 to 3. Radiolabeling of the cloned human 2-5A-dependent RNase with the 2-5A probe is not prevented by $(A2'p)_2A$. See FIG. 5A, lanes 1 and 2. In contrast, addition of trimer 2-5A, $p_3(A2'p)_2A$, effectively competes with the 2-5A probe for binding to the recombinant 2-5A-dependent RNase. See lane 3. The same pattern of 2-5A binding activity is obtained with 2-5A-dependent RNase in an extract of interferon-treated human HeLa cells. See FIG. 5A, lanes 5 to 7. The apparent molecular weights of HeLa cell 2-5A-dependent RNase and $^{35}$S-labeled recombinant human 2-5A-dependent RNase produced in reticulocyte lysate are believed to be exactly the same (about 80 kDa). See FIG. 5A, lanes 5 and 9. The recombinant human 2-5A-dependent RNase produced in wheat germ extract migrates slightly faster probably due to post-translational modifications. See FIG. 5A, lanes 1, 2 and 8.

Figure 5A:
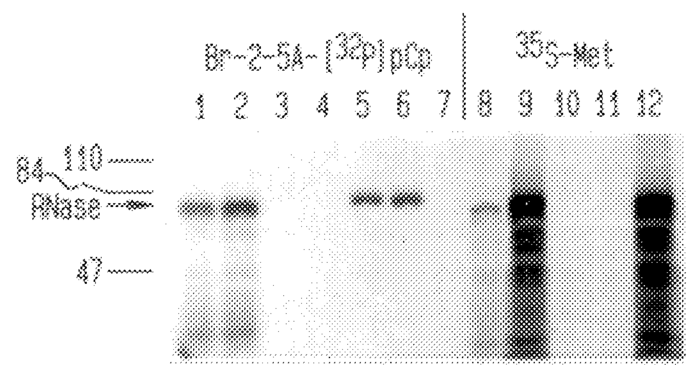
FIGS. 5A and 5B are 2-5A binding properties and ribonuclease activity of recombinant human 2-5A-dependent RNase produced in vitro.
Figure 5B:
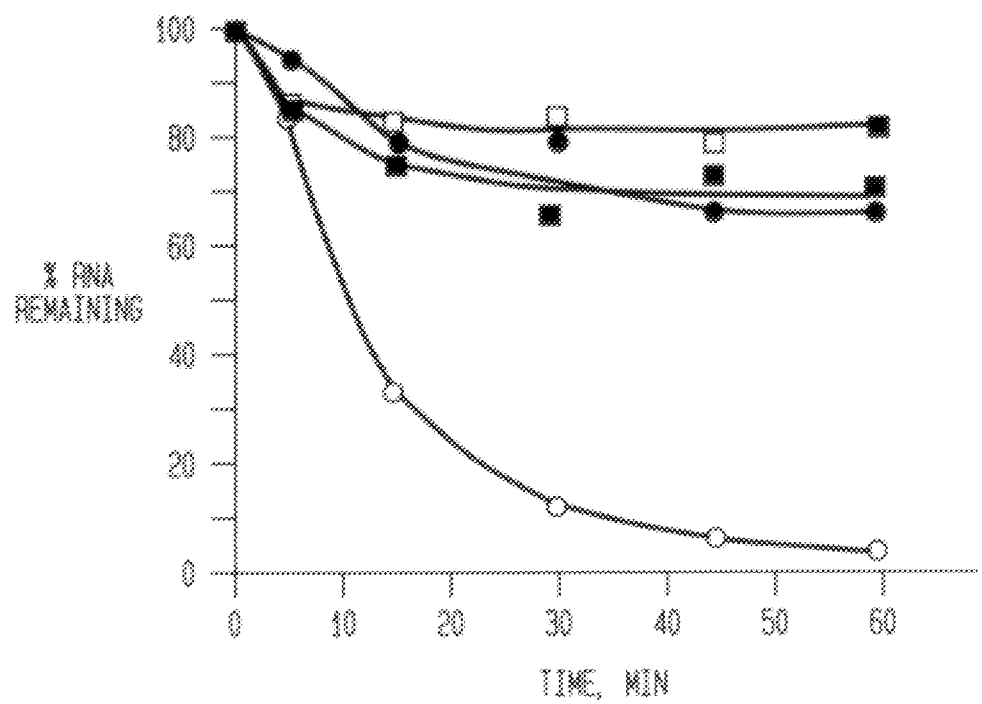

To demonstrate and characterize the ribonuclease activity of the cloned 2-5A-dependent RNase, translation is performed in a reticulocyte lysate instead of a wheat germ extract due to the substantially greater efficiency of protein synthesis in the former system. See FIG. 5A, compare lanes 9 and 8. Prior to translation, endogenous reticulocyte 2-5A-dependent RNase is removed by adsorbing the lysate to the affinity matrix, 2-5A-cellulose. See Example. See also, Silverman, R. H., *Anal. Biochem.,* 144:450–460 (1985). The treatment with 2-5A-cellulose effectively removes all measurable endogenous 2-5A-dependent RNase activity from the lysate, as determined by 2-5A-dependent ribonuclease assays, and FIG. 5B. In addition, the adsorption-depletion protocol did not reduce translational efficiency. FIG. 5A, lanes 9 and 12 show the $^{35}$S-translation products produced in the 2-5A-cellulose-pretreated and untreated lysates, respectively.

Ribonuclease assays with recombinant 2-5A-dependent RNase are performed after immobilizing and purifying the translation product on the activating affinity matrix, 2-5A-cellulose. It was previously shown that murine L cell 2-5A-dependent RNase bound to 2-5A-cellulose, resulting in ribonuclease activity against poly(U) but not poly(c). See Silverman, R. H., *Anal. Biochem.,* 144:450–460 (1985). Furthermore, by washing 2-5A-dependent RNase:2-5A-cellulose prior to adding the substrate the level of general, non-2-5A-dependent RNase, is greatly reduced. See Silverman, R. H., *Anal. Biochem.,* 144:450–460 (1985). Incubations of lysate in the absence of added mRNA or in the presence of both human 2-5A-dependent RNase mRNA and cycloheximide resulted in only low levels of poly(U) breakdown. See FIG. 5B. In addition, it is shown that cycloheximide completely prevented 2-5A-dependent RNase synthesis. See FIG. 5A, lane 10. In contrast, translation of the human 2-5A-dependent RNase mRNA, in the absence of inhibitor, results in substantial ribonuclease activity against poly(U) but not against poly(C). See FIG. 5B. The poly(U) is degraded with a half-life of about 10 minutes whereas only 20% of the poly(C) is degraded after one hour of incubation. Binding of recombinant 2-5A-dependent RNase to the affinity matrix was also shown by monitoring the presence of the $^{35}$S-labeled translation product. These results are believed to demonstrate that the recombinant human 2-5A-dependent RNase produced in vitro is a functional and potent ribonuclease. Furthermore, both recombinant and naturally occurring forms of 2-5A-dependent RNase are capable of cleaving poly(U) but not poly(C). See FIG. 5B. See also Silverman, R. H., *Anal. Biochem.,* 144:450–460 (1985) and Floyd-Smith, G. et al., *Science,* 212:1020–1032 (1981).

Figure 6A:
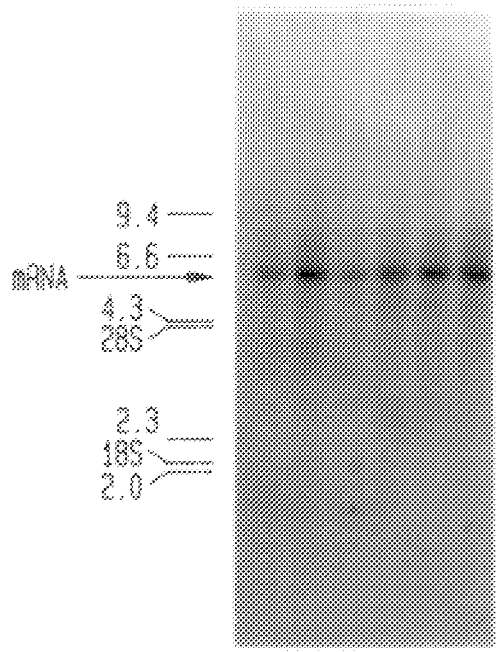
FIGS. 6A, 6B and 6C show levels of 2-5A-dependent RNase mRNA which are induced by interferon treatment of murine L929 cells even in the presence of cycloheximide.

To determine if 2-5A-dependent RNase mRNA levels are regulated by interferon, a northern blot from murine L929 cells treated with interferon and cycloheximide is probed with the radiolabeled murine 2-5A-dependent RNase cDNA. See FIG. 6. 2-5A-dependent RNase mRNA levels are enhanced three-fold by interferon ($\alpha$+$\beta$) treatment even in the presence of cycloheximide. See FIGS. 6A and B, compare lanes 1 and 2). Regulation of 2-5A-dependent RNase mRNA levels by interferon as a function of time is demonstrated (FIGS. 6A and B, lanes 3 to 6. Maximum 2-5A-dependent RNase mRNA levels are observed after 14 hours of interferon treatment. See FIGS. 6A and B, lane 6. A similar increase in levels of 2-5A-dependent RNase per se is observed after interferon treatment of the cells. Relatively invariant levels of GAPDH mRNA indicates that equivalent levels of RNA are present in every lane of the blot. See FIG. 6C. These results are believed to show that the induction of 2-5A-dependent RNase expression is a primary response to interferon treatment. The murine and human 2-5A-dependent RNase mRNAs are determined from northern blots to be 5.7 kb and 5.0 kb in length, respectively. See FIG. 6A. The 2-5A-dependent RNase coding sequences, therefore, comprise only about 40% the nucleotide sequences contained in the mRNAs.

Figure 7A:
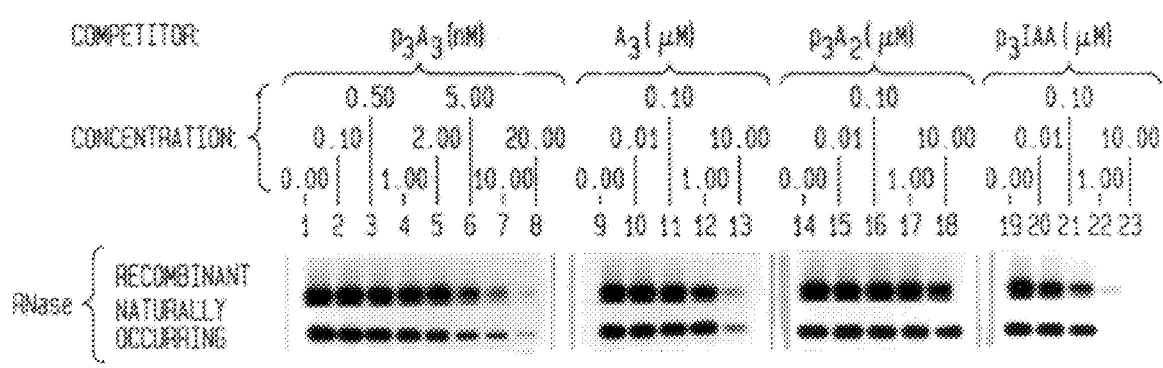
FIGS. 7A and 7B are the truncated, recombinant murine 2-5A-dependent RNase, clone ZB1, and murine L cell 2-5A-dependent RNase having identical 2-5A binding activities localized to a repeated P-loop motif.

The 2-5A binding functions of the recombinant and naturally occurring forms of murine 2-5A-dependent RNase are characterized by covalent crosslinking to the 2-5A probe in the presence of unlabeled 2-5A or 2-5A analogues as competitors. See FIG. 7A. Interestingly, although the about 74 kDa truncated 2-5A-dependent RNase is missing about 84 amino acids from its carboxy-terminus, see FIG. 4, it nonetheless possesses a 2-5A binding activity indistinguishable from that of naturally occurring 2-5A-dependent RNase. See FIG. 7A. Trimer 2-5A[$p_3$(A2'p)$_2$A], at about 20 nM effectively prevents the 2-5A probe from binding to either protein. See FIG. 7A, lane 8. In comparison, a 500-fold higher concentration of (A2'p)$_2$A (10 $\mu$M) is required to prevent probe binding to both proteins. See lane 13. The dimer species, $p_3$A2'pA, is unable to prevent the 2-5A probe from binding to the proteins even at a concentration of 10 $\mu$M (lane 18). However, the inosine analogue, $p_3$I2'pA2'pA, Imai, J. et al., *J. Biol. Chem.,* 260:1390–1393 (1985), is able to prevent probe binding to both proteins but only when added at a concentration of about 1.0 $\mu$M (lane 22).

Figure 7B:
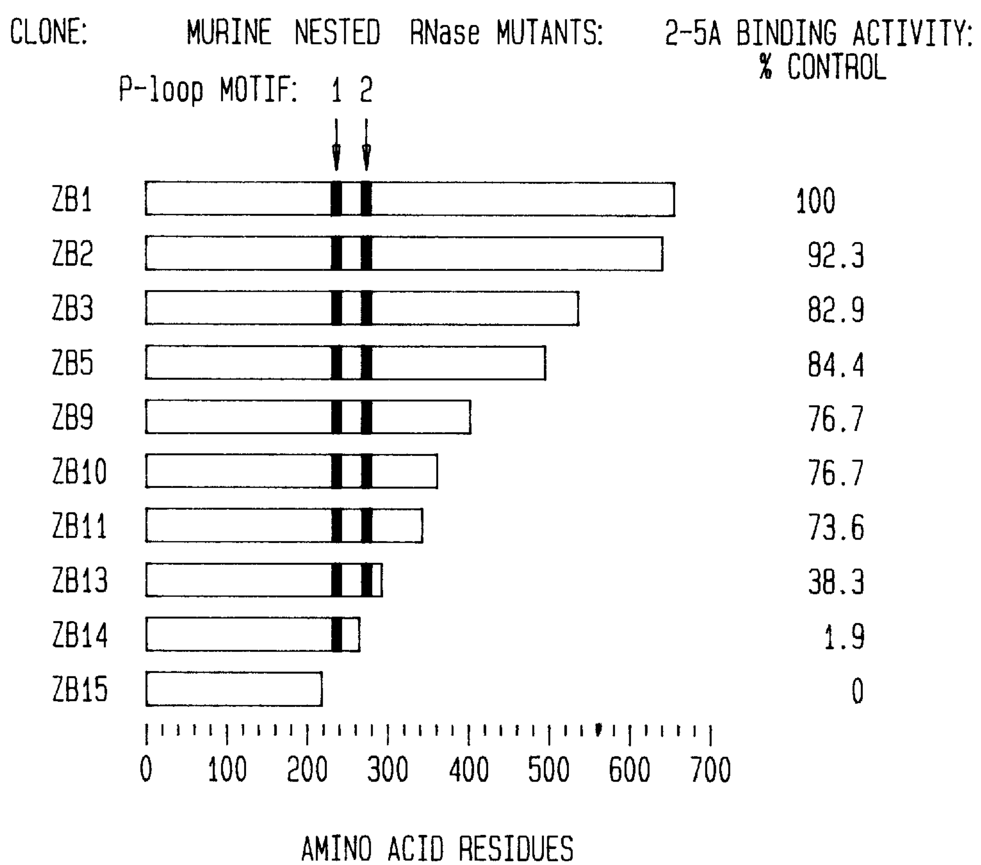

To further define sequences involved in 2-5A binding, nested 3'-deletions of the murine 2-5A-dependent RNase cDNA, clone ZB1, are constructed, transcribed in vitro, and expressed in a wheat germ extract. See FIG. 7B. The different deletion clones produce comparable amounts of polypeptide as monitored by incorporation of $^{35}$S-methionine. The levels of 2-5A binding activity are determined with the 2-5A probe in both a filter binding assay, Knight, M. et al., *Nature,* 288:189–192 (1980), and the uv crosslinking assay, Nolan-Sorden, N. L. et al., *Anal. Biochem.,* 184:298–304 (1990), with similar results. See FIG. 7B. Expression of clone ZB11, encoding amino acid residues 1 to 342, results in a loss of only about 26% of the 2-5A binding activity as compared to clone ZB1 (amino acids 1 to 656). See FIG. 7B. Clones intermediate in length between ZB1 and ZB11 all result in significant levels of 2-5A binding activity. In contrast, protein produced from ZB13 (amino acids 1 to 294) results in only about 38.3% of the 2-5A binding activity of clone ZB1, suggesting that a region important for the 2-5A binding function is affected. Indeed, clone ZB14 produced a protein encoding amino acids 1 to 265 which is nearly inactive in the 2-5A binding assay (only 1.9% of th activity of clone ZB1). Interestingly, the significant decrease in 2-5A binding activity observed with ZB14 occurs with the deletion of one of two P-loop motifs; nucleotide binding domains in many proteins. See FIGS. 4 and 7B. See also Saraste, M. et al., *TIBS,* 14:430–434 (1990). Deletion of both P-loop motifs in clone ZB15 results in protein (amino acids 1 to 218) which is completely lacking in 2-5A binding activity. See FIG. 7B.

Figure 8A:
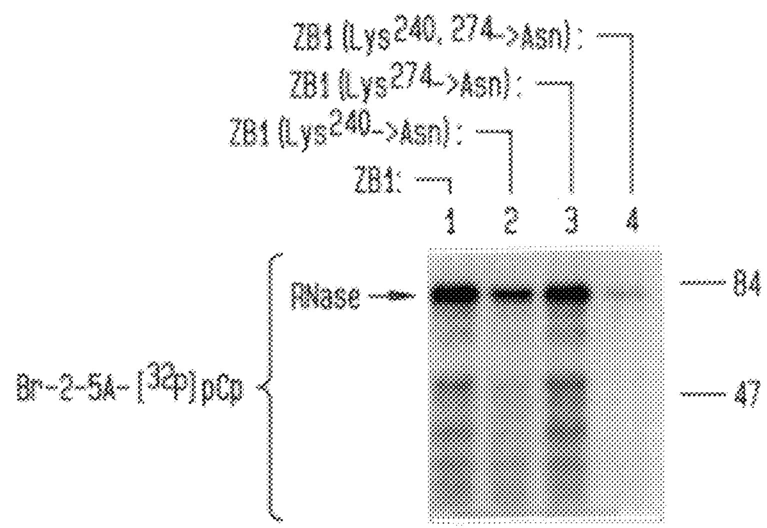
FIGS. 8A and 8B are substitution mutations of the lysine residues in the P-loop motifs of 2-5A-dependent RNase.
Figure 8B:
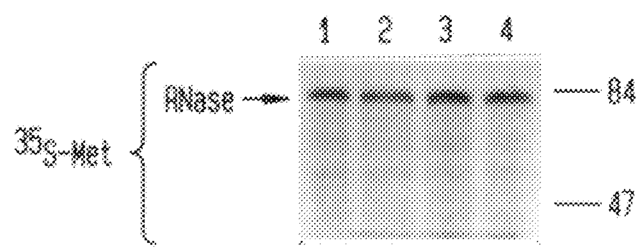

To probe the involvement of the consensus lysine residues in the P-loop motifs in 2-5A binding activity, site-directed mutagenesis is performed on the truncated form of murine 2-5A-dependent RNase encoded by clone ZB1. Previously, it is reported that substitution mutations of the conserved lysine residues in P-loop motifs of eucaryotic initiation factor 4A and for Bacillus anthracis adenylyl cyclase results in a loss of ATP binding and catalytic activities, respectively. See Rozen et al., *Mol. Cell. Biol.,* 9:4061–4063 (1989) and Xia, Z. and Storm, D. R., *J. Biol. Chem.,* 265:6517–6520 (1990). In the former study the invariant lysine residue is mutated to asparagine. See Rozen et al., *Mol. Cell. Biol.,* 9:4061–4063 (1989). We substituted, individually and together, the consensus lysines with asparagines at positions 240 and 274 in the two P-loop motifs of 2-5A-dependent RNase. See FIG. 8 and the Example. Analysis of the effects of these mutations on 2-5A binding activity is determined by covalently crosslinking the $^{32}$P-2-5A probe to the in vitro translation products under uv light. See FIG. 8A. See also Nolan-Sorden, N. L. et al., *Anal. Biochem.,* 184:298–304 (1990). Similar levels of proteins are synthesized from the different mRNA species as shown in separate reactions containing $^{35}$S-methionine. See FIG. 8B. The three mutant forms of 2-5A-dependent RNase show reduced binding to the 2-5A probe. See FIG. 8A, lanes 2 to 4. Clone ZB1 (Lys$^{240}$→Asn), FIG. 8A, lane 2, expresses a mutant 2-5A-dependent RNase with a substantially reduced affinity for 2-5A; about 48.4% of the activity of clone ZB1 as determined by phosphorimager analysis (Molecular Dynamics) of the dried gel. A more modest reduction in 2-5A binding activity, to 79% of the control value, is obtained from clone ZB1(Lys$^{274}$→Asn). See FIG. 8A, lane 3. In contrast, 2-5A binding activity from clone ZB1(Lys$^{240,274}$→Asn), FIG. 8A, lane 4, in which both conserved lysine residues are replaced with asparagine residues, is reduced to only 12.2% of the activity of clone ZB1 (averaged from three separate experiments). These results suggest that the lysine residues at positions 240 and 274 function within the context of a repeated P-loop motif in the binding of 2-5A to 2-5A-dependent RNase.

The molecular cloning and expression of 2-5A-dependent RNase, the terminal factor in the 2-5A system and a key enzyme in the molecular mechanisms of interferon action is described. See FIG. 1. The recombinant proteins produced in vitro are demonstrated to possess 2-5A binding properties identical to naturally occurring forms of murine and human 2-5A-dependent RNase. See FIGS. 2, 5A, and 7. In addition, linkage of a $^{32}$P-2-5A analogue to a truncated murine 2-5A-dependent RNase and to murine L cell 2-5A-dependent RNase followed by partial proteolysis reveals identical patterns of labeled peptides. See FIG. 2B. Furthermore, the full-length recombinant human 2-5A- dependent RNase isolated on the activating, affinity matrix, 2-5A-cellulose, shows potent ribonuclease activity towards poly(U) but none against poly(C). See FIG. 5B. Similarly, it is previously demonstrated that murine L cell 2-5A-dependent RNase was activated by 2-5A-cellulose resulting in the cleavage of poly(U), but not of poly(C). See Silverman, R. H., *Anal. Biochem.,* 144:450–460 (1985). The full-length human 2-5A-dependent RNase, which is produced in reticulocyte lysate, had the same apparent molecular weight as did naturally occurring 2-5A-dependent RNase. See FIG. 5A. However, the actual molecular mass of human 2-5A-dependent RNase is determined from the predicted amino acid sequence, FIG. 3B, to be about 83,539 Da.

Figure 1:
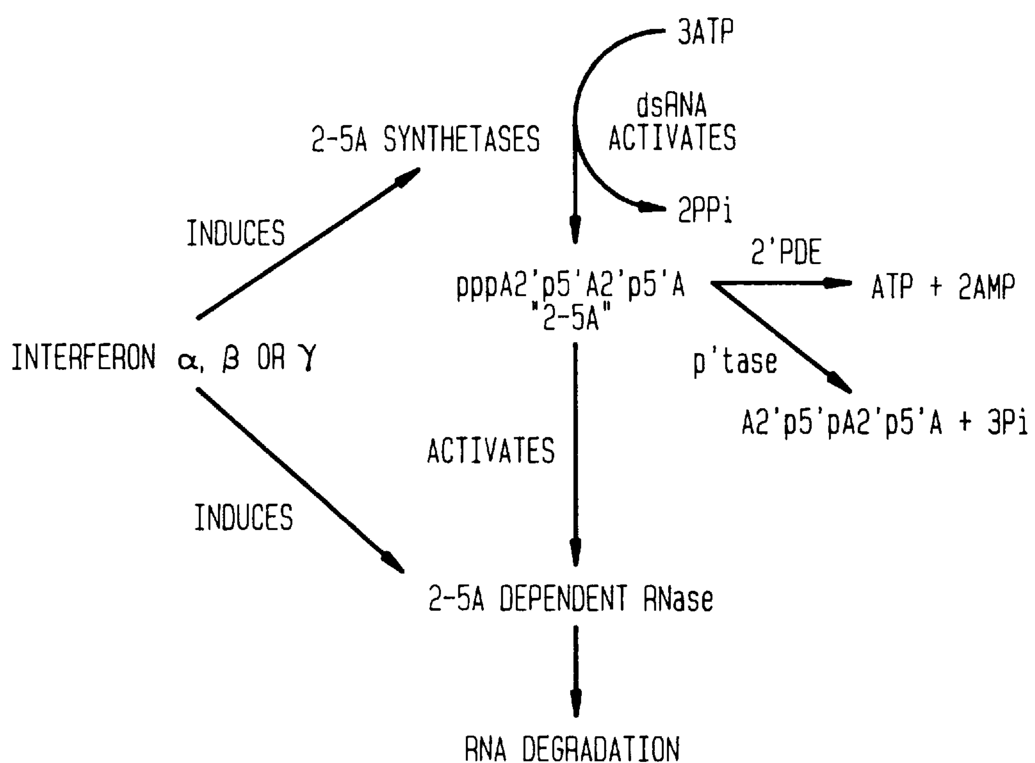
FIG. 1 is the 2-5A system: a ribonuclease pathway which is believed to function in the molecular mechanism of interferon action. 5'-phosphatase, p'tase; 2'–5'-phosphodiesterase, 2'-PDE.
Figure 6B:
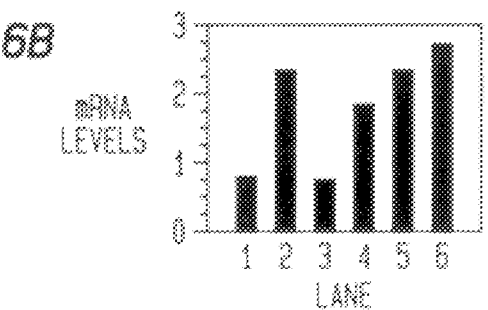
Figure 6C:
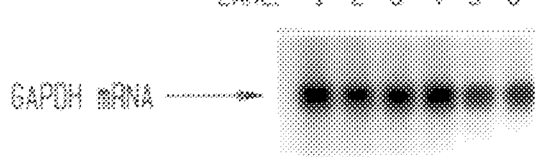
Figure 11:
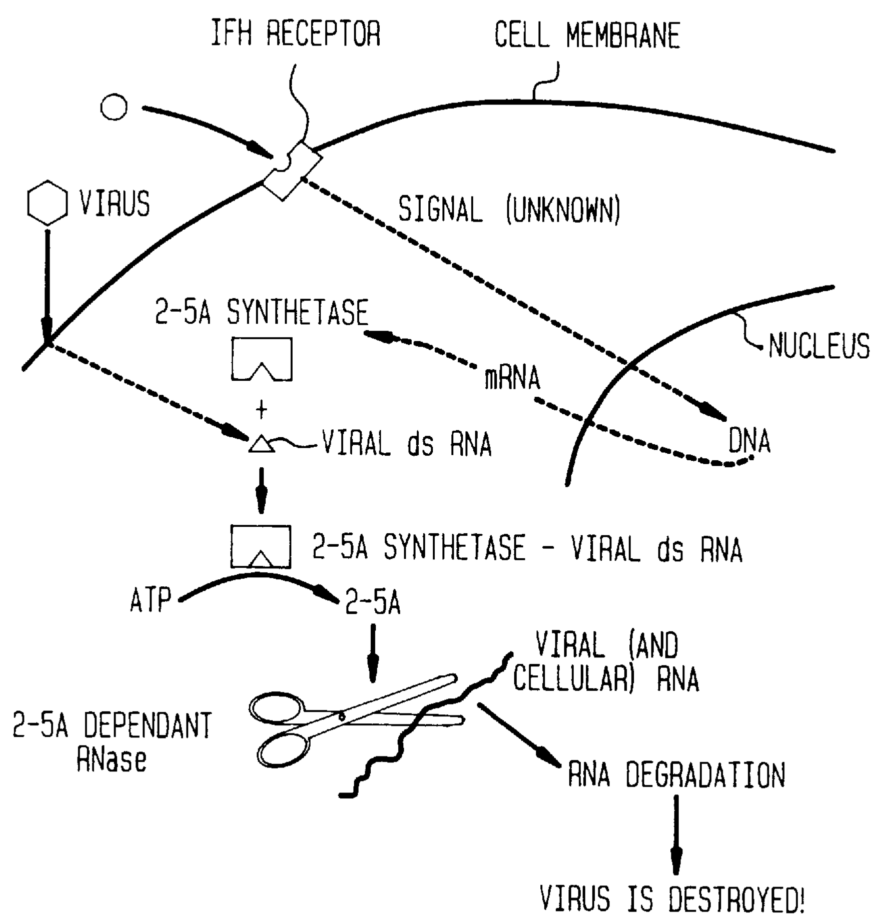
FIG. 11 shows the role of 2-5A-dependent RNase in the anti-viral response of cells to interferon treatment. Interferon binds to specific cell surface receptors resulting in the generation of a signal which activates a set of genes in the cell nucleus. The genes for 2-5A synthetase are thus activated producing inactive, native 2-5A synthetase. Interferon treatment of the cell also activates the 2-5A-dependent RNase gene (not shown in the figure). Subsequently, the interferon-treated cells is infected by a virus. The virus produces double stranded RNA (dsRNA) during its replicative cycle. The viral dsRNA then activates the 2-5A synthetase resulting in the production of 2-5A. The 2-5A then activates the 2-5A-dependent RNase to degrade the viral RNA thus destroying the virus itself.

Previously, it was reported that interferon enhances levels of 2-5A-dependent RNase by between two- to twenty-fold depending on the cell type. See Silverman, R. H. et al., *Eur. J. Biochem.,* 126:333–341 (1982b) and Jacobsen, H. et al., *Virology,* 125:496–501 (1983a). Results presented herein suggest that the gene for 2-5A-dependent RNase may be an interferon-stimulated gene. See FIG. 6. Levels of 2-5A-dependent RNase mRNA in murine L929 cells are elevated as a function of time of interferon ($\alpha+\beta$) treatment by a factor of about three. Furthermore, the induction appeared to be a primary response to interferon treatment because it is observed in the presence of cycloheximide. Therefore, interferon is believed to regulate the 2-5A pathway by elevating levels of both 2-5A synthetases, Hovanessian, A. G. et al., *Nature,* 268:537–539 (1977), and 2-5A-dependent RNase, Jacobsen, H. et al., *Virology,* 125:496–501 (1983a). See. FIGS. 1, 6 and 11.

The cloning of 2-5A-dependent RNase reveals several features of the protein. The 2-5A binding domain is of particular interest because it is the ability of 2-5A-dependent RNase to be activated by 2-5A that sets it apart from other nucleases. By expressing nested 3'-deletions of murine 2-5A-dependent RNase, a region between amino acids residues 218 and 294 which is believed to be critical for 2-5A binding activity is identified. See FIG. 7B. Interestingly, the identified region contains a repeated P-loop motif, one from residues 229 to 241 and another from residues 253 to 275. See FIG. 4 and Table II. When the latter P-loop motif (amino acids 253–275) is partially deleted, there is a precipitous decline in 2-5A binding activity. See clone ZB14 in FIG. 7B.

The homology with P-loops is believed to be highly conserved between the human and murine forms of 2-5A-dependent RNase; thus underscoring the belief of the importance of this region for 2-5A binding activity. See FIG. 4. The similarity to P-loops consists of the tripeptides, glycine-lysine-threonine, preceded by glycine-rich sequences. In this regard, the unusual feature of 2-5A-dependent RNase is that the P-loop motif is repeated and are in the same orientation. Adenylyl cyclase from Bacillus anthracis also contains a duplicated P-loop motif, however, the two sequences are in opposite orientation and are overlapping. See Xia, Z. and Storm, D. R., *J. Biol. Chem.,* 265:6517–6520 (1990).

The relative importance of the conserved P-loop lysines (at positions 240 and 274) are evaluated by site-directed mutagenesis of the murine 2-5A-dependent RNase, clone ZB1. Although individual substitution mutations of the two lysines significantly reduced 2-5A binding activity, replacing both of the lysines with asparagine residues in the same mutant RNase severely represses 2-5A binding. See FIG. 8. Perhaps the trimer 2-5A requirement for activation of most forms of 2-5A-dependent RNase could be explained if the first and third adenylyl residues of 2-5A interact with the separate P-loop sequences inducing conformational changes in 2-5A-dependent RNase. In this regard, dimer 2-5A neither binds 2-5A-dependent RNase efficiently nor does it activate 2-5A-dependent RNase, FIG. 7A; Kerr, I. M. and Brown, R. E., *Proc. Natl. Acad. Sci. U.S.A.,* 75:265–260 (1978) and Knight, M. et al., *Nature,* 288:189–192 (1980), perhaps because it is too short to span the two P-loop motifs. Alternately, the residual 2-5A binding activity observed in the point mutants, ZB1(Lys$^{240}$→Asn) and ZB1 (Lys$^{274}$→Asn), and the very low affinity of the double mutant, ZB1(Lys$^{240,274}$→Asn) for 2-5A, could indicate that the two P-loop motifs are parts of separate 2-5A binding domains.

Homology with protein kinase domains VI and VII is also identified in 2-5A-dependent RNase. See FIG. 4. See also Hanks, S. K. et al., *Science,* 241:42–52 (1988). Although domain VI is believed to be involved in ATP binding, this region in 2-5A-dependent RNase is believed not to be important for 2-5A binding because its deletion caused only a minimal reduction in affinity for 2-5A. See FIG. 7B. However, a modest (two-fold) stimulatory effect of ATP on 2-5A-dependent RNase activity has been reported. See Wreschner, D. H. et al., *Eur. J. Biochem.,* 124:261–268 (1982) and Krause, D. et al., *J. Biol. Chem.,* 261:6836–6839 (1986). The latter report indicated that ATP was not required for 2-5A-dependent RNase activity but may act to stabilize the enzyme. Therefore, the region of homology with protein kinases could perhaps bind ATP resulting in stimulation of ribonuclease activity through stabilization of the enzyme.

A consensus zinc finger domain, reviewed in Evans, R. M. and Hollenberg, S. M., *Cell,* 52:1–3 (1988), consisting of six cysteine residues with the structure IDS SEQ NO: 8 $CX_4CX_3CX_{17}CX_3CX_3C$ (SEQ ID NO: 7 which corresponds to amino acid residues 401–436 in Table II) is identified in the murine form of 2-5A-dependent RNase. See FIG. 4. The homologous region in the human form of 2-5A-depenent RNase is $CX_{11}CX_{25}CX_3CX_6C$ (SEQ ID NO: 8 which corresponds to amino acid numbers 395 to 444 in Table I). Because zinc fingers are nucleic acid binding domains, the cysteine-rich region in 2-5A-dependent RNase could be involved in binding to the RNA substrate. Alternatively, the cysteine-rich domain in 2-5A-dependent RNase could mediate formation of 2-5A-dependent RNase dimers. Analysis of crude preparations of 2-5A-dependent RNase suggest that 2-5A-dependent RNase may form dimers in concentrated but not in dilute extracts. See Slattery, E. et al., *Proc. Natl. Acad. Sci. U.S.A.,* 76:4778–4782 (1979) and Wreschner, D. H. et al., *Eur. J. Biochem.,* 124:261–268 (1982).

Comparison between the amino acid sequences of other ribonucleases with 2-5A-dependent RNase identifies some limited homology with RNase E, an endoribonuclease from *E. coli* . See FIG. 9A. See also Apirion D. and Lassar, A. B., *J. Biol. Chem.,* 253:1738–1742 (1978) and Claverie-Martin, F. et al., *J. Biol. Chem.* 266:2843–2851 (1991). The homology with RNase E is relatively conserved between the human and murine forms of 2-5A-dependent RNase and spans a region of about 200 amino acid residues. Within these regions there are 24 and 32% identical plus conservative matches, with some gaps, between RNase E and the human and murine forms of 2-5A-dependent RNase, respectively. See FIG. 9A. The rne gene which encodes RNase E and the altered mRNA stability (ams) gene, Ono, M. and Kumano, M., *J. Mol. Biol.,* 129:343–357 (1979), map to the same genetic locus. See Mudd E. A. et al., *Mol. Microbiol.,* 4:2127–2135 (1990); Babitzke, P. and Kushner, S. R., *Proc. Natl. Acad. Sci. U.S.A.,* 88:1–5 (1991) and Taraseviciene, L. et al., *Mol. Microbiol.,* 5:851–855 (1991). RNase E is required for both efficient mRNA turnover and rRNA processing in *E. coli.* See Mudd E. A. et al., *Mol. Microbiol.,*

4:2127–2135 (1990) and Babitzke, P. and Kushner, S. R., *Proc. Natl. Acad. Sci. U.S.A.,* 88:1–5 (1991). The cleavage specificities of 2-5A-dependent RNase and RNase E are similar in that 2-5A-dependent RNase cleaves mainly after UU or UA, Wreschner, D. H. et al., *Nature,* 289:414–417 (1981a) and Floyd-Smith, G. et al., *Science,* 212:1020–1032 (1981), and RNase E usually cleaves within the central AUU sequence of (G or A)AUU(A or U), Ehretsmann, C. P. et al., *Genes & Development,* 6:149–159 (1992). The location of the RNase E homology and other identified features in 2-5A-dependent RNase are shown. See FIG. 9B. These findings raise the possibility that RNase E may be the ancestral precursor of 2-5A-dependent RNase. In this regard, there are indications of 2',5'-oligoadenylates in *E. coli* . See Brown, R. E. and Kerr, I. M., *Process in Clinical and Biological Research,* 202:3–10 (1985) and Trujillo, M. A. et al., *Eur. J. Biochem.,* 169:167–173 (1987). However, the evolutionary distribution of a complete 2-5A system (i.e. 2-5A synthetase and 2-5A-dependent RNase) is reported to begin only with reptiles or possibly amphibia. See Cayley, P. J. et al., *Biochem. Biophys. Res. Commun.,* 108:1243–1250 (1982).

Endoribonucleases play a controlling role in RNA metabolism by catalyzing the rate-limiting steps in RNA decay. See Brawerman, G., *Cell,* 57:9–10 (1989). 2-5A-dependent RNase is a uniquely regulated endoribonuclease which mediates effects of interferon against picornaviruses. It functions by binding 2-5A and subsequently degrades both viral and cellular RNA. See Wreschner, D. H. et al., *Nucleic Acids Res.,* 9:1571–1581 (1981b). In addition, the 2-5A system may be involved in the antiproliferative effects of interferon and in the fundamental control of RNA stability. Cellular levels of 2-5A-dependent RNase and/or 2-5A-synthetase are regulated during interferon-treatment, Hovanessian, A. G. et al., *Nature,* 268:537–539 (1977) and Jacobsen, H. et al., *Virology,* 125:496–501 (1983a), cell growth arrest, Stark, G. et al., *Nature,* 278:471–473 (1979) and Jacobsen, H. et al., *Proc. Natl. Acad. Sci. U.S.A.,* 80:4954–4958 (1983b), cell differentiation, Krause, D. et al., *Eur. J. Biochem.,* 146:611–618 (1985), changing hormone status, e.g., Stark, G. et al., *Nature,* 278:471–473 (1979), and liver regeneration, Etienne-Smekens, M. et al., *Proc. Natl. Acad. Sci. U.S.A.,* 80:4609–4613 (1983). However, basal levels of 2-5A-dependent RNase and 2-5A synthetase are present in most if not all mammalian cells. The existence of multiple forms of 2-5A synthetase with different intracellular locations, Hovanessian, A. G. et al., *EMBO J.,* 6:1273–1280 (1987), could indicate diverse functions for the 2-5A system. Similarly, the ubiquitous presence of the 2-5A system in higher animals suggests an important function for 2-5A-dependent RNase, Cayley, P. J. et al., *Biochem. Biophys. Res. Commun.,* 108:1243–1250 (1982). For instance, 2-5A-dependent RNase cleaves rRNA at specific sites in intact ribosomes, Wreschner, D. H. et al., *Nucleic Acids Res.,* 9:1571–1581 (1981b) and Silverman, R. H. et al., *J. Virol.,* 46:1051–1055 (1983), possibly affecting translation rates. The transient nature of 2-5A, Williams, B. R. G. et al., *Eur. J. Biochem.,* 92:455–562 (1978), and its growth inhibitory effect after introduction into cells, Hovanessian, A. G. and Wood, J. N., *Virology,* 101:81–89 (1980), indicate that the 2-5A system is a tightly regulated pathway.

Figure 12:
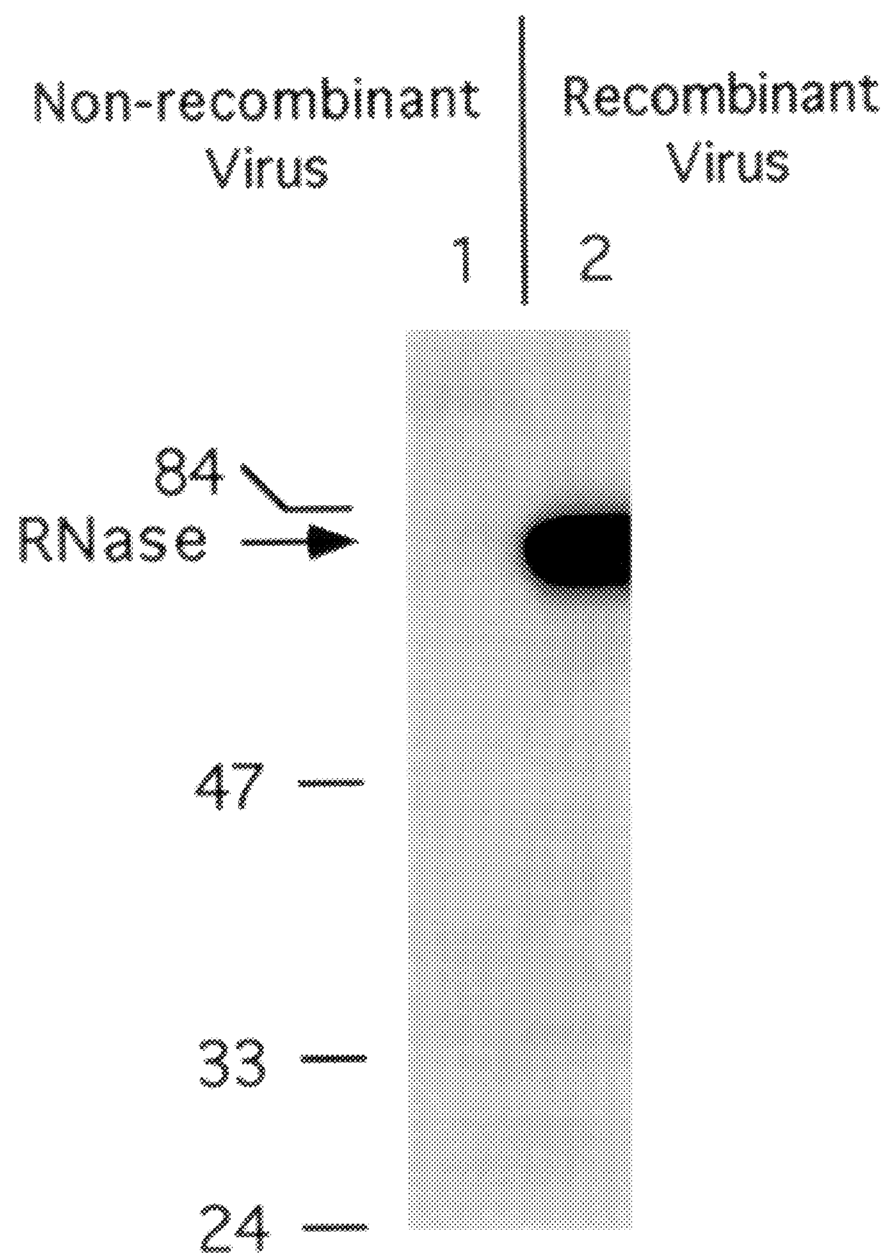
FIG. 12 shows recombinant baculovirus produced 2-5A-dependent RNase in infected SF21 cells as determined by an affinity labeling method (Nolan-Sorden supra et al., 1990). Crude extract containing 150 $\mu$g of protein were from SF21 cells infected with non-recombinant virus (lane 1) or with recombinant virus containing cDNA to 2-5A-dependent RNase (clone ZC5). The 2-5A probe (60,000 counts per minute per assay) was incubated with the cell extracts for one hour at 4° C.
Figure 13:
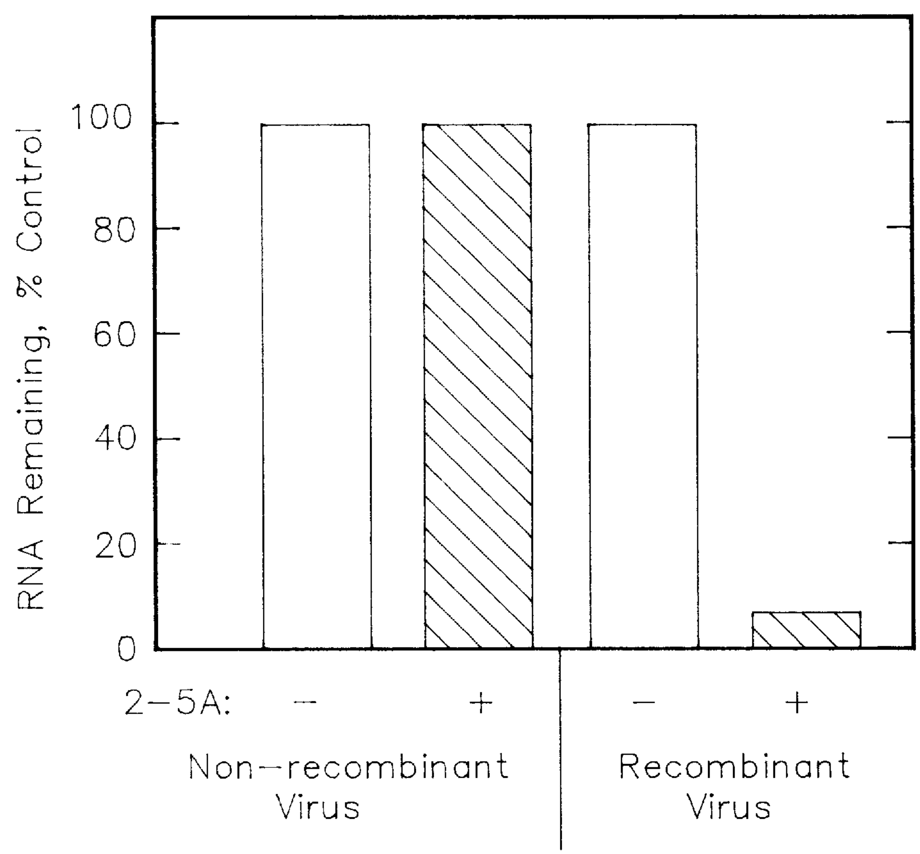
FIG. 13 shows an extract of insect cells infected with recombinant virus but not with nonrecombinant virus expressed 2-5A-dependent RNase activity against poly(rU). Crude cell extracts, containing 2 $\mu$g of protein, were incubated with 12 nM poly(rU)-$^{32}$p[Cp] for 30 minutes at 30° C. in the presence of absence of 100 nM of tetramer 2-5A. RNA degradation was determined by measuring acid-insoluble fraction of RNA as described (Silverman, R. H. *Anal. Biochem.,* 144:450–460 1985).

Also in accordance with the present inventory the human form of the 2-5A dependent RNase has been expressed in insect cells. The baculovirus system allows expression in a cell type containing no endogenous 2-5A-dependent RNase (FIGS. 12 and 13). In addition, the 2-5A-dependent RNase which was produced is soluble and fully functional with respect to both 2-5A binding and catalytic activities. Furthermore, high levels of 2-5A-dependent RNase can now be produced, at least about 10% of the total soluble protein in the cells. The recombinant 2-5A-dependent RNase elute from a gel filtration column as a monomer which have full activity (FIG. 15). Therefore, although it was proposed that 2-5A-dependent RNase is a dimer of 2-5A binding and catalytic subunits (Salehzada et al., 1993), this is not the case (Zhou, A., et al., *Cell,* 72:753–765 (1993); Hassel, B. A., et al., *Embo J.* 12:3297–3304 (1993); and FIGS. 12 to 15). The 2-5A-dependent RNase is in its "off-state" in the absence of 2-5A and it is converted to its "on-state" after addition of 2-5A (FIGS. 15 to 18).

The lack of activation ability of the diner, ppp5'A2'p5'A, and the equivalent potencies of the trimer, tetramer, and pentamer 2-5A triphosphates (FIG. 16), imply the need for three adenosine nucleotide residues for maximal nuclease activation, in accord with previous findings using crude enzyme sources (Kerr and Brown, 1978; Martin et al., 1979; Knight et al., 1980, 1981; Drocourt et al., 1982; Torrence et al., *J. Med. Chem.* 27, 726–783 1984). It is likely, however, that elements of the third or 2'-terminal adenosine residue, may be dispensable for limited, albeit not optimal, nuclease activation (Drocourt et al., 1982; Imai, J. et al., *J. Ord. Chem.* 50, 1418–1420 1985; Torrence et al., 1986, 1988; Kitade et al., 1991; Kovacs et al., 1993).

Figure 16A:
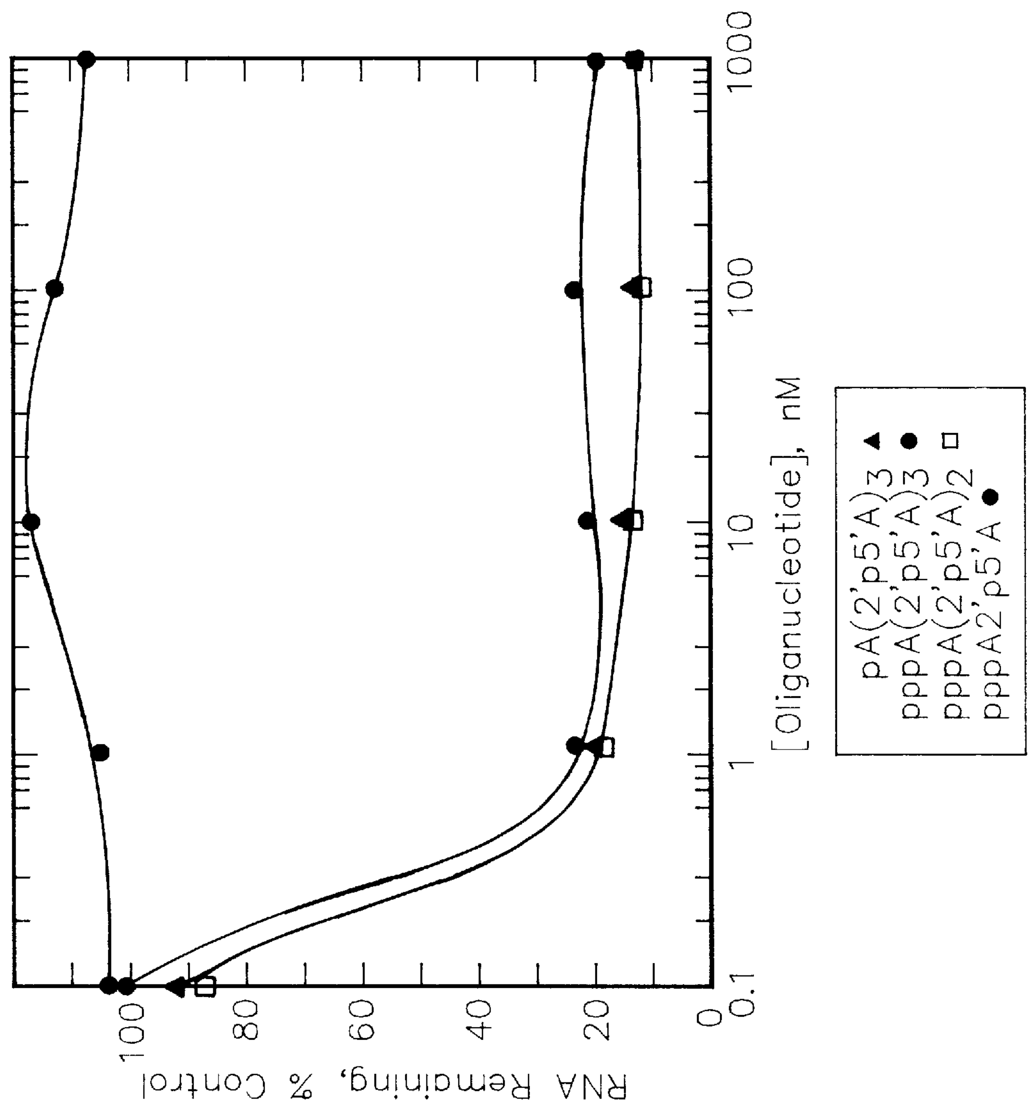
FIGS. 16A, 16B and 16C show the activator requirements of 2-5A-dependent RNase. Assays were with 50 ng of superose 12 purified fractions of the 2-5A-dependent RNase at 30° C. for 30 minutes using 12 nM poly(rU)-$^{32}$P[Cp] as substrate.

FIG. 16A records a difference between the activation requirements of the human-derived 2-5A-dependent RNase and the mouse cell-derived enzyme; that is, the ability of the 5'-monophosphorylated 2',5'-oligoadenylates to activate the human RNase (Haugh et al, 1983; Kinjo et al, 1992; Kovacs et al, 1993) as contrasted to the need for a 5'-di- or 5'-triphosphate, which in some cases may be equivalent (Lesiak and Torrence, 1985), to activate most preparations of mouse enzymes (reviewed by Johnston and Torrence, 1984) (but see Haugh et al, 1983). With certain 2-5A analogues, the apparent need for a 5'-polyphosphate to activate the mouse 2-5A-dependent RNase has been obviated by appropriate base modifications (Krause et al, 1986; Lesiak , K. et al., *J. Biol. Chem.* 262, 1961–1965 (1985); and 1987; Torrence et al, 1992) which modulate the glycosidic torsion angle (Van Den Hoogen et al, 1989).

Figure 16B:
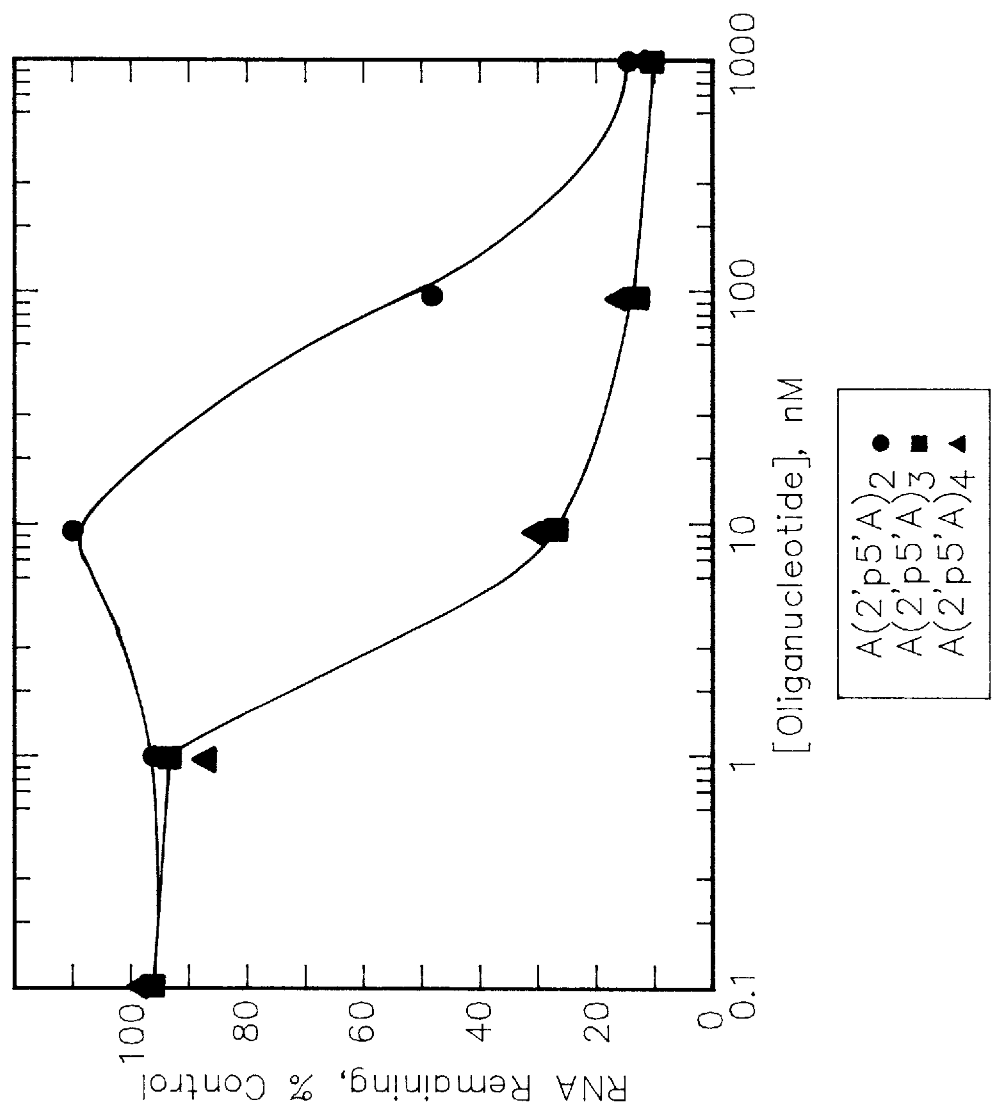

It has also been documented (Kerr and Brown, 1978; Martin et al., 1979; Knight et al., 1980, 1981; Drocourt et al., 1982; Torrence, P. F. et al., *J. Med. Chem.* 27, 726–733 1984) that removal of the 5'-phosphate of 2-5A trimer 5'-monophosphate leads to 100- to 1000-fold loss of 2-5A-dependent RNase binding. On the other hand, tetramer, pentamer, and hexamer cores were bound to the RNase only 7–10 times less effectively than the corresponding 5'-monophosphates. FIG. 16B, however, suggests that with the cloned and purified human enzyme, such longer 2-5A core oligomers may activate the 2-5A-dependent RNase, albeit less effectively than the 5'-phosphorylated species. It has been suggested (Torrence, P. F. et al, *J. Med. Chem.* 27, 726–733 1984) that the first internucleotide bond of the longer oligomers may "slip" into the binding site for the 5'-monophosphate group, thereby providing increased binding affinity over the trimer core. A similar scenario may be invoked to explain the enhanced activity of $A(2'p5'A)_3$ and $A(2'p5'A)_4$ as compared to $A(2'p5'A)_2$ with the purified human enzyme (FIG. 16).

The phosphodiester linkage isomer of 2-5A trimer, 3–5A $[ppp5'A(3'p5'A)_2]$, was without activity as an activator of the 2-5A-dependent RNase (FIG. 16C), thereby confirming the earlier results with crude mouse L cell enzyme as well as partially purified mouse L cell and Ehrlich ascites cell enzyme (Lesiak, K. et al, *J. Biol. Chem.* 258, 13082–13088 1983; Krause et al, 1986). An earlier study (Lesiak, K. et al, *J. Biol. Chem.* 258, 13082–13088 1983) suggested that the lack of 2-5A-dependent activation ability of 3–5A was due to a 10,000-fold decrease in binding of 3–5A by the endonuclease. This discrimination ability could be critical in a biological sense since substantial affinity of the 2-5A-dependent RNase for consecutive 3',5'-phosphodiester-linked oligoadenylates in cellular RNA could sequester the limited amounts of enzyme in the cell, affecting its distribution, and even prevent its activation by 2-5A by the law of mass action. The decrease in RNase interaction relative to 2-5A itself could be a consequence of disturbance of the ribose-backbone and the resultant displacement of base and sugar functional groups involved in recognition (vide infra). Alternatively, or in addition, it has been established that 2',5'-oligonucleotides differ from their more common 3',5'-isomers in conformational parameters such as increased base stacking (Doornbos et al, 1981, 1983; Van Den Hoogen et al, 1989; Kondo et al, 1970) which results in a more compact molecule, and ribose pucker which also alters backbone structure (Doornbos et al, 1981, 1983; Van Den Hoogen et al, 1989; White et al, 1987).

Figure 16C:
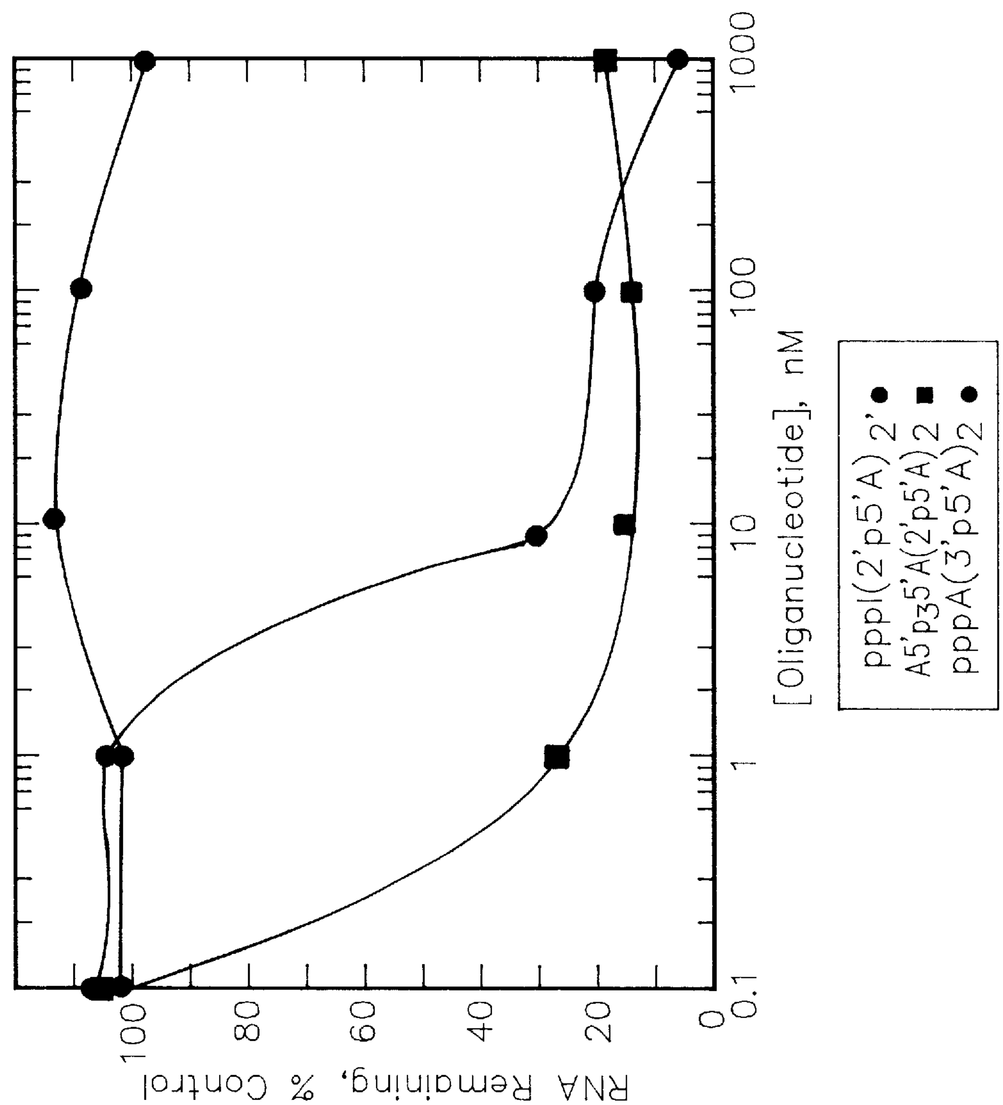

In addition, FIG. 16C suggests that the "capped" 2-5A derivative, A5'pppp5'A(2'p5'A)$_2$, is about equipotent with unmodified 2-5A trimer triphosphate as an RNase activator. Moreover, it is believed that the adenosine "capped" tetraphosphate itself is able to activate the 2-5A-dependent endonuclease, since there is no degradation to yield AMP and ppp5'A(2'p5'A)$_2$. Still further, FIG. 16C suggests that the inosine-substituted analogue ppp5'I(2'p5'A)$_2$ is more than ten-fold less effective as an activator of the 2-5A-dependent endonuclease.

Figure 17:
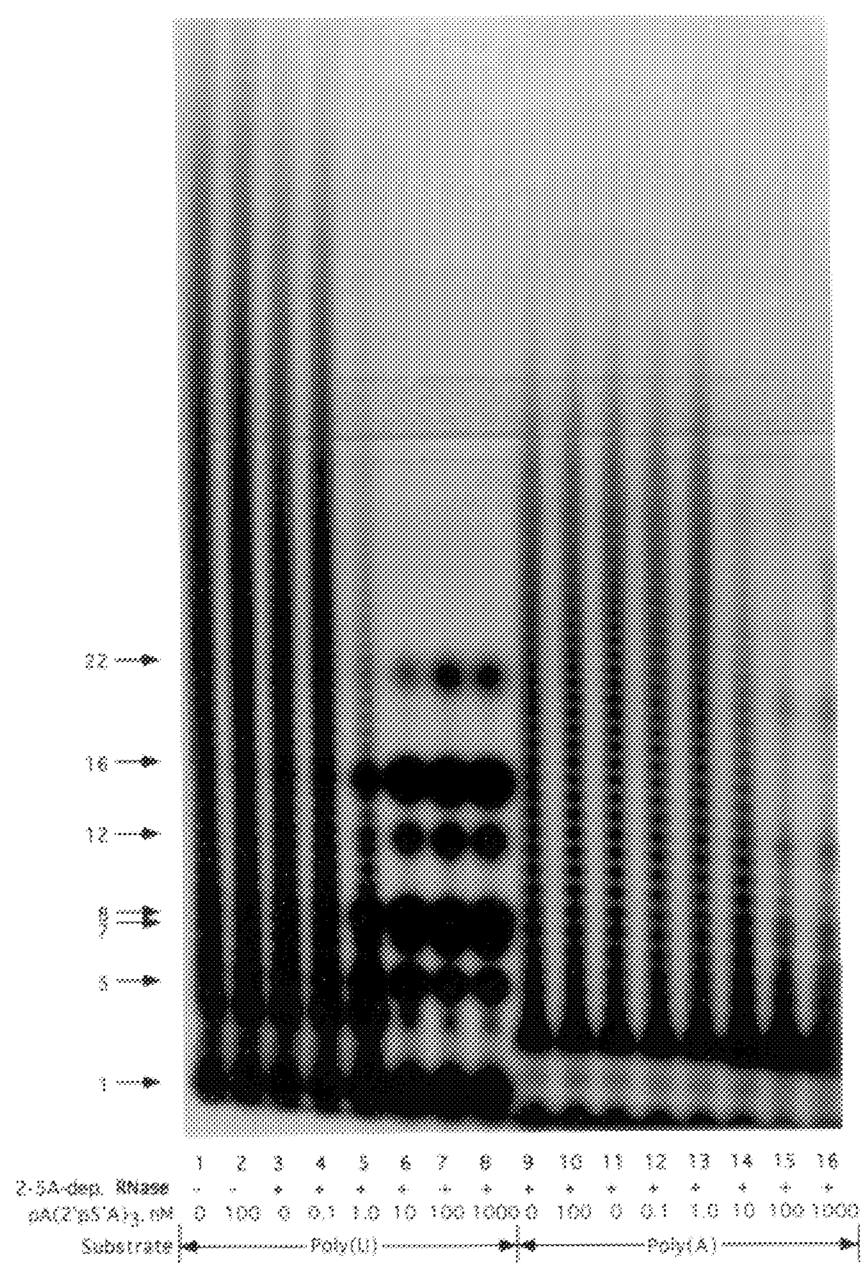
FIG. 17 shows that 2-5A-dependent RNase produces discrete cleavage products from poly(rU) and poly(rA). Assays are with 50 ng of post-superose 12 fraction of 2-5A-dependent RNase were 60 nM of poly(rU)-$^{32}$P[Cp] or of poly(rA)-$^{32}$P[Cp] for 15 minutes at 30° C. The RNA products were separated on an 8% polyacrylamide/urea sequencing gel. The autoradiogram was from x-ray film exposed to the gel for four hours.
Figure 18:
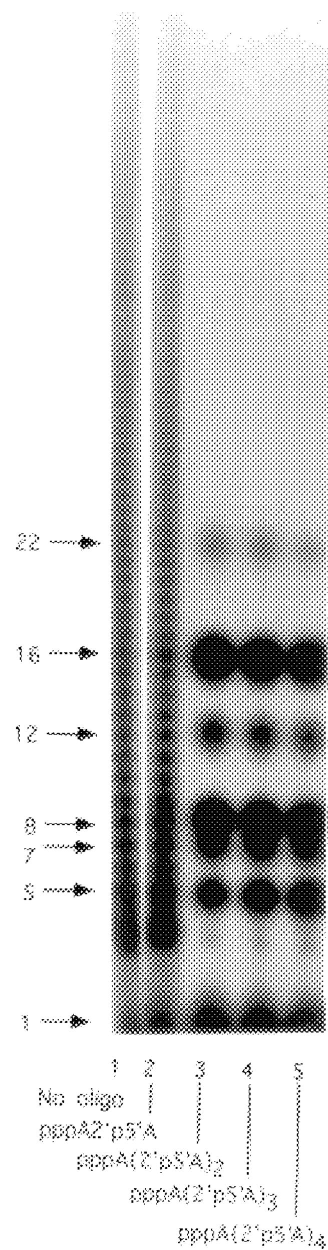
FIG. 18 shows that oligonucleotide lengths of cleavage products obtained by 2-5A-dependent RNase digestion of poly(rU) were independent of the 2-5A oligomer length. Post-superose 12 fraction of 2-5A-dependent RNase (100 ng per assay) were incubated in the presence or absence of 100 nM of different oligomers of 2-5A (indicated) for 15 minutes at 300° C. An 8% polyacrylamide/urea gel was run and exposed to film for four hours.

Previous studies on the sequence specificity of 2-5A-dependent RNase indicated that cleavage occurred after UpNp sequences in natural RNAs and within poly(rU) but not in poly(rA), poly(rG), or poly(rC) (Wreschner et al., 1981b; and Floyd-Smith et al., 1981). The poly(rU) and to a lesser extent poly(rA) are, however, believed to be substrates for 2-5A-dependent RNase. Thus, the 2-5A-dependent RNase is believed to be capable of cleaving after adenylyl residues in RNA even these are not preceded by uridylyl residues. Moreover, degradation of poly(rU) and poly(rA) produce cleavage products of discrete sizes, ranging from 5 to 22 nucleotides in lengths (FIGS. 17–18). The discrete cleavage products are not believed to be due to protection of the substrates owing to hybridization with 2-5A, because poly(rA) is also cleaved to discrete products and the size distribution of poly(rU) cleavage products is unaffected by 2-5A oligomer lengths (FIG. 9). The reason for product size distribution is unknown. However, the discrete cleavage products may be unable to bind to the active site of 2-5A-dependent RNase. Rejection of the discrete oligo(rU) fragments by the enzyme could reflect the spatial relationship between the substrate binding site and the catalytic domain.

The 2-5A-dependent RNase is believed to be capable of cleaving RNA in response to 2-5A even in the absence of divalent cations. However, both manganese and magnesium, but not calcium stimulated 2-5A-dependent RNase activity whereas zinc was inhibitory. The reason for the enhanced ribonuclease activity in the presence of manganese and magnesium is likely the result of increased 2-5A binding. However, zinc and calcium also enhanced 2-5A binding but did not enhance ribonuclease activity.

While the stimulation 2-5A-dependent RNase activities by ATP was previously observed using crude enzyme preparations (Wreschner, D. H. et al., *Nucleic Acids Res.* 9, 1571–1581 1981 and Krause et al., 1986), we have discovered that the ATP effects are believed to be due to direct stimulation of both 2-5A-binding and 2-5A-dependent RNase activities. An apparent ATP binding domain in common with protein kinases was previously observed in the predicted amino acid sequence of 2-5A-dependent RNase (Zhou et al., 1993). Perhaps binding of ATP to the enzymes enhances the ribonuclease activity owing to its increased affinity for 2-5A.

As discussed above, 2-5A-dependent RNase is a component of the interferon-regulated 2-5A system that functions in the antiviral and antiproliferative activities of interferons. Interferon treatment of cells results in enhanced levels of both 2-5A-dependent RNase and a group of synthetases that produce 5'-triphosphorylated, 2',5'-oligoadenylates (2-5A) from ATP. The 2-5A-synthetases are stimulated by double-stranded RNA (dsRNA), a frequent product of virus infection. 2-5A activates 2-5A-dependent RNase, resulting in the cleavage of viral and cellular single-stranded RNAs 3' of UpAp and UpUp. Levels of 2-5A-dependent RNase and/or 2-5A-synthetase vary with growth conditions, hormone status, liver regeneration, and cell differentiation, thus suggesting a possible wider role for the 2-5A system in the general control of RNA decay. The recent molecular cloning of the human and murine forms of 2-5A-dependent RNase revealed a repeated phosphate binding loop motif, homology with protein kinases, zinc fingers, and *Escherichia coli* RNase E, and the presence of nine ankyrin repeats implicated in mediating protein-protein interactions. The role of the 2-5A system in the control of viral and cellular growth suggests that defects in the 2-5A-dependent RNase (RNS$_4$) gene could result in reduced immunity to virus infections and cancer, thus underscoring the importance of determining the position of the RNS$_4$ gene in the human genome. There, we have localized the human gene for 2-5A-dependent RNase (RNA$_4$) by fluorescence in situ hybridization to chromosome lq25.

The regional assignment of the RNS$_4$ gene was determined by fluorescence in situ hybridization (FISH) following published methods, using a genomic 2-5A-dependent RNase clone previously isolated from a human placenta cosmid library in vector pWE15. The clone contained about 34 kb of genomic DNA, including at least 85% of the coding sequence for 2-5A-dependent RNase from the 5'-end as determined by DNA sequencing. Analysis of 30 well-spread metaphases revealed the presence of positive hybridization signals at chromosome band lq25 on all four chromatids in 25 cells and three chromatids in the remaining cells. Part of a representative metaphase preparation is shown to indicate the position of the RNS$_4$ gene. FISH signals that are visible as yellow fluorescent spots are present on all four chromatids at band lq25 of chromosome 1. The band assignment was determined by measuring the fractional chromosome length and by analyzing the banding pattern generated by the DAPI (-counterstained image. The banded chromosome 1 is shown together with a schematic idiogram to indicate that the RNS$_4$ gene probe hybridizes to band lq25. Because the genes for the small forms of 2-5A-synthetase have been mapped to human chromosomes 11 and 12, the genes for the enzymes in the 2-5A system do not appear to form a gene cluster in the human genome. Similarly, the gene for the interferon-induced, dsRNA-dependent protein kinase (PRKR) also maps to a different location, namely human chromosome 2p21-p22.

Currently, there is not direct evidence to indicate that defects in the RNS$_4$ gene result in any known disease.

However, several abnormalities that colocalize with the $RNS_4$ gene have been mapped to the region of human chromosome lq. For instance, a patient with an interstitial deletion in the long arm of chromosome 1, between lq23 and lq25, suffered from developmental delays and multiple congenital abnormalities. The Charcot-Marie-Tooth disease (hereditary motor and sensory neuropathy) ($CMT_1B$) locus has also been localized to chromosome lq21.2 to lq25, mapping near the $RNS_4$ gene. Furthermore, abnormalities in chromosome lq have been frequently observed in human cancers. For example, allele loss on chromosome lq was associated with the progression of well-differentiated, gastric adenocarcinoma, and band lq25 has been noted as one of several translation breakpoints associated with oral squamous cell carcinomas. In addition, various anomalies in the long arm of chromosome 1 were observed in lymphocyte cultures from breast cancer patients. Interestingly, allelic deletion of lq23–lq32 was correlated to breast carcinomas in 23–26% of the cases that were analyzed. Accordingly, it was suggested that inactivation of a gene between chromosome lq23 and lq32 may lead to the development of breast cancer. Because of the proposed negative growth regulatory function of 2-5A-dependent RNase, including its involvement in the antiproliferative activity of interferon, the $RNS_4$ gene may be considered as a candidate for such a tumor-suppressor gene.

EXAMPLE I

The source of mRNA for preparing the cDNA library is murine L929 cells grown in EMEM (Whittaker, Inc.) and supplemented with about 10% FBS (Gibco-BRL), and antibiotics. The cells are treated with about 50 $\mu$g per ml of cycloheximide and 1000 units per ml of murine interferon ($\alpha+\beta$) ($1.3\times10^7$ units per mg protein: Lee Biomolecular) for about 2.5 hours to increase levels of 2-5A-dependent RNase mRNA. Total RNA was then isolated, e.g. Chomczynski, P. and Sacchi, N., *Anal. Biochem.,* 162:156–159 (1987), from which poly$(A)^+$ RNA is prepared by oligo(dT)-cellulose chromatography as described. See Sambrook, J. et al., *Cold Spring Harbor Laboratory Press* (1989). Synthesis of the first strand of cDNA is done by using reverse transcriptase as described (Superscript; BRL) except that 5-methyl-dCTP is substituted for dCTP and an XhoI-oligo-dT adapter-primer (Stratagene) is used. Synthesis of the second strand of cDNA and ligation of EcoRI linker was as described (Stratagene). The cDNA is digested with EcoRI and XhoI and unidirectionally cloned into predigested λZAPII vector (Stratagene). The library is packaged by using Gigapack Gold extract and titered on PLK-F bacteria.

The cDNA library is screened directly without prior amplification at a density of about 25,000 phage per 150 mm plate. Phage are grown for 3.5 hours at about 42° C. until plaques are visible. Nitrocellulose filters saturated in IPTG (10 mM) and then dried, are overlaid on the plates and growth was continued for an additional 4 to 6 hours at 37° C. The filters are processed by a modification of the methods of Singh, H. et al., *Cell,* 52:415–423 (1988) and Singh, H. et al., *BioTechniques,* 7:252–261 (1989). Filters are washed in ice-cold binding buffer (about 20 mM Tris-HCl, about pH 7.5, about 20 mM magnesium acetate, about 50 mM potassium chloride, about 1 mM EDTA, about 50 mM β-mercaptoethanol, about 0.1 mM PMSF, about 5% glycerol) containing about 6M guanidine-HCl for about 20 min. The solution containing the filters is then diluted two-fold with binding buffer and washing on ice is continued for about an additional 5 minutes; serial two-fold dilutions were continued until the guanidine concentration was about 187 mM. The filters are then washed twice with binding buffer, and incubated with binding buffer containing about 5% nonfat milk for one hour at about room temperature. The filters are then washed twice with binding buffer and incubated in binding buffer (supplemented with about 0.25% nonfat dry milk and about 0.02% sodium azide) containing $p(A2'p)_2(br^8A2'p)_2A3'$-[32P]Cp (the "2-5A probe"), Nolan-Sorden, N. L. et al., *Anal. Biochem.,* 184:298–304 (1990), at about $2\times10^5$ counts per minute per ml (about 3,000 Ci per mmole) at about 4° C. with shaking for about 24 hours. The filters are washed twice with binding buffer and then twice with water before air drying and exposing to film.

Murine L929 cells are treated with about 1000 units per ml interferon ($\alpha+\beta$) with or without about 50 $\mu$g per ml of cycloheximide and the total RNA is then isolated as described. See Chomczynski, P. and Sacchi, N., *Anal. Biochem.,* 162:156–159 (1987). Poly$(A)^+$ RNA is prepared by oligo(dT)-cellulose chromatography, as described in Sambrook, J. et al., *Cold Spring Harbor Laboratory Press* (1989), and is separated on glyoxal agarose gels and transferred to Nytran membranes. RNA is immobilized on the membrane by uv crosslinking (Stratalinker, Stratagene). The murine 2-5A-dependent RNase cDNA is $^{32}$P-labeled by random priming and then hybridized to the filter [about 50% formamide, about 10% dextran sulphate, Denhardt's solution about 1% SDS, 6X SSPE, Sambrook, J. et al., *Cold Spring Harbor Laboratory Press* (1989), about 250 $\mu$g per ml salmon sperm DNA] at about 42° C.

The Human 2-5A-dependent RNase cDNA clone, HZB1 , is isolated from an adult human kidney cDNA library in λgt10 with radiolabeled (random primed) murine 2-5A-dependent RNase cDNA (clone ZB1) as probe, Sambrook, J. et al., *Cold Spring Harbor Laboratory Press* (1989). Clone HBZ22 is isolated using radiolabeled HZB1 DNA as probe. The genomic human 2-5A-dependent RNase clone is isolated from a human placenta cosmid library in vector pVE15 (Stratagene) with a radiolabeled fragment of HZB22 DNA as probe. The murine genomic 2-5A-dependent RNase clone is isolated from a mouse 129SV genomic library in vector λFIXII (Stratagene) with a radiolabeled fragment of 2-5A-BP cDNA (clone ZB1) as probe. Subcloning of DNA is in Bluescript vectors (Stratagene).

Transcription of plasmids with phage RNA polymerases is in the presence of mGppppG as described (Promega) except that reaction mixtures are supplemented with 15% dimethyl sulfoxide and incubations are at about 37° C. for about 90 minutes. RNA is purified through Sephadex G50 spun-columns and ethanol precipitated prior to translation. Protein synthesis was performed, as described (Promega), at about 30° C. for about one hour in micrococcal nuclease-pretreated rabbit reticulocyte lysate or in an extract of wheat germ at about room temperature for about one hour and then at about 40° C. for about 12 hours. Translation reactions contain about 50 $\mu$M zinc sulfate. Endogenous 2-5A-dependent RNase in the reticulocyte lysate is removed by adsorption to about 30 $\mu$M of $p_2(A2'p)_3A$ covalently attached to cellulose (2-5A-cellulose), prepared as described in Wells, J. A. et al., *J. Biol. Chem.,* 259:1363–1370 (1984) and Silverman, R. H. and Krause, D., *I.R.L. Press, Oxford. England*, pp. 149–193 (1987), for about one hour on ice as described. See Silverman, R. H., *Anal. Biochem.,* 144:450–460 (1985). The 2-5A-dependent RNase:2-5A-cellulose complex is removed by twice centrifuging at about 400×g for about 5 minutes at about 2° C. The supernatant completely lacking in measurable levels of 2-5A-dependent RNase. See FIG. 5.

The set of nested 3'-deletions of the truncated murine 2-5A-dependent RNase cDNA, ZB1, is generated with exonuclease III/S1 nuclease digestion followed by filling-in with Klenow DNA Polymerase using the "Erase-A-Base" system (Promega).

The synthesis of the 2-5A probe, $p(A2'p)_2(br^8A2'p)_2A$ [32P]Cp, and its crosslinking to 2-5A-dependent RNase is performed exactly as described. See Nolan-Sorden, N. L. et al., *Anal. Biochem.,* 184:298–304 (1990). Briefly, the 2-5A probe, about 0.7 to 2.5 nM at 3,0009 Ci/mmole, is incubated for about one hour on ice with cell extract prepared as described, Silverman, R. H. and Krause, D., *I.R.L. Press, Oxford. England*, pp. 149–193 (1987), in the absence or presence of unlabeled oligonucleotide competitors. Covalent crosslinking is done under a uv lamp (308 nm) for one hour on ice and the proteins are separated on SDS/10% polyacrylamide gels. Filter assays for 2-5A binding activity using the 2-5A probe for about one hour on ice, as described in Knight, M. et al., *Nature,* 288:189–192 (1980).

Protease digestions are performed on gel-purified proteins in a gel, as described by Cleveland, D. W. et al., *J. Biol. Chem.,* 252:1102–1106 (1977).

The ribonuclease assay with 2-5A-cellulose is performed, as described by Silverman, R. H., *Anal. Biochem.,* 144:450–460 (1985). Briefly, lysates are adsorbed to about 30 $\mu$M of 2-5A-cellulose on ice for about two hours. The matrix is then washed three times by centrifuging and resuspending in buffer A. See Silverman, R. H., *Anal. Biochem.,* 144:450–460 (1985). The matrix is then incubated with poly(U)-[$^{32}$P]Cp or poly(C)-[$^{32}$P]Cp (both at about 16 $\mu$M in nucleotide equivalents) at about 30° C. and the levels of acid-precipitable radioactive RNA are determined by filtration on glass-fiber filters.

The Sanger dideoxy sequencing method is used to determine the DNA sequences (Sequenase, United States Biochemical).

The lysines in the truncated murine 2-5A-dependent RNase, clone ZB1, at positions 240 and 274 are mutated, individually and together, to asparagine residues. Mutants ZB1 (Lys$^{274}$-)Asn) and the double mutant, ZB1 (Lys$^{240,274}$-)Asn), are obtained with mutant oligonucleotides after subcloning ZB1 cDNA into pALTER-1 as described (Promega). Mutant ZB1 (Lys$^{240}$-)Asn) is obtained after polymerase chain reaction amplification of a segment of ZB1 with an upstream primer containing a unique HincII site attached to the mutant sequence and a second primer downstream of a unique BglII site. The HincII- and BglII-digested polymerase chain reaction product and similarly-digested clone ZB1 are then ligated. The specific mutations are: for codon 240, AAA→AAC and for codon 274, AAG→AAC. Mutants are confirmed by DNA sequencing.

EXAMPLE II

To study the structure, function, and properties of 2-5A-dependent RNase, milligram quantities of human recombinant 2-5A-dependent RNase were expressed in insect cells. To produce the milligram quantities, the cDNA to the human form of the endoribonuclease was subcloned in the baculovirus vector, BacPAK6 (Clontech), under the control of the polyhedrin promoter.

The cDNA encoding the entire coding sequence to the human form of 2-5A-dependent RNase, a Hind III fragment of plasmid ZC5 (Zhou et al., 1993), was cloned into the Bam HI of the transfer plasmid pBacPAK1 (Clontech) after filling-in the termini using Klenow fragment. Clones containing the cDNA in the correct orientation are determined by restriction enzyme analysis. The recombinant pBacPAK1/ZC5 DNA, 500 ng, are cotransfected into SF9 or SF21 cells with 200 ng of Bsu 361-digested $BacPAK_6$ viral DNA using the Lipfectin reagent (BRL). Plaques containing recombinant virus were identified by Southern blot analysis of PCR products obtained with Bac1 and Bac2 primers provided by the supplier (Clontech) probed with a 300 bp fragment of SacI-digested ZC5 DNA.

To produce recombinant 2-5A-dependent RNase, either monolayer or suspension (for large scale) cultures of SF21 cells were infected at a M.O.I. of 10 p.f.u. per cell at 27° C. for three days before harvesting. The cell pellets obtained after washing in phosphate buffered saline (pH 6.2) were frozen on dry ice and stored at −70° C.

Production of the enzyme in SF9 insect cells infected by the recombinant virus was measured by both 2-5A binding and 2-5A-dependent ribonuclease assays. 2-5A-binding activity was determined by covalent crosslinking of a bromine-substituted, $^{32}$P-labeled 2-5A analog to the RNase under ultraviolet light (Nolan-Sorden, N. L. et al., *Anal. Biochem.* 184, 298–304 1990). Extract of insect cells infected with the non-recombinant virus showed no detectable 2-5A-dependent RNase by this sensitive assay (FIG. 12, lane 1). In contrast, an intense, 80 kDa 2-5A-binding activity was detected in extract of insect cells infected with the recombinant virus (FIG. 12, lane 2).

To measure the catalytic activity of the recombinant enzyme, ribonuclease assay was performed in the presence and absence of trimer 2-5A, $p_3(A2'p)_2A$. The degradation of radiolabeled poly(rU) to acid-soluble fragments was measured in this assay (Silverman, R. H., *Anal. Biochem.* 144,450–460 1985). Crude extract of the insect cells infected with non-recombinant virus had no 2-5A-dependent RNase activity (FIG. 13). These findings are consistent with a previous study in which 2-5A-dependent RNase was shown to be absent in insect cells (Cayley et al., 1982). On the other hand, the RNA was extensively degraded (93%) in extract of the recombinant virus-infected cells incubated at 4° C. for thirty minutes in the presence of trimer 2-5A at 100 nM. In contrast, there was no RNA decay in the same extract incubated without addition of 2-5A (FIG. 13).

Figure 14:
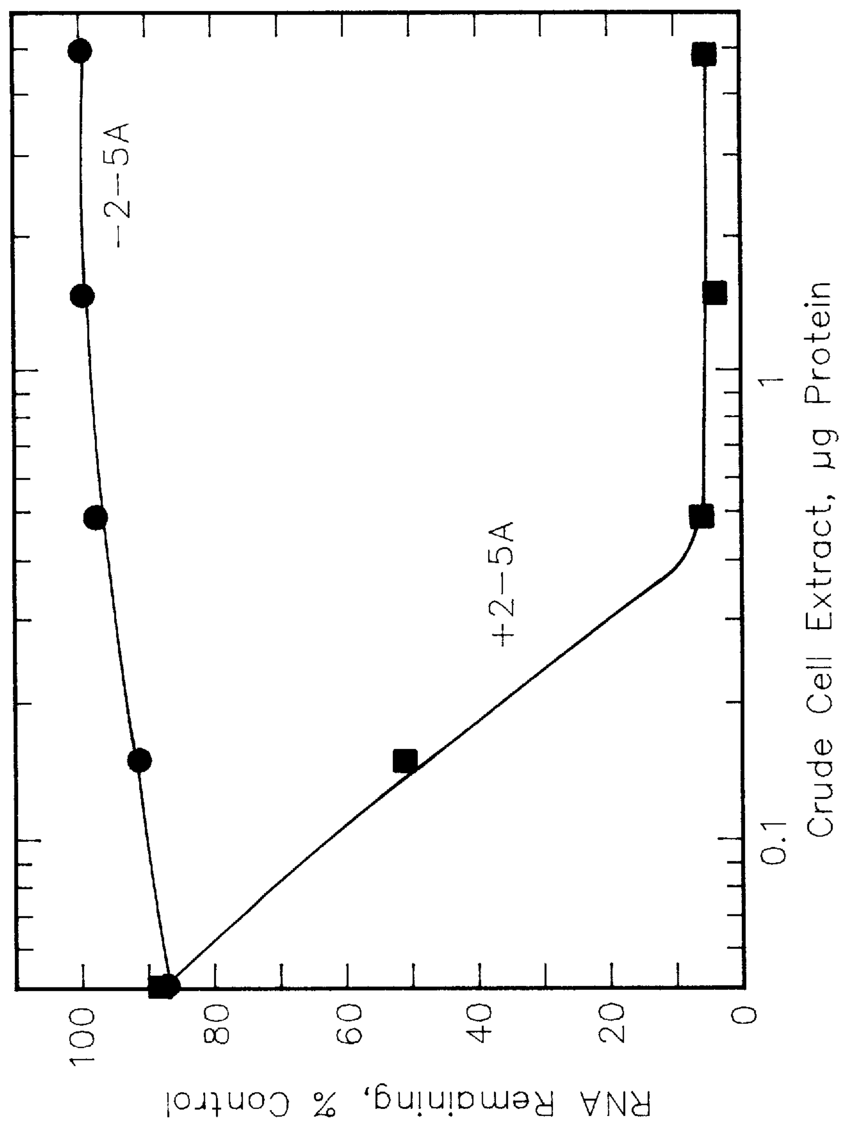
FIG. 14 shows 2-5A-dependent RNase activity in the crude extract of recombinant virus-infected cells as a function of protein concentration. Tetramer 2-5A was used at 100 nM and incubations were for 30 minutes at 30° C.
Figure 15:
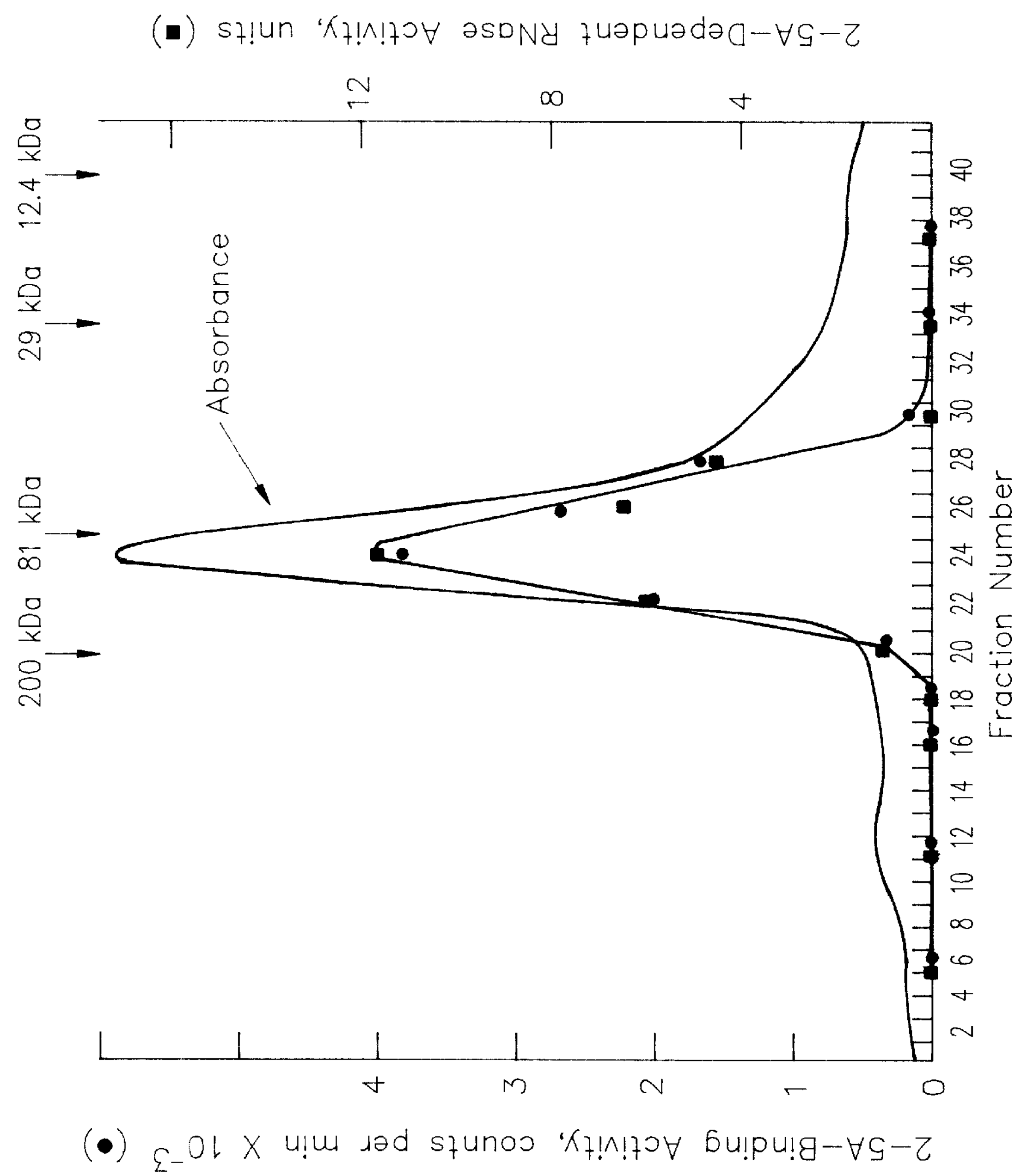
FIG. 15 shows the 2-5A-dependent RNase migrates as a monomer on a superose 12 gel filtration column. 2-5A-dependent RNase activity, expressed as unit per $\mu$l where one unit=50% degradation of 12 nM poly(rU)-$^{32}$P[Cp] in the presence 100 nM tetramer 2-5A for 30 minutes at 30° C. There was no RNase activity in the absence of 2-5A. 2-5A binding assays with the 2-5A probe were with 2 $\mu$l aliquots of fractions as described (Knight et al., *Nature,* 288:189–192, 1980 and Methods).

To determine the level of 2-5A-dependent RNase activity in the recombinant virus-infected insect cells, RNA decay was monitored as a function of cell extract amount (FIG. 14). Maximal 2-5A-dependent RNase activity was observed with only 0.5 $\mu$g of crude cell extract protein (FIG. 14). In comparison, assays of 2-5A-dependent RNase from mammalian cells typically require more than one-hundred fold higher amounts of cell extract for the detection of RNase activity (for example, 70 $\mu$g of mouse L cell protein per assay in Silverman, R. H., *Anal. Biochem.* 144,450–460 1985). These findings indicate that a high level of expression was obtained using the baculovirus system. Furthermore, the data indicate the recombinant enzyme is a fully functional, 2-5A-dependent RNase.

To determine the intrinsic properties of 2-5A-dependent RNase, purification of the recombinant enzyme was performed using an FPCL system (Pharmacia, Inc.). Three separation steps were used to obtain purification. First, a cell extract was prepared. To prepare the cell extract, four packed cell volumes of buffer A (25 mM Tris-HCl pH 7.4; 50 mM KCL; 10% glycerol; 1 mM EDTA; 0.1 mM ATP; 5 mM $MgCl_2$; 14 mM 2-mercaptoethanol; and 1 $\mu$g per ml of leupeptin) were added to cell pellets. The cell suspensions were sonicated on ice six times for 15 seconds at 30-second intervals. Supernatants were collected after centrifuging at 4° C. for three times at 16,700×g (once for 30 minutes, and then twice more for ten minutes each time).

Second, the chromatography steps used in the purification of the 2-5A-dependent RNase were performed with an FPLC system (Pharmacia). More particularly, about 20 mg of crude cell extract in 2 ml of buffer A was loaded onto an FPLC Blue sepharose column (5×50 mM, Pharmacia). After washing with 10-column volumes of buffer A at a flow rate of 0.3 ml per minute, the 2-5A-dependent RNase was eluted with buffer B (buffer A supplemented with 1M KCl). A linear gradient to 21% buffer B in about 23 minutes was performed. The 2-5A-dependent RNase was then eluted in about 8 ml during which time the ratio of buffer A:buffer B was held constant. The column fractions were monitored for 2-5A binding activity and then collected. The 2-5A-dependent RNase peak was observed after minutes of elution, corresponding to a KCl concentration of about 260 mM. The protein was concentrated and desalted with a Centricon filter unit according to the supplier (Amicon).

The blue sepharose fractions containing the peak of 2-5A-dependent RNase activity (about 2 to 2.5 mg of protein in 1 ml of buffer A per separation) were loaded on an FPLC Mono Q column (5×50 mm, Pharmacia) at a flow rate of 0.4 ml per minute. After washing with 10 column volumes buffer A, the 2-5A-dependent RNase was eluted in a linear gradient to 40% buffer B in 50 minutes at 0.4 ml per minute. The peak of 2-5A-dependent RNase (as determined by 2-5A binding assay) was observed after 7.5 to 15 minutes, corresponding to a KCl concentration of about 120 to 180 mM.

About 100 μg of 2-5A-dependent RNase per separation, obtained after purification by the previous two steps, in 100 μl of buffer C (buffer A containing 100 mM KCl) was loaded to an FPLC Superose 12 column (10×30 mm) at a flow rate of 0.2 ml per minute. Calibration of the column was with 100 μg each of the following proteins: B-amylase (200 k Da), human transferrin (75.2 k Da), carbonicanhydrase (29 k Da), and cytochrome c (12.4 k Da) (Sigma).

The expressed 2-5A-dependent RNase is clearly visible in the stained gel as the major protein present in crude extract of the recombinant virus-infected cells. Only a single band of protein was observed in the final, Superose-12, purified fraction of 2-5A-dependent RNase. The monomeric state of the purified 2-5A-dependent RNase was determined by its mobility on the Superose-12 column in comparison to the elution volumes of known marker proteins (FIG. 15). The elution volume of the 2-5A-dependent RNase peak, as determined by absorbance, 2-5A-binding activity, and 2-5A-dependent RNase activity (FIG. 15), match the 83,539 Da molecular mass of human 2-5A-dependent RNase, determined from the predicted amino acid sequence (Zhou, A. et al.*Cell* 72, 753–765 L1993). To quantitate the recovery and purity of the enzyme during its isolation, 2-5A-dependent RNase assays were performed on the different fractions. These findings indicate that in the crude insect cell extract the human 2-5A-dependent RNase is present at least 10% of the total soluble protein.

To determine the structural requirement of 2-5A required for activation of 2-5A-dependent RNase, ribonuclease activity against poly(rU) was determined as a function of oligonucleotide concentration. The purified 2-5A-dependent RNase was used in these assays. Maximal activation of 2-5-dependent RNase was obtained with 1 nM of $pA(2'p5'A)_3$, $pppA(2'p5'A)_2$, or $pppA(2'p5'A)_3$ (FIG. 16A). Therefore, only a single 5'-phosphoryl group linked to the 2',5'-oligoadenylate was required for maximal activation. In contrast, the dimer species, pppA2'p5'A, failed to activate the RNase indicating a minimal requirement of three adenylyl residues (FIG. 16A). The 2',5'-core species, lacking 5'-phosphoryl groups, were also analyzed and found to have greatly reduced activity (FIG. 16B). The trimer core species was more than 100-fold less active than the corresponding 5'-triphosphorylated compound; whereas the 2',5'-phosphorylated, trimer or tetramer 2',5'-oligoadenylates (FIG. 16A and B). The 3',5'linked compound, pppA (3'p5'A)2 (trimer triphosphate), failed to activate 2-5A-dependent RNase, even at a concentration of 1 μM (FIG. 16C). On the other hand, the 5'-blocked 2-5A analog, $A5'p_45'A(2'p5'A)_2$, was equal in activity to 2-5A per se while the inosine analog of 2-5A, $pppI(2'p5'A)_2$, had 10-fold reduced activity (FIG. 16C).

To confirm and extend previous studies on the sequence specificity of 2-5A-dependent RNase (Wreschner et al., 1981b; and Floyd-Smith et al., 1981), several types of nucleic acids were incubated with the purified, recombinant 2-5A-dependent RNase in the presence or absence of 2-5A. In this regard, poly(rG), poly(rC), and poly (dT) were not cleaved by activated 2-5A-dependent RNase whereas poly (rU) and, to a lesser extent poly(rA), were degraded (FIG. 17).

To determine the sizes of the RNA cleavage products, the RNA was analyzed on polyacrylamide gels (FIG. 17). Interestingly, the poly(rU) was cleaved into a set of discrete products (lanes 1 to 8). The products of 5, 7, 8, 12, 16 and 22 nucleotides in length were apparent after addition of 1 nM or higher concentrations of 2-5A (lanes 5 to 8). Degradation of poly(rA) was apparent only with about ten- to one hundred-fold higher levels of 2-5A than were required to degraded poly(rU) (FIG. 17, compare lanes 4 and 15). Specific cleavage products of poly(rA) were also seen, although to a less extent than with poly(rU). Degradation of poly(rU-rA) also produced discrete cleavage products (data not shown). Identical patterns of poly(rU) cleavage were observed with trimer, tetramer, or pentamer 2-5A whereas the dimer species was without activity (FIG. 18). Therefore, the specific cleavage products are not due to hybridization between the 2-5A and the substrate. A slightly altered, smaller, size distribution of the products of poly(rU) digestion was observed when assaying low levels of 2-5A-dependent RNase activity. A similar pattern of poly(rU) breakdown products was observed using crude mouse L cell 2-5A-dependent RNase.

The divalent cation requirements of 2-5A-dependent RNase were determined after extensive dialysis against buffer containing both EDTA and EGTA. More particularly, purified 2-5A-dependent RNase (about 100 μg in 100 μl), post-mono Q column fraction, was dialyzed at 4° C. against 25 mM Tris-HCl (pH 7.4), 2.5 mM EDTA, 2.5 mM EGTA, 14 mM 2-mercaptoethanol, and 100 mM KCl (first against 400 ml for four hours, then against 600 ml for ten hours, and finally against 200 ml of reaction buffer (EDTA and EGTA were reduced to 0.5 mM) for another four hours.

Activity assays were also performed in the presence of EDTA/EGTA to ensure the chelation of metal ions present in the reagents. 2-5A binding activity was measured by a modification of the filter method of Knight et al. (1980) and by the ultraviolet light crosslinking method of Nolan-Sorden, N. L. et al. *Anal. Biochem.* 184, 298–304 (1990). For the filter binding assay, a $^{32}$P-labeled and bromine substituted 2-5A analog, $p(A2'p)_2(br^8A2'p)_2A3'$-32P]Cp, 10,000 counts per minute per assay, at about 3,000 Ci per mmole, was incubated with fractions containing 2-5A-dependent RNase (or controls) at 4° C. for one hour. The reaction volumes were then transferred to nitrocellulose filters which were then washed twice in distilled water and dried and the amount of 2-5A probe bound to the 2-5A-dependent RNase on the filters was measured as described previously (Silverman R. H., et al., *Lymphokines and Interferons—A Practical Approach*, I.R.L. Press, Oxford, Ind., 149–193, (1987). The crosslinking assay was using the same 2-5A probe according to Nolan-Sorden, N. L. et al. *Anal. Biochem.* 184, 298–304 (1990).

RNA and DNA molecules used were poly(rU), poly(A), poly(G), poly(C), or poly(dT) from Pharmacia and were labeled at their 3'-termini with $^{32}$P-pCp (3,000 Ci per mmole) and T4 RNA ligase as described previously (Silverman, R. H., *Anal. Biochem.* 144, 450–460 1985). Fractions containing 2-5A-dependent RNase were incubated in the presence or absence of 100 nM of $p_3(A2'p)_3A$ (or other oligonucleotides), 8 to 16 nM of $^{32}$P-labeled RNA in final volumes of 25 μls at 30° C. The trichloracetic acid-insoluble fraction of RNA was then determined by filtering on glass-fiber filters in the presence of carrier yeast tRNA as described previously (Silverman, R. H., *Anal. Biochem.* 144, 450–460 1985).

2-5A-dependent RNase was capable of cleaving poly(rU) in response to the addition of 2-5A even in the absence of added divalent cations. Nevertheless, either magnesium or manganese greatly stimulated both 2-5A-binding activity and 2-5A-dependent RNase activity. In contrast, calcium had no effect and zinc was inhibitory. These findings suggest that divalent cations are not required for cleavage to occur. Instead, the enhanced binding of 2-5A to the 2-5A-dependent RNase in the presence of manganese or magnesium are probably responsible for the enhanced ribonuclease activity observed in the presence of these divalent cations.

It should be understood that the 2-5A "cores" (2',5'-linked oligoadenylates lacking a 5'-terminal phosphate) used in this study were obtained from commercial sources (Calbiochem, Sigma) and subjected to additional purification as described earlier (Torrence, P. F. et al., *J. Med. Chem.* 27, 726–733 1984). Alternatively, such "core" oligomers were prepared by alkaline phosphatase 5'-dephosphorylation followed by HPLC purification. In addition, a sample of core A2'p5'A2'p5'A was prepared by chemical synthesis (Imai J. Et al., *Methods Enzymol* 793, 233–249 (1981)).

The 5,-monophosphorylated 2,'5'-oligoadenylates were generally prepared by the lead ion catalyzed oligomerization of adenosine 5'-phophoroimidazolidate according to the published methodology (Torrence, P. F. et al., *J. Med. Chem.* 27, 726–733 1984; Imai J., et al., *J. Ord. Chem.* 50, 1418–1420 1985). The 5'-triphosphates were generated by reaction of the corresponding phosphoroimidazolidate with tri-n-butylammonium pyrophosphate (Imai, J., et al., *J. Ord. Chem.* 50, 1418–1420 1985).

Other oligonucleotides were prepared by described literature procedures: ppp5'A3'p5'A3'p5'A (lesiak et al., 1983); ppp5'I2'p5'A2'p5'A (Imai 1985; Imai, J., et al., *J. Ord. Chem.* 50, 1418–1420 1985); A5'pppp5'A2'p5'A2'p5'A (Imai, J., et al., *Biochemistry* 23, 744–766 1984).

The bromoadenylate employed in covalent binding studies, p5'A2'p5'A2'p5'(br$^{8}$A)2'p5'(br$^{8}$A) (Lesiak, IK., et al., *J. Biol. Chem.*, 262, 1961–1965, (1987); Torrence, P. K., et al., *Antiviral Res.* 18, 275–289, (1992); Nolan-Sorden, N. L., et al., *Anal. Biochem.* 184, 298–304 (1990) was prepared using a solid-phase synthesis method (Lesiak et al., in press) and was ligated to [$^{32}$P]-p5'C3'p as described Nolan-Sorden, N. L., et al., *Anal. Biochem.* 184, 298–304 (1990).

Previously, it was reported that ATP stimulated 2-5A-dependent RNase activity by about two-fold (Wreschner, D. H., et al., *Nucleic Acids Res.* 9, 1571–1581 (1981) and Krause, D., et al., 1986). To determine if the stimulation by ATP was a direct effect, assays were performed on the dialyzed 2-5A-dependent RNase in the presence or absence of added ATP. A stimulation of both activities was observed in the presence of ATP. Therefore, the ATP effect is believed to be due to a direct stimulation of the enzyme, perhaps due to enhance binding of 2-5A to the enzyme.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced herein.

TABLE I

Human 2-5A-depedent RNase

SEQ ID NO:1: and SEQ ID NO:2:

-103 aatcccaacttacactcaaagct
tctttgattaagtgctaggagataaatttgcattttctca
aggaaaaggctaaaagtggtagcaggtggcatttaccgtc

| | | | | | | | | | | |
|---|---|---|---|---|---|---|---|---|---|---|
| ATG | GAG | AGC | AGG | GAT | CAT | AAC | AAC | CCC | CAG | 30 |
| Met | Glu | Ser | Arg | Asp | His | Asn | Asn | Pro | Gln | 10 |
| GAG | GGA | CCC | ACG | TCC | TCC | AGC | GGT | AGA | AGG | 60 |
| Glu | Gly | Pro | Thr | Ser | Ser | Ser | Gly | Arg | Arg | 20 |
| GCT | GCA | GTG | GAA | GAC | AAT | CAC | TTG | CTG | ATT | 90 |
| Ala | Ala | Val | Glu | Asp | Asn | His | Leu | Leu | Ile | 30 |
| AAA | GCT | GTT | CAA | AAC | GAA | GAT | GTT | GAC | CTG | 120 |
| Lys | Ala | Val | Gln | Asn | Glu | Asp | Val | Asp | Leu | 40 |
| GTC | CAG | CAA | TTG | CTG | GAA | GGT | GGA | GCC | AAT | 150 |
| Val | Gln | Gln | Leu | Leu | Glu | Gly | Gly | Ala | Asn | 50 |
| GTT | AAT | TTC | CAG | GAA | GAG | GAA | GGG | GGC | TGG | 180 |
| Val | Asn | Phe | Gln | Glu | Glu | Glu | Gly | Gly | Trp | 60 |
| ACA | CCT | CTG | CAT | AAC | GCA | GTA | CAA | ATG | AGC | 210 |
| Thr | Pro | Leu | His | Asn | Ala | Val | Gln | Met | Ser | 70 |
| AGG | GAG | GAC | ATT | GTG | GAA | CTT | CTG | CTT | CGT | 240 |
| Arg | Glu | Asp | Ile | Val | Glu | Leu | Leu | Leu | Arg | 80 |
| CAT | GGT | GCT | GAC | CCT | GTT | CTG | AGG | AAG | AAG | 270 |
| His | Gly | Ala | Asp | Pro | Val | Leu | Arg | Lys | Lys | 90 |
| AAT | GGG | GCC | ACG | CTT | TTT | ATC | CTC | GCA | GCG | 300 |
| Asn | Gly | Ala | Thr | Leu | Phe | Ile | Leu | Ala | Ala | 100 |
| ATT | GCG | GGG | AGC | GTG | AAG | CTG | CTG | AAA | CTT | 330 |
| Ile | Ala | Gly | Ser | Val | Lys | Leu | Leu | Lys | Leu | 110 |
| TTC | CTT | TCT | AAA | GGA | GCA | GAT | GTC | AAT | GAG | 360 |
| Phe | Leu | Ser | Lys | Gly | Ala | Asp | Val | Asn | Glu | 120 |
| TGT | GAT | TTT | TAT | GGC | TTC | ACA | GCC | TTC | ATG | 390 |
| Cys | Asp | Phe | Tyr | Gly | Phe | Thr | Ala | Phe | Met | 130 |
| GAA | GCC | GCT | GTG | TAT | GGT | AAG | GTC | AAA | GCC | 420 |
| Glu | Ala | Ala | Val | Tyr | Gly | Lys | Val | Lys | Ala | 140 |
| CTA | AAA | TTC | CTT | TAT | AAG | AGA | GGA | GCA | AAT | 450 |
| Leu | Lys | Phe | Leu | Tyr | Lys | Arg | Gly | Ala | Asn | 150 |
| GTG | AAT | TTG | AGG | CGA | AAG | ACA | AAG | GAG | GAT | 480 |
| Val | Asn | Leu | Arg | Arg | Lys | Thr | Lys | Glu | Asp | 160 |
| CAA | GAG | CGG | CGG | AGG | AAA | GGA | GGG | GCC | ACA | 510 |
| Gln | Glu | Arg | Leu | Arg | Lys | Gly | Gly | Ala | Thr | 170 |
| GCT | CTC | ATG | GAC | GCT | GCT | GAA | AAA | GGA | CAC | 540 |
| Ala | Leu | Met | Asp | Ala | Ala | Glu | Lys | Gly | His | 180 |

TABLE I-continued

| Human 2-5A-depedent RNase | |
|---|---|
| GTA GAG GTC TTG AAG ATT CTC CTT GAT GAG | 570 |
| Val Glu Val Leu Lys Ile Leu Leu Asp Glu | 190 |
| ATG GGG GCA GAT GTA AAC GCC TGT GAC AAT | 600 |
| Met Gly Ala Asp Val Asn Ala Cys Asp Asn | 200 |
| ATG GGC AGA AAT GCC TTG ATC CAT GCT CTC | 630 |
| Met Gly Arg Asn Ala Leu Ile His Ala Leu | 210 |
| CTG AGC TCT GAC GAT AGT GAT GTG GAG GCT | 660 |
| Leu Ser Ser Asp Asp Ser Asp Val Glu Ala | 220 |
| ATT ACG CAT CTG CTG CTG GAC CAT GGG GCT | 690 |
| Ile Thr His Leu Leu Leu Asp His Gly Ala | 230 |
| GAT GTC AAT GTG AGG GGA GAA AGA GGG AAG | 720 |
| Asp Val Asn Val Arg Gly Glu Arg Gly Lys | 240 |
| ACT CCC CTG ATC CTG GCA GTG GAG AAG AAG | 750 |
| Thr Pro Leu Ile Leu Ala Val Glu Lys Lys | 250 |
| CAC TTG GGT TTG GTG CAG AGG CTT CTG GAG | 780 |
| His Leu Gly Leu Val Gln Arg Leu Leu Glu | 260 |
| CAA GAG CAC ATA GAG ATT AAT GAC ACA GAC | 810 |
| Gln Glu His Ile Glu Ile Asn Asp Thr Asp | 270 |
| AGT GAT GGC AAA ACA GCA CTG CTG CTT GCT | 840 |
| Ser Asp Gly Lys Thr Ala Leu Leu Leu Ala | 280 |
| GTT GAA CTC AAA CTG AAG AAA ATC GCC GAG | 870 |
| Val Glu Leu Lys Leu Lys Lys Ile Ala Glu | 290 |
| TTG CTG TGC AAA CGT GGA GCC AGT ACA GAT | 900 |
| Leu Leu Cys Lys Arg Gly Ala Ser Thr Asp | 300 |
| TGT GGG GAT CTT GTT ATG ACA GCG AGG CGG | 930 |
| Cys Gly Asp Leu Val Met Thr Ala Arg Arg | 310 |
| AAT TAT GAC CAT TCC CTT GTG AAG GTT CTT | 960 |
| Asn Tyr Asp His Ser Leu Val Lys Val Leu | 320 |
| CTC TCT CAT GGA GCC AAA GAA GAT TTT CAC | 990 |
| Leu Ser His Gly Ala Lys Glu Asp Phe His | 330 |
| CCT CCT GCT GAA GAC TGG AAG CCT CAG AGC | 1020 |
| Pro Pro Ala Glu Asp Trp Lys Pro Gln Ser | 340 |
| TCA CAC TGG GGG GCA GCC CTG AAG GAT CTC | 1050 |
| Ser His Trp Gly Ala Ala Leu Lys Asp Leu | 350 |
| CAC AGA ATA TAC CGC CCT ATG ATT GGC AAA | 1080 |
| His Arg Ile Tyr Arg Pro Met Ile Gly Lys | 360 |
| CTC AAG TTC TTT ATT GAT GAA AAA TAC AAA | 1110 |
| Leu Lys Phe Phe Ile Asp Glu Lys Tyr Lys | 370 |
| ATT GCT GAT ACT TCA GAA GGA GGC ATC TAC | 1140 |
| Ile Ala Asp Thr Ser Glu Gly Gly Ile Tyr | 380 |
| CTG GGG TTC TAT GAG AAG CAA GAA GTA GCT | 1170 |
| Leu Gly Phe Tyr Glu Lys Gln Glu Val Ala | 390 |
| GTG AAG ACG TTC TGT GAG GGC AGC CCA CGT | 1200 |
| Val Lys Thr Phe Cys Glu Gly Ser Pro Arg | 400 |
| GCA CAG CGG GAA GTC TCT TGT CTG CAA AGC | 1230 |
| Ala Gln Arg Glu Val Ser Cys Leu Gln Ser | 410 |
| AGC CGA GAG AAC AGT CAC TTG GTG ACA TTC | 1260 |
| Ser Arg Glu Asn Ser His Leu Val Thr Phe | 420 |
| TAT GGG AGT GAG AGC CAC AGG GGC CAC TTG | 1290 |
| Tyr Gly Ser Glu Ser His Arg Gly His Leu | 430 |
| TTT GTG TGT GTC ACC CTC TGT GAG CAG ACT | 1320 |
| Phe Val Cys Val Thr Leu Cys Glu Gln Thr | 440 |
| CTG GAA GCG TGT TTG GAT GTG CAC AGA GGG | 1350 |
| Leu Glu Ala Cys Leu Asp Val His Arg Gly | 450 |

TABLE I-continued

| Human 2-5A-depedent RNase | |
|---|---|
| GAA GAT GTG GAA AAT GAG GAA GAT GAA TTT | 1380 |
| Glu Asp Val Glu Asn Glu Glu Asp Glu Phe | 460 |
| GCC CGA AAT GTC CTG TCA TCT ATA TTT AAG | 1410 |
| Ala Arg Asn Val Leu Ser Ser Ile Phe Lys | 470 |
| GCT GTT CAA GAA CTA CAC TTG TCC TGT GGA | 1440 |
| Ala Val Gln Glu Leu His Leu Ser Cys Gly | 480 |
| TAC ACC CAC CAG GAT CTG CAA CCA CAA AAC | 1470 |
| Tyr Thr His Gln Asp Leu Gln Pro Gln Asn | 490 |
| ATC TTA ATA GAT TCT AAG AAA GCT GCT CAC | 1500 |
| Ile Leu Ile Asp Ser Lys Lys Ala Ala His | 500 |
| CTG GCA GAT TTT GAT AAG AGC ATC AAG TGG | 1530 |
| Leu Ala Asp Phe Asp Lys Ser Ile Lys Trp | 510 |
| GCT GGA GAT CCA CAG GAA GTC AAG AGA GAT | 1560 |
| Ala Gly Asp Pro Gln Glu Val Lys Arg Asp | 520 |
| CTA GAG GAC CTT GGA CGG CTG GTC CTC TAT | 1590 |
| Leu Glu Asp Leu Gly Arg Leu Val Leu Tyr | 530 |
| GTG GTA AAG AAG GGA AGC ATC TCA TTT GAG | 1620 |
| Val Val Lys Lys Gly Ser Ile Ser Phe Glu | 540 |
| GAT CTG AAA GCT CAA AGT AAT GAA GAG GTG | 1650 |
| Asp Leu Lys Ala Gln Ser Asn Glu Glu Val | 550 |
| GTT CAA CTT TCT CCA GAT GAG GAA ACT AAG | 1680 |
| Val Gln Leu Ser Pro Asp Glu Glu Thr Lys | 560 |
| GAC CTC ATT CAT CGT CTC TTC CAT CCT GGG | 1710 |
| Asp Leu Ile His Arg Leu Phe His Pro Gly | 570 |
| GAA CAT GTG AGG GAC TGT CTG AGT GAC CTG | 1740 |
| Glu His Val Arg Asp Cys Leu Ser Asp Leu | 580 |
| CTG GGT CAT CCC TTC TTT TGG ACT TGG GAG | 1770 |
| Leu Gly His Pro Phe Phe Trp Thr Trp Glu | 590 |
| AGC CGC TAT AGG ACG CTT CGG AAT GTG GGA | 1800 |
| Ser Arg Tyr Arg Thr Leu Arg Asn Val Gly | 600 |
| AAT GAA TCC GAC ATC AAA ACA CGA AAA TCT | 1830 |
| Asn Glu Ser Asp Ile Lys Thr Arg Lys Ser | 610 |
| GAA AGT GAG ATC CTC AGA CTA CTG CAA CCT | 1860 |
| Glu Ser Glu Ile Leu Arg Leu Leu Gln Pro | 620 |
| GGG CCT TCT GAA CAT TCC AAA AGT TTT GAC | 1890 |
| Gly Pro Ser Glu His Ser Lys Ser Phe Asp | 630 |
| AAG TGG ACG ACT AAG ATT AAT GAA TGT GTT | 1920 |
| Lys Trp Thr Thr Lys Ile Asn Glu Cys Val | 640 |
| ATG AAA AAA ATG AAT AAG TTT TAT GAA AAA | 1950 |
| Met Lys Lys Met Asn Lys Phe Tyr Glu Lys | 650 |
| AGA GGC AAT TTC TAC CAG AAC ACT GTG GGT | 1980 |
| Arg Gly Asn Phe Tyr Gln Asn Thr Val Gly | 660 |
| GAT CTG CTA AAG TTC ATC CGG AAT TTG GGA | 1210 |
| Asp Leu Leu Lys Phe Ile Arg Asn Leu Gly | 670 |
| GAA CAC ATT GAT GAA GAA AAG CAT AAA AAG | 2040 |
| Glu His Ile Asp Glu Glu Lys His Lys Lys | 680 |
| ATG AAA TTA AAA ATT GGA GAC CCT TCC CTG | 2070 |
| Met Lys Leu Lys Ile Gly Asp Pro Ser Leu | 690 |
| TAT TTT CAG AAG ACA TTT CCA GAT CTG GTG | 2100 |
| Tyr Phe Gln Lys Thr Phe Pro Asp Leu Val | 700 |
| ATC TAT GTC TAC ACA AAA CTA CAG AAC ACA | 2130 |
| Ile Tyr Val Tyr Thr Lys Leu Gln Asn Thr | 710 |
| GAA TAT AGA AAG CAT TTC CCC CAA ACC CAC | 2160 |
| Glu Tyr Arg Lys His Phe Pro Gln Thr His | 720 |

TABLE I-continued

Human 2-5A-depedent RNase

AGT CCA AAC AAA CCT CAG TGT GAT GGA GCT 2190
Ser Pro Asn Lys Pro Gln Cys Asp Gly Ala 730

GGT GGG GCC AGT GGG TTG GCC AGC CCT GGG 2220
Gly Gly Ala Ser Gly Leu Ala Ser Pro Gly 740

TGC 2223 tgatggactgatttgctggagttcagggaactact 2258
Cys 741 tattagctgtagagtccttggcaaatcacaacat 2292
tctgggccttttaactcaccaggttgcttgtgagggat 2330
gagttgcatagctgatatgtcagtccctggcatcgtg 2367
tattccatatgtctataacaaaagcaatatatacccag 2405
actacactagtccataagctttacccactaactggga 2442
ggacattctgctaagattccttttgtcaattgcaccaa 2480
aagaatgagtgccttgacccctaatgctgcatatgtt 2517
acaattctctcacttaattttcccaatgatcttgcaaa 2555
acagggattatcatccccatttaagaactgaggaacc 2592
tgagactcagagagtgtgagctactggcccaagattat 2630
tcaatttatacctagcactttataaatttatgtggtg 2667
ttattggtacctctcatttgggcaccttaaaacttaac 2705
tatcttccagggctcttccagatgaggcccaaaacat 2742
atataggggttccaggaatctcattcattcattcagta 2780
tttattgagcatctagtataagtctgggcactggatg 2817
catgaatt 2825

TABLE II

Murine 2-5A-dependent RNase (partial)
SEQ ID NO:3: and SEQ ID NO:4:

–163
attcggcacgaggaaggtgccaattactagctcccttctttattcgtgta ctgatgagatgtcagaagacagaacataatcagcccaatccctactccaa gactctcattgtgtcccaaagaaacacacgtgtgcatttcccaaggaaaa ggcattgaggacc ATG GAG ACC CCG GAT TAT 18
Met Glu Thr Pro Asp Tyr 6

AAC ACA CCT CAG GGT GGA ACC CCA TCA GCG 48
Asn Thr Pro Gln Gly Gly Thr Pro Ser Ala 16

GGA AGT CAG AGG ACC GTT GTC GAA GAT GAT 78
Gly Ser Gln Arg Thr Val Val Glu Asp Asp 26

TCT TCG TTG ATC AAA GCT GTT CAG AAG GGA 108
Ser Ser Leu Ile Lys Ala Val Gln Lys Gly 36

GAT GTT GTC AGG GTC CAG CAA TTG TTA GAA 138
Asp Val Val Arg Val Gln Gln Leu Leu Glu 46

AAA GGG GCT GAT GCC AAT GCC TGT GAA GAC 168
Lys Gly Ala Asp Ala Asn Ala Cys Glu Asp 56

ACC TGG GGC TGG ACA CCT TTG CAC AAC GCA 198
Thr Trp Gly Trp Thr Pro Leu His Asn Ala 66

GTG CAA GCT GGC AGG GTA GAC ATT GTG AAC 228
Val Gln Ala Gly Arg Val Asp Ile Val Asn 76

CTC CTG CTT AGT CAT GGT GCT GAC CCT CAT 258
Leu Leu Leu Ser His Gly Ala Asp Pro His 86

CGG AGG AAG AAG AAT GGG GCC ACC CCC TTC 288
Arg Arg Lys Lys Asn Gly Ala Thr Pro Phe 96

ATC ATT GCT GGG ATC CAG GGA GAT GTG AAA 318
Ile Ile Ala Gly Ile Gln Gly Asp Val Lys 106

CTG CTC GAG ATT CTC CTC TCT TGT GGT GCA 348
Leu Leu Glu Ile Leu Leu Ser Cys Gly Ala 116

TABLE II-continued

Murine 2-5A-dependent RNase (partial)
SEQ ID NO:3: and SEQ ID NO:4:

GAC GTC AAT GAG TGT GAC GAG AAC GGA TTC 378
Asp Val Asn Glu Cys Asp Glu Asn Gly Phe 126

ACG GCT TTC ATG GAA GCT GCT GAG CGT GGT 408
Thr Ala Phe Met Glu Ala Ala Glu Arg Gly 136

AAC GCT GAA GCC TTA AGA TTC CTT TTT GCT 438
Asn Ala Glu Ala Leu Arg Phe Leu Phe Ala 146

AAG GGA GCC AAT GTG AAT TTG CGA CGA CAG 468
Lys Gly Ala Asn Val Asn Leu Arg Arg Gln 156

ACA ACG AAG GAC AAA AGG CGA TTG AAG CAA 498
Thr Thr Lys Asp Lys Arg Arg Leu Lys Gln 166

GGA GGC GCC ACA GCT CTC ATG AGC GCT GCT 528
Gly Gly Ala Thr Ala Leu Met Ser Ala Ala 176

GAG AAG GGC CAC CTG GAA GTC CTG AGA ATT 558
Glu Lys Gly His Leu Glu Val Leu Arg Ile 186

CTC CTC AAT GAC ATG AAG GCA GAA GTC GAT 588
Leu Leu Asn Asp Met Lys Ala Glu Val Asp 196

GCT CGG GAC AAC ATG GGC AGA AAT GCC CTG 618
Ala Arg Asp Asn Met Gly Arg Asn Ala Leu 206

ATC CGT ACT CTG CTG AAC TGG GAT TGT GAA 648
Ile Arg Thr Leu Leu Asn Trp Asp Cys Glu 216

AAT GTG GAG GAG ATT ACT TCA ATC CTG ATT 678
Asn Val Glu Glu Ile Thr Ser Ile Leu Ile 226

CAG CAC GGG GCT GAT GTT AAC GTG AGA GGA 708
Gln His Gly Ala Asp Val Asn Val Arg Gly 236

GAA AGA GGG AAA ACA CCC CTC ATC GCA GCA 738
Glu Arg Gly Lys Thr Pro Leu Ile Ala Ala 246

GTG GAG AGG AAG CAC ACA GGC TTG GTG CAG 768
Val Glu Arg Lys His Thr Gly Leu Val Gln 256

ATG CTC CTG AGT CGG GAA GGC ATA AAC ATA 798
Met Leu Leu Ser Arg Glu Gly Ile Asn Ile 266

GAT GCC AGG GAT AAC GAG GGC AAG ACA GCT 828
Asp Ala Arg Asp Asn Glu Gly Lys Thr Ala 276

CTG CTA ATT GCT GTT GAT AAA CAA CTG AAG 858
Leu Leu Ile Ala Val Asp Lys Gln Leu Lys 286

GAA ATT GTC CAG TTG CTT CTT GAA AAG GGA 888
Glu Ile Val Gln Leu Leu Leu Glu Lys Gly 296

GCT GAT AAG TGT GAC GAT CTT GTT TGG ATA 918
Ala Asp Lys Cys Asp Asp Leu Val Trp Ile 306

GCC AGG AGG AAT CAT GAC TAT CAC CTT GTA 948
Ala Arg Arg Asn His Asp Tyr His Leu Val 316

AAG CTT CTC CTC CCT TAT GTA GCT AAT CCT 978
Lys Leu Leu Leu Pro Tyr Val Ala Asn Pro 326

GAC ACC GAC CCT CCT GCT GGA GAC TGG TCG 1008
Asp Thr Asp Pro Pro Ala Gly Asp Trp Ser 336

CCT CAC AGT TCA CGT TGG GGG ACA GCC TTG 1038
Pro His Ser Ser Arg Trp Gly Thr Ala Leu 346

AAA AGC CTC CAC AGT ATG ACT CGA CCC ATG 1068
Lys Ser Leu His Ser Met Thr Arg Pro Met 356

ATT GGC AAA CTC AAG ATC TTC ATT CAT GAT 1098
Ile Gly Lys Leu Lys Ile Phe Ile His Asp 366

GAC TAT AAA ATT GCT GGC ACT TCC GAA GGG 1128
Asp Tyr Lys Ile Ala Gly Thr Ser Glu Gly 376

TABLE II-continued

| Murine 2-5A-dependent RNase (partial) SEQ ID NO:3: and SEQ ID NO:4: | | | | | | | | | | |
|---|---|---|---|---|---|---|---|---|---|---|
| GCT | GTC | TAC | CTA | GGG | ATC | TAT | GAC | AAT | CGA | 1158 |
| Ala | Val | Tyr | Leu | Gly | Ile | Tyr | Asp | Asn | Arg | 386 |
| GAA | GTG | GCT | GTG | AAG | GTC | TTC | CGT | GAG | AAT | 1188 |
| Glu | Val | Ala | Val | Lys | Val | Phe | Arg | Glu | Asn | 396 |
| AGC | CCA | CGT | GGA | TGT | AAG | GAA | GTC | TCT | TGT | 1218 |
| Ser | Pro | Arg | Gly | Cys | Lys | Glu | Val | Ser | Cys | 406 |
| CTG | CGG | GAC | TGC | GGT | GAC | CAC | AGT | AAC | TTA | 1248 |
| Leu | Arg | Asp | Cys | Gly | Asp | His | Ser | Asn | Leu | 416 |
| GTG | GCT | TTC | TAT | GGA | AGA | GAG | GAC | GAT | AAG | 1278 |
| Val | Ala | Phe | Tyr | Gly | Arg | Glu | Asp | Asp | Lys | 426 |
| GGC | TGT | TTA | TAT | GTG | TGT | GTG | TCC | CTG | TGT | 1308 |
| Gly | Cys | Leu | Tyr | Val | Cys | Val | Ser | Leu | Cys | 436 |
| GAG | TGG | ACA | CTG | GAA | GAG | TTC | CTG | AGG | TTG | 1338 |
| Glu | Trp | Thr | Leu | Glu | Glu | Phe | Leu | Arg | Leu | 446 |
| CCC | AGA | GAG | GAA | CCT | GTG | GAG | AAC | GGG | GAA | 1368 |
| Pro | Arg | Glu | Glu | Pro | Val | Glu | Asn | Gly | Glu | 456 |
| GAT | AAG | TTT | GCC | CAC | AGC | ATC | CTA | TTA | TCT | 1398 |
| Asp | Lys | Phe | Ala | His | Ser | Ile | Leu | Leu | Ser | 466 |
| ATA | TTT | GAG | GGT | GTT | CAA | AAA | CTA | CAC | TTG | 1428 |
| Ile | Phe | Glu | Gly | Val | Gln | Lys | Leu | His | Leu | 476 |
| CAT | GGA | TAT | TCC | CAT | CAG | GAC | CTG | CAA | CCA | 1458 |
| His | Gly | Tyr | Ser | His | Gln | Asp | Leu | Gln | Pro | 486 |
| CAA | AAC | ATC | TTA | ATA | GAT | TCC | AAG | AAA | GCT | 1488 |
| Gln | Asn | Ile | Leu | Ile | Asp | Ser | Lys | Lys | Ala | 496 |
| GTC | CGG | CTG | GCA | GAT | TTT | GAT | CAG | AGC | ATC | 1518 |
| Val | Arg | Leu | Ala | Asp | Phe | Asp | Gln | Ser | Ile | 506 |
| CGA | TGG | ATG | GGA | GAG | TCA | CAG | ATG | GTC | AGG | 1548 |
| Arg | Trp | Met | Gly | Glu | Ser | Gln | Met | Val | Arg | 516 |
| AGA | GAC | TTG | GAG | GAT | CTT | GGA | CGG | CTG | GTT | 1578 |
| Arg | Asp | Leu | Glu | Asp | Leu | Gly | Arg | Leu | Val | 526 |
| CTC | TAC | GTG | GTA | ATG | AAA | GGT | GAG | ATC | CCC | 1608 |
| Leu | Tyr | Val | Val | Met | Lys | Gly | Glu | Ile | Pro | 536 |
| TTT | GAG | ACA | CTA | AAG | ACT | CAG | AAT | GAT | GAA | 1638 |
| Phe | Glu | Thr | Leu | Lys | Thr | Gln | Asn | Asp | Glu | 546 |
| GTG | CTG | CTT | ACA | ATG | TCT | CCA | GAT | GAG | GAG | 1668 |
| Val | Leu | Leu | Thr | Met | Ser | Pro | Asp | Glu | Glu | 556 |
| ACT | AAG | GAC | CTC | ATT | CAT | TGC | CTG | TTT | TCT | 1698 |
| Thr | Lys | Asp | Leu | Ile | His | Cyc | Leu | Phe | Ser | 566 |
| CCT | GGA | GAA | AAT | GTC | AAG | AAC | TGC | CTG | GTA | 1728 |
| Pro | Gly | Glu | Asn | Val | Lys | Asn | Cys | Leu | Val | 576 |
| GAC | CTG | CTT | GGC | CAT | CCT | TTC | TTT | TGG | ACT | 1758 |
| Asp | Leu | Leu | Gly | His | Pro | Phe | Phe | Trp | Thr | 586 |
| TGG | GAG | AAC | CGC | TAT | AGA | ACA | CTC | CGG | AAT | 1788 |
| Trp | Glu | Asn | Arg | Tyr | Arg | Thr | Leu | Arg | Asn | 596 |
| GTG | GGA | AAT | GAA | TCT | GAC | ATC | AAA | GTA | CGG | 1818 |
| Val | Gly | Asn | Glu | Ser | Asp | Ile | Lys | Val | Arg | 606 |
| AAA | TGT | AAA | AGT | GAT | CTT | CTC | AGA | CTA | CTG | 1848 |
| Lys | Cys | Lys | Ser | Asp | Leu | Leu | Arg | Leu | Leu | 616 |
| CAG | CAT | CAG | ACA | CTT | GAG | CCT | CCC | AGA | AGC | 1878 |
| Gln | His | Gln | Thr | Leu | Glu | Pro | Pro | Arg | Ser | 626 |
| TTT | GAC | CAG | TGG | ACA | TCT | AAG | ATC | GAC | AAA | 1908 |
| Phe | Asp | Gln | Trp | Thr | Ser | Lys | Ile | Asp | Lys | 636 |
| AAT | GTT | ATG | GAT | GAA | ATG | AAT | CAT | TTC | TAC | 1938 |
| Asn | Val | Met | Asp | Glu | Met | Asn | His | Phe | Tyr | 646 |
| GAA | AAG | AGA | AAA | AAA | AAC | CCT | TAT | CAG | GAT | 1968 |
| Glu | Lys | Arg | Lys | Lys | Asn | Pro | Tyr | Gln | Asp | 656 |
| ACT | GTA | GGT | GAT | CTG | CTG | AAG | TTT | ATT | CGG | 1998 |
| Thr | Val | Gly | Asp | Leu | Leu | Lys | Phe | Ile | Arg | 666 |
| AAT | ATA | GGC | GAA | CAC | ATC | AAT | GAG | GAA | AAA | 2028 |
| Asn | Ile | Gly | Glu | His | Ile | Asn | Glu | Glu | Lys | 676 |
| AAG | CGG | GGG | | | | | | | | 2037 |
| Lys | Arg | Gly | | | | | | | | 679 |

REFERENCES

Ball, L. A. (1980) *Ann. N. Y. Acad. Sci.* 350, 486–496

Belasco, J. and Brawerman, G. (1993) *Control of Messenger RNA Stability*, Academic Press, Inc, New York Bisbal, C., Salehzada, T., Lebleu, B., and Bayard, B. (1989) *Eur. J. Biochem.* 179, 595–602

Brown, G. E., Lebleu, B., Kawakita, M., Shaila, S., Sen, G. C., and Lengyel, P. (1976) *Biochem. Biophys. Res. Commun.* 69, 114–122

Cayley, P. J. and Kerr, I. M. (1982) *Eur. J. Biochem.* 122, 601–608

Clemens, M. J. and Williams,B. R. G. (1978) *Cell,* 13, 565–572

Deutscher, M. P. (1993) *J. Biol. Chem.* 268, 13011–13014

Doornbos, J., Charubala, R., Pfleiderer, W., and Altona, C. (1983) *Nucleic Acids Res.* 11, 4569–4582

Doornbos, J., Den Hartog, J. A. J., v. Boom J. H., and Altona, C. (1981) *Eur. J. Biochem.* 116, 403–412

Drocourt, J.-L., Dieffenbach, C. W., Ts'o, P. O. P., Justesen, J., and Thang, M. N. (1982) *Nucleic Acids Res.* 10, 2163–2174

Ferbus, D., Justesen, J., Besancon, F., and Thang, M. N. (1981) *Biochem. Biophys. Res. Comm.* 100, 847–456

Floyd-Smith, G, Slattery, E. and Lengyel, P. (1981) *Science,* 212, 1020–1032

Hassel, B. A., Zhou, A., Sotomayor, C., Maran, A., and Silverman, R. H. (1993) *EMBO J.* 12, 3297–3304

Haugh, M. C., Cayley, P. J., Serafinoska, H., Norman, D. G., Reese, C. B., and Kerr, I. M. (1983) *Eur. J. Biochem.* 132, 77–84

Hovanessian, A. G., Brown, R. E. and Kerr, I. M. (1977) *Nature,* 268, 537–539

Jacobsen, H., Czarniecki, C. W., Krause, D., Friedman, R. M. and Silverman, R. H. (1983a) *Virology,* 125, 496–501.

Jacobsen, H., Krause, D., Friedman, R. M. and Silverman, R. H. (1983b) *Proc. Natl. Acad. Sci. U.S.A.,* 80, 4954–4958

Johnston, M. I. and Torrence, P. F. (1984) in *Inteferon*, vol.3, R. M. Friedman, ed., Elsevier, New York, N.Y., pp. 189–298

Kerr, I. M., Brown, R. E., Clemens, M. J., and Gilbert, C. S. (1976) *Eur. J. Biochem.* 69, 551–561

Kerr, I. M., Brown, R. E., and Ball, L. A. (1974) *Nature* 250, 57–59

Kerr, I. M. and Brown, R. E. (1978) *Proc. Natl. Acad. Sci. U.S.A.,* 75, 256–260

Kinjo, J.-E., Pabuccuoglu, A., Alster, D. K., Lesiak, K., and Torrence, P. F. (1992) *Drug Des. Disc.* 8, 241–254.

Kitade, Y., Alster, D. K., Pabuccuoglu, A., and Torrence, P. F. (1991) *Bioorg. Chem.* 19, 283–299.

Kondo, N. S., Holmes, H. M., Stempel, L. M. and Ts'o, P. O. P. (1970) *Biochemistry* 9, 3479–3498

Krause, D., Lesiak, K., Imai, J., Sawai, H., Torrence, P. F. and Silverman, R. H. (1986) *J. Biol. Chem.* 261, 6836–6839

Knight, M., Cayley, P. J., Silverman, R. H., Wreschner D. H., Gilbert, C. S., Brown, R. E., and Kerr, I. M. (1980) *Nature* 288, 189–192

Knight, M., Wreschner, D. H., Silverman, R. H., and Kerr, I. M., (1981) *Methods Enzymol.* 79, 216–227

Kovacs, T., Pabuccuoglu, A., Lesiak, K., and Torrence, P. F. (1993) *Bioorg. Chem.* 21, 192–208

Krause, D. Silverman, R. H., Jacobsen, H., Leisy, S. A., Dieffenbach, C. W. and Friedman, R. M. (1985b) *Eur. J. Biochem.,* 146, 611–618

Lengyel, P. (1993) *Proc. Natl. Acad. Sci. U.S.A.* 90, 5893–5895

Lesiak, K. and Torrence, P. F. (1985) *Biochem. Biophys. Res. Comm.* 126, 917–921

Martin, E. M., Birdsall, N. J. M., Brown, R. E., and Kerr, I. M. (1979) *Eur. J Biochem.* 95, 295–307

Nilsen, T. W. and Baglioni, C. (1979) *Proc. Natl. Acad. Sci. U.S.A.,* 76, 2600–2604

Salehzada, T., Silhol, M., Steff, A. M., Lebleu, B., and Bisbal, C. (1993) *J. Biol. Chem.* 268, 7733–7740

Silverman, R. H., Jung, D. D., Nolan-Sorden, N. L., Dieffenbach, C. W., Kedar, V. P. and SenGupta, D. N. (1988). *J. Biol. Chem.* 263, 7336–7341

Silverman, R. H. and Krause, D. (1987) In, Clemens, M. J., Morris, A. G., and Gearing, A. J. H., (eds.), *Lymphokines and Interferons—A Practical Approach.* I.R.L. Press, Oxford, pp. 149–193.

Slattery, E., Gosh, N., Samanta, H., and Lengyel, P. (1979) *Proc. Natl. Acad. Sci. U.S.A.* 76, 4778–4782

Torrence, P. F., Brozda, D., Alster, D., Charubala, R., and Pfleiderer, W. (1988) *J. Biol. Chem.* 263, 1131–1139

Torrence, P. F., Imai, J., Jamoulle, J.-C., and Lesiak, K, (1986) *Chem. Scripta* 26, 141–145

Torrence, P. F., Maitra, R. K., Lesiak, K., Khamnei, S., Zhou, A., and Silverman, R. H. (1993) *Proc. Natl. Acad. Sci. U.S.A.* 90, 1300–1304

Van Den Hoogen, Y. T., Hilgerson, C. M. A., Brozda, D., Lesiak, K., Torrence, P. F., and Altona, C. (1989) *Eur. J. Biochem.* 182, 629–637

White, J. C., Williams, R. W. and Johnston, M. I. (1987) *Biochemistry* 26, 7737–7744

Wreschner, D. H. James, T. C., Silverman, R. H., and Kerr, I. M. (1981a). *Nucleic Adds Res.* 9, 1571–1581

Wreschner, D. H., McCauley, J. W., Skehel, J. J. and Kerr,I. M. (1981b) *Nature,* 289, 414–417

Wreschner, D. H., Silverman, R. H., James, T. C., Gilbert, C. S., and Kerr, I. M. (1982). *Eur. J. Biochem.* 124, 261–268

Zhou, A., Hassel, B. A., and Silverman, R. H. (1993) *Cell* 72, 753–765

We claim:

1. An insect cell capable of expressing human 2-5A-dependent RNase at levels at least two orders of magnitude higher than those obtained from mammalian cells, said insect cell including a recombinant baculovirus expression vector which contains a cDNA encoding the 2-5A-dependent RNase, said 2-5-dependent RNase having an amino acid residue sequence corresponding to human 2-5A-dependent RNase amino acid residue sequence designated as SEQ ID NO: 2.

2. An insect cell of claim 1, said recombinant baculovirus expression vector comprising BacPAK6 transformed with pBacPAK1/ZC5 DNA having ATCC Accession No. 98504.

3. An insect cell of claim 2, said insect cell being selected from the group consisting of SF9 and SF21 insect cells.

4. An insect cell from claim 1, wherein said insect cell is infected with recombinant baculovirus expressing human 2-5A-dependent RNase.

5. An insect cell of claim 1, the cDNA having an encoding nucleotide sequence corresponding to encoding human 2-5A-dependent RNase nucleotide sequence designated as SEQ ID NO: 1.

6. An insect cell of claim 1, the 2-5A-dependent RNase having an amino acid residue sequence corresponding to amino acid residue sequence expressed by plasmid ZC5.

7. An insect cell of claim 1, the 2-5A-dependent RNase having an amino acid residue sequence corresponding to amino acid residue sequence expressed by a HindIII fragment of plasmid ZC5.

8. An insect cell of claim 1, the human 2-5A-dependent RNase having an amino acid residue sequence in SEQ ID NO: 2 selected from the group consisting of amino acid residue sequence designated as amino acid residues 220–741, amino acid residue sequence designated as amino acid residues 62–397, amino acid residue sequence designated as amino acid residues 62–741 and amino acid residue sequence designated as amino acid residues 1–741.

9. An insect cell capable of expressing human 2-5A-dependent RNase, said insect cell being transfected with recombinant baculovirus expression vector comprising BacPAK6 transformed with transfer plasmid pBacPAK1/ZC5 DNA, said transfer plasmid pBaCPAK1/ZC5 DNA comprising transfer plasmid pBacPAK1 having cloned therein a HindIII fragment of plasmid ZC5 after filling in the termini of transfer plasmid pBacPAK1 using Klenow fragment, said plasmid ZC5 including cDNA encoding human 2-5A-dependent RNase.

10. An insect cell capable of expressing murine 2-5A-dependent RNase at levels at least two orders of magnitude higher than those obtained from mammalian cells, said insect cell including a recombinant baculovirus expression vector which contains a cDNA encoding the 2-5A-dependent RNase, said 2-5A-dependent RNase having an amino acid residue sequence corresponding to murine 2-5A- dependent RNase amino acid residue sequence designated as SEQ ID NO: 4.

11. An insect cell of claim 10, said insect cell being selected from the group consisting of SF9 and SF21 insect cells.

12. An insect cell of claim 10, the cDNA having an encoding nucleotide sequence corresponding to encoding murine 2-5A-dependent RNase nucleotide sequence designated as SEQ ID NO: 3.

13. An insect cell of claim 10, the 2-5A-dependent RNase having an amino acid residue sequence being selected from the group consisting of amino acid residue sequences corresponding to those expressed by clones ZB1, ZB2, ZB3, ZB5, ZB9, ZB10, ZB11 and ZB13.

14. An insect cell of claim 10, said cDNA encoding murine 2-5A-dependent RNase, the cDNA having a nucleotide sequence which corresponds to at least the encoding nucleotide sequence for clone ZB13.

15. An insect cell of claim 16, the cDNA having a nucleotide sequence which at least corresponds to the encoding nucleotide sequence for clone ZB2.

16. An insect cell of claim 16, the cDNA having a nucleotide sequence which corresponds to the encoding nucleotide sequence for clone ZB 1.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 2928 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Homo sapiens ( i x ) FEATURE:
( A ) NAME/KEY: CDS
( B ) LOCATION: 104..2326

( x i ) SEQUENCE DESCRIPTION: SEQ ID NO:1:

```
AATCCCAACT TACACTCAAA GCTTCTTTGA TTAAGTGCTA GGAGATAAAT TTGCATTTTC      60

TCAAGGAAAA GGCTAAAAGT GGTAGCAGGT GGCATTTACC GTC ATG GAG AGC AGG       115
                                                Met Glu Ser Arg
                                                  1

GAT CAT AAC AAC CCC CAG GAG GGA CCC ACG TCC TCC AGC GGT AGA AGG       163
Asp His Asn Asn Pro Gln Glu Gly Pro Thr Ser Ser Ser Gly Arg Arg
  5                  10                  15                  20

GCT GCA GTG GAA GAC AAT CAC TTG CTG ATT AAA GCT GTT CAA AAC GAA       211
Ala Ala Val Glu Asp Asn His Leu Leu Ile Lys Ala Val Gln Asn Glu
                 25                  30                  35

GAT GTT GAC CTG GTC CAG CAA TTG CTG GAA GGT GGA GCC AAT GTT AAT       259
Asp Val Asp Leu Val Gln Gln Leu Leu Glu Gly Gly Ala Asn Val Asn
             40                  45                  50
```

-continued

```
TTC CAG GAA GAG GAA GGG GGC TGG ACA CCT CTG CAT AAC GCA GTA CAA      307
Phe Gln Glu Glu Glu Gly Gly Trp Thr Pro Leu His Asn Ala Val Gln
         55                  60                  65

ATG AGC AGG GAG GAC ATT GTG GAA CTT CTG CTT CGT CAT GGT GCT GAC      355
Met Ser Arg Glu Asp Ile Val Glu Leu Leu Leu Arg His Gly Ala Asp
     70                  75                  80

CCT GTT CTG AGG AAG AAG AAT GGG GCC ACG CTT TTT ATC CTC GCA GCG      403
Pro Val Leu Arg Lys Lys Asn Gly Ala Thr Leu Phe Ile Leu Ala Ala
 85                  90                  95                 100

ATT GCG GGG AGC GTG AAG CTG CTG AAA CTT TTC CTT TCT AAA GGA GCA      451
Ile Ala Gly Ser Val Lys Leu Leu Lys Leu Phe Leu Ser Lys Gly Ala
                105                 110                 115

GAT GTC AAT GAG TGT GAT TTT TAT GGC TTC ACA GCC TTC ATG GAA GCC      499
Asp Val Asn Glu Cys Asp Phe Tyr Gly Phe Thr Ala Phe Met Glu Ala
            120                 125                 130

GCT GTG TAT GGT AAG GTC AAA GCC CTA AAA TTC CTT TAT AAG AGA GGA      547
Ala Val Tyr Gly Lys Val Lys Ala Leu Lys Phe Leu Tyr Lys Arg Gly
        135                 140                 145

GCA AAT GTG AAT TTG AGG CGA AAG ACA AAG GAG GAT CAA GAG CGG CTG      595
Ala Asn Val Asn Leu Arg Arg Lys Thr Lys Glu Asp Gln Glu Arg Leu
    150                 155                 160

AGG AAA GGA GGG GCC ACA GCT CTC ATG GAC GCT GCT GAA AAA GGA CAC      643
Arg Lys Gly Gly Ala Thr Ala Leu Met Asp Ala Ala Glu Lys Gly His
165                 170                 175                 180

GTA GAG GTC TTG AAG ATT CTC CTT GAT GAG ATG GGG GCA GAT GTA AAC      691
Val Glu Val Leu Lys Ile Leu Leu Asp Glu Met Gly Ala Asp Val Asn
                185                 190                 195

GCC TGT GAC AAT ATG GGC AGA AAT GCC TTG ATC CAT GCT CTC CTG AGC      739
Ala Cys Asp Asn Met Gly Arg Asn Ala Leu Ile His Ala Leu Leu Ser
            200                 205                 210

TCT GAC GAT AGT GAT GTG GAG GCT ATT ACG CAT CTG CTG CTG GAC CAT      787
Ser Asp Asp Ser Asp Val Glu Ala Ile Thr His Leu Leu Leu Asp His
        215                 220                 225

GGG GCT GAT GTC AAT GTG AGG GGA GAA AGA GGG AAG ACT CCC CTG ATC      835
Gly Ala Asp Val Asn Val Arg Gly Glu Arg Gly Lys Thr Pro Leu Ile
    230                 235                 240

CTG GCA GTG GAG AAG AAG CAC TTG GGT TTG GTG CAG AGG CTT CTG GAG      883
Leu Ala Val Glu Lys Lys His Leu Gly Leu Val Gln Arg Leu Leu Glu
245                 250                 255                 260

CAA GAG CAC ATA GAG ATT AAT GAC ACA GAC AGT GAT GGC AAA ACA GCA      931
Gln Glu His Ile Glu Ile Asn Asp Thr Asp Ser Asp Gly Lys Thr Ala
                265                 270                 275

CTG CTG CTT GCT GTT GAA CTC AAA CTG AAG AAA ATC GCC GAG TTG CTG      979
Leu Leu Leu Ala Val Glu Leu Lys Leu Lys Lys Ile Ala Glu Leu Leu
            280                 285                 290

TGC AAA CGT GGA GCC AGT ACA GAT TGT GGG GAT CTT GTT ATG ACA GCG     1027
Cys Lys Arg Gly Ala Ser Thr Asp Cys Gly Asp Leu Val Met Thr Ala
        295                 300                 305

AGG CGG AAT TAT GAC CAT TCC CTT GTG AAG GTT CTT CTC TCT CAT GGA     1075
Arg Arg Asn Tyr Asp His Ser Leu Val Lys Val Leu Leu Ser His Gly
    310                 315                 320

GCC AAA GAA GAT TTT CAC CCT CCT GCT GAA GAC TGG AAG CCT CAG AGC     1123
Ala Lys Glu Asp Phe His Pro Pro Ala Glu Asp Trp Lys Pro Gln Ser
325                 330                 335                 340

TCA CAC TGG GGG GCA GCC CTG AAG GAT CTC CAC AGA ATA TAC CGC CCT     1171
Ser His Trp Gly Ala Ala Leu Lys Asp Leu His Arg Ile Tyr Arg Pro
                345                 350                 355

ATG ATT GGC AAA CTC AAG TTC TTT ATT GAT GAA AAA TAC AAA ATT GCT     1219
Met Ile Gly Lys Leu Lys Phe Phe Ile Asp Glu Lys Tyr Lys Ile Ala
            360                 365                 370
```

-continued

```
GAT ACT TCA GAA GGA GGC ATC TAC CTG GGG TTC TAT GAG AAG CAA GAA      1267
Asp Thr Ser Glu Gly Gly Ile Tyr Leu Gly Phe Tyr Glu Lys Gln Glu
        375                 380                 385

GTA GCT GTG AAG ACG TTC TGT GAG GGC AGC CCA CGT GCA CAG CGG GAA      1315
Val Ala Val Lys Thr Phe Cys Glu Gly Ser Pro Arg Ala Gln Arg Glu
    390                 395                 400

GTC TCT TGT CTG CAA AGC AGC CGA GAG AAC AGT CAC TTG GTG ACA TTC      1363
Val Ser Cys Leu Gln Ser Ser Arg Glu Asn Ser His Leu Val Thr Phe
405                 410                 415                 420

TAT GGG AGT GAG AGC CAC AGG GGC CAC TTG TTT GTG TGT GTC ACC CTC      1411
Tyr Gly Ser Glu Ser His Arg Gly His Leu Phe Val Cys Val Thr Leu
                425                 430                 435

TGT GAG CAG ACT CTG GAA GCG TGT TTG GAT GTG CAC AGA GGG GAA GAT      1459
Cys Glu Gln Thr Leu Glu Ala Cys Leu Asp Val His Arg Gly Glu Asp
            440                 445                 450

GTG GAA AAT GAG GAA GAT GAA TTT GCC CGA AAT GTC CTG TCA TCT ATA      1507
Val Glu Asn Glu Glu Asp Glu Phe Ala Arg Asn Val Leu Ser Ser Ile
        455                 460                 465

TTT AAG GCT GTT CAA GAA CTA CAC TTG TCC TGT GGA TAC ACC CAC CAG      1555
Phe Lys Ala Val Gln Glu Leu His Leu Ser Cys Gly Tyr Thr His Gln
    470                 475                 480

GAT CTG CAA CCA CAA AAC ATC TTA ATA GAT TCT AAG AAA GCT GCT CAC      1603
Asp Leu Gln Pro Gln Asn Ile Leu Ile Asp Ser Lys Lys Ala Ala His
485                 490                 495                 500

CTG GCA GAT TTT GAT AAG AGC ATC AAG TGG GCT GGA GAT CCA CAG GAA      1651
Leu Ala Asp Phe Asp Lys Ser Ile Lys Trp Ala Gly Asp Pro Gln Glu
                505                 510                 515

GTC AAG AGA GAT CTA GAG GAC CTT GGA CGG CTG GTC CTC TAT GTG GTA      1699
Val Lys Arg Asp Leu Glu Asp Leu Gly Arg Leu Val Leu Tyr Val Val
            520                 525                 530

AAG AAG GGA AGC ATC TCA TTT GAG GAT CTG AAA GCT CAA AGT AAT GAA      1747
Lys Lys Gly Ser Ile Ser Phe Glu Asp Leu Lys Ala Gln Ser Asn Glu
        535                 540                 545

GAG GTG GTT CAA CTT TCT CCA GAT GAG GAA ACT AAG GAC CTC ATT CAT      1795
Glu Val Val Gln Leu Ser Pro Asp Glu Glu Thr Lys Asp Leu Ile His
    550                 555                 560

CGT CTC TTC CAT CCT GGG GAA CAT GTG AGG GAC TGT CTG AGT GAC CTG      1843
Arg Leu Phe His Pro Gly Glu His Val Arg Asp Cys Leu Ser Asp Leu
565                 570                 575                 580

CTG GGT CAT CCC TTC TTT TGG ACT TGG GAG AGC CGC TAT AGG ACG CTT      1891
Leu Gly His Pro Phe Phe Trp Thr Trp Glu Ser Arg Tyr Arg Thr Leu
                585                 590                 595

CGG AAT GTG GGA AAT GAA TCC GAC ATC AAA ACA CGA AAA TCT GAA AGT      1939
Arg Asn Val Gly Asn Glu Ser Asp Ile Lys Thr Arg Lys Ser Glu Ser
            600                 605                 610

GAG ATC CTC AGA CTA CTG CAA CCT GGG CCT TCT GAA CAT TCC AAA AGT      1987
Glu Ile Leu Arg Leu Leu Gln Pro Gly Pro Ser Glu His Ser Lys Ser
        615                 620                 625

TTT GAC AAG TGG ACG ACT AAG ATT AAT GAA TGT GTT ATG AAA AAA ATG      2035
Phe Asp Lys Trp Thr Thr Lys Ile Asn Glu Cys Val Met Lys Lys Met
    630                 635                 640

AAT AAG TTT TAT GAA AAA AGA GGC AAT TTC TAC CAG AAC ACT GTG GGT      2083
Asn Lys Phe Tyr Glu Lys Arg Gly Asn Phe Tyr Gln Asn Thr Val Gly
645                 650                 655                 660

GAT CTG CTA AAG TTC ATC CGG AAT TTG GGA GAA CAC ATT GAT GAA GAA      2131
Asp Leu Leu Lys Phe Ile Arg Asn Leu Gly Glu His Ile Asp Glu Glu
                665                 670                 675

AAG CAT AAA AAG ATG AAA TTA AAA ATT GGA GAC CCT TCC CTG TAT TTT      2179
Lys His Lys Lys Met Lys Leu Lys Ile Gly Asp Pro Ser Leu Tyr Phe
            680                 685                 690
```

-continued

```
CAG AAG ACA TTT CCA GAT CTG GTG ATC TAT GTC TAC ACA AAA CTA CAG       2227
Gln Lys Thr Phe Pro Asp Leu Val Ile Tyr Val Tyr Thr Lys Leu Gln
        695                     700                     705

AAC ACA GAA TAT AGA AAG CAT TTC CCC CAA ACC CAC AGT CCA AAC AAA       2275
Asn Thr Glu Tyr Arg Lys His Phe Pro Gln Thr His Ser Pro Asn Lys
    710                     715                     720

CCT CAG TGT GAT GGA GCT GGT GGG GCC AGT GGG TTG GCC AGC CCT GGG       2323
Pro Gln Cys Asp Gly Ala Gly Gly Ala Ser Gly Leu Ala Ser Pro Gly
725                     730                     735                     740

TGC TGATGGACTG ATTTGCTGGA GTTCAGGGAA CTACTTATTA GCTGTAGAGT            2376
Cys

CCTTGGCAAA TCACAACATT CTGGGCCTTT TAACTCACCA GGTTGCTTGT GAGGGATGAG     2436

TTGCATAGCT GATATGTCAG TCCCTGGCAT CGTGTATTCC ATATGTCTAT AACAAAAGCA     2496

ATATATACCC AGACTACACT AGTCCATAAG CTTTACCCAC TAACTGGGAG GACATTCTGC     2556

TAAGATTCCT TTTGTCAATT GCACCAAAAG AATGAGTGCC TTGACCCCTA ATGCTGCATA     2616

TGTTACAATT CTCTCACTTA ATTTTCCCAA TGATCTTGCA AAACAGGGAT TATCATCCCC     2676

ATTTAAGAAC TGAGGAACCT GAGACTCAGA GAGTGTGAGC TACTGGCCCA AGATTATTCA     2736

ATTTATACCT AGCACTTTAT AAATTTATGT GGTGTTATTG GTACCTCTCA TTTGGGCACC     2796

TTAAAACTTA ACTATCTTCC AGGGCTCTTC CAGATGAGGC CCAAAACATA TATAGGGGTT     2856

CCAGGAATCT CATTCATTCA TTCAGTATTT ATTGAGCATC TAGTATAAGT CTGGGCACTG     2916

GATGCATGAA TT                                                         2928
```

( 2 ) INFORMATION FOR SEQ ID NO:2:

( i ) SEQUENCE CHARACTERISTICS:
( A ) LENGTH: 741 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Glu Ser Arg Asp His Asn Asn Pro Gln Glu Gly Pro Thr Ser Ser
 1               5                  10                  15

Ser Gly Arg Arg Ala Ala Val Glu Asp Asn His Leu Leu Ile Lys Ala
            20                  25                  30

Val Gln Asn Glu Asp Val Asp Leu Val Gln Gln Leu Leu Glu Gly Gly
        35                  40                  45

Ala Asn Val Asn Phe Gln Glu Glu Glu Gly Gly Trp Thr Pro Leu His
    50                  55                  60

Asn Ala Val Gln Met Ser Arg Glu Asp Ile Val Glu Leu Leu Leu Arg
65                  70                  75                  80

His Gly Ala Asp Pro Val Leu Arg Lys Lys Asn Gly Ala Thr Leu Phe
                85                  90                  95

Ile Leu Ala Ala Ile Ala Gly Ser Val Lys Leu Leu Lys Leu Phe Leu
            100                 105                 110

Ser Lys Gly Ala Asp Val Asn Glu Cys Asp Phe Tyr Gly Phe Thr Ala
        115                 120                 125

Phe Met Glu Ala Ala Val Tyr Gly Lys Val Lys Ala Leu Lys Phe Leu
    130                 135                 140

Tyr Lys Arg Gly Ala Asn Val Asn Leu Arg Arg Lys Thr Lys Glu Asp
145                 150                 155                 160

Gln Glu Arg Leu Arg Lys Gly Gly Ala Thr Ala Leu Met Asp Ala Ala
                165                 170                 175
```

-continued

```
Glu Lys Gly His Val Glu Val Leu Lys Ile Leu Leu Asp Glu Met Gly
            180                 185                 190

Ala Asp Val Asn Ala Cys Asp Asn Met Gly Arg Asn Ala Leu Ile His
        195                 200                 205

Ala Leu Leu Ser Ser Asp Asp Ser Asp Val Glu Ala Ile Thr His Leu
    210                 215                 220

Leu Leu Asp His Gly Ala Asp Val Asn Val Arg Gly Glu Arg Gly Lys
225                 230                 235                 240

Thr Pro Leu Ile Leu Ala Val Glu Lys Lys His Leu Gly Leu Val Gln
                245                 250                 255

Arg Leu Leu Glu Gln Glu His Ile Glu Ile Asn Asp Thr Asp Ser Asp
            260                 265                 270

Gly Lys Thr Ala Leu Leu Leu Ala Val Glu Leu Lys Leu Lys Lys Ile
        275                 280                 285

Ala Glu Leu Leu Cys Lys Arg Gly Ala Ser Thr Asp Cys Gly Asp Leu
    290                 295                 300

Val Met Thr Ala Arg Arg Asn Tyr Asp His Ser Leu Val Lys Val Leu
305                 310                 315                 320

Leu Ser His Gly Ala Lys Glu Asp Phe His Pro Pro Ala Glu Asp Trp
                325                 330                 335

Lys Pro Gln Ser Ser His Trp Gly Ala Ala Leu Lys Asp Leu His Arg
            340                 345                 350

Ile Tyr Arg Pro Met Ile Gly Lys Leu Lys Phe Phe Ile Asp Glu Lys
        355                 360                 365

Tyr Lys Ile Ala Asp Thr Ser Glu Gly Gly Ile Tyr Leu Gly Phe Tyr
    370                 375                 380

Glu Lys Gln Glu Val Ala Val Lys Thr Phe Cys Glu Gly Ser Pro Arg
385                 390                 395                 400

Ala Gln Arg Glu Val Ser Cys Leu Gln Ser Ser Arg Glu Asn Ser His
                405                 410                 415

Leu Val Thr Phe Tyr Gly Ser Glu Ser His Arg Gly His Leu Phe Val
            420                 425                 430

Cys Val Thr Leu Cys Glu Gln Thr Leu Glu Ala Cys Leu Asp Val His
        435                 440                 445

Arg Gly Glu Asp Val Glu Asn Glu Glu Asp Glu Phe Ala Arg Asn Val
    450                 455                 460

Leu Ser Ser Ile Phe Lys Ala Val Gln Glu Leu His Leu Ser Cys Gly
465                 470                 475                 480

Tyr Thr His Gln Asp Leu Gln Pro Gln Asn Ile Leu Ile Asp Ser Lys
                485                 490                 495

Lys Ala Ala His Leu Ala Asp Phe Asp Lys Ser Ile Lys Trp Ala Gly
            500                 505                 510

Asp Pro Gln Glu Val Lys Arg Asp Leu Glu Asp Leu Gly Arg Leu Val
        515                 520                 525

Leu Tyr Val Val Lys Lys Gly Ser Ile Ser Phe Glu Asp Leu Lys Ala
    530                 535                 540

Gln Ser Asn Glu Glu Val Val Gln Leu Ser Pro Asp Glu Glu Thr Lys
545                 550                 555                 560

Asp Leu Ile His Arg Leu Phe His Pro Gly Glu His Val Arg Asp Cys
                565                 570                 575

Leu Ser Asp Leu Leu Gly His Pro Phe Phe Trp Thr Trp Glu Ser Arg
            580                 585                 590

Tyr Arg Thr Leu Arg Asn Val Gly Asn Glu Ser Asp Ile Lys Thr Arg
        595                 600                 605
```

```
Lys Ser Glu Ser Glu Ile Leu Arg Leu Leu Gln Pro Gly Pro Ser Glu
    610                 615                 620

His Ser Lys Ser Phe Asp Lys Trp Thr Thr Lys Ile Asn Glu Cys Val
625                 630                 635                 640

Met Lys Lys Met Asn Lys Phe Tyr Glu Lys Arg Gly Asn Phe Tyr Gln
                645                 650                 655

Asn Thr Val Gly Asp Leu Leu Lys Phe Ile Arg Asn Leu Gly Glu His
            660                 665                 670

Ile Asp Glu Glu Lys His Lys Lys Met Lys Leu Lys Ile Gly Asp Pro
        675                 680                 685

Ser Leu Tyr Phe Gln Lys Thr Phe Pro Asp Leu Val Ile Tyr Val Tyr
    690                 695                 700

Thr Lys Leu Gln Asn Thr Glu Tyr Arg Lys His Phe Pro Gln Thr His
705                 710                 715                 720

Ser Pro Asn Lys Pro Gln Cys Asp Gly Ala Gly Gly Ala Ser Gly Leu
                725                 730                 735

Ala Ser Pro Gly Cys
            740
```

( 2 ) INFORMATION FOR SEQ ID NO:3:

( i ) SEQUENCE CHARACTERISTICS:
( A ) LENGTH: 2200 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Mouse ( i x ) FEATURE:
( A ) NAME/KEY: CDS
( B ) LOCATION: 164..2200

( x i ) SEQUENCE DESCRIPTION: SEQ ID NO:3:

```
ATTCGGCACG AGGAAGGTGC CAATTACTAG CTCCCTTCTT TATTCGTGTA CTGATGAGAT     60

GTCAGAAGAC AGAACATAAT CAGCCCAATC CCTACTCCAA GACTCTCATT GTGTCCCAAA    120

GAAACACACG TGTGCATTTC CCAAGGAAAA GGCATTGAGG ACC ATG GAG ACC CCG     175
                                                Met Glu Thr Pro
                                                  1

GAT TAT AAC ACA CCT CAG GGT GGA ACC CCA TCA GCG GGA AGT CAG AGG     223
Asp Tyr Asn Thr Pro Gln Gly Gly Thr Pro Ser Ala Gly Ser Gln Arg
  5                  10                  15                  20

ACC GTT GTC GAA GAT GAT TCT TCG TTG ATC AAA GCT GTT CAG AAG GGA     271
Thr Val Val Glu Asp Asp Ser Ser Leu Ile Lys Ala Val Gln Lys Gly
                 25                  30                  35

GAT GTT GTC AGG GTC CAG CAA TTG TTA GAA AAA GGG GCT GAT GCC AAT     319
Asp Val Val Arg Val Gln Gln Leu Leu Glu Lys Gly Ala Asp Ala Asn
             40                  45                  50

GCC TGT GAA GAC ACC TGG GGC TGG ACA CCT TTG CAC AAC GCA GTG CAA     367
Ala Cys Glu Asp Thr Trp Gly Trp Thr Pro Leu His Asn Ala Val Gln
         55                  60                  65

GCT GGC AGG GTA GAC ATT GTG AAC CTC CTG CTT AGT CAT GGT GCT GAC     415
Ala Gly Arg Val Asp Ile Val Asn Leu Leu Leu Ser His Gly Ala Asp
     70                  75                  80

CCT CAT CGG AGG AAG AAG AAT GGG GCC ACC CCC TTC ATC ATT GCT GGG     463
Pro His Arg Arg Lys Lys Asn Gly Ala Thr Pro Phe Ile Ile Ala Gly
 85                  90                  95                 100
```

-continued

```
ATC CAG GGA GAT GTG AAA CTG CTC GAG ATT CTC CTC TCT TGT GGT GCA       511
Ile Gln Gly Asp Val Lys Leu Leu Glu Ile Leu Leu Ser Cys Gly Ala
                105                 110                 115

GAC GTC AAT GAG TGT GAC GAG AAC GGA TTC ACG GCT TTC ATG GAA GCT       559
Asp Val Asn Glu Cys Asp Glu Asn Gly Phe Thr Ala Phe Met Glu Ala
            120                 125                 130

GCT GAG CGT GGT AAC GCT GAA GCC TTA AGA TTC CTT TTT GCT AAG GGA       607
Ala Glu Arg Gly Asn Ala Glu Ala Leu Arg Phe Leu Phe Ala Lys Gly
        135                 140                 145

GCC AAT GTG AAT TTG CGA CGA CAG ACA ACG AAG GAC AAA AGG CGA TTG       655
Ala Asn Val Asn Leu Arg Arg Gln Thr Thr Lys Asp Lys Arg Arg Leu
    150                 155                 160

AAG CAA GGA GGC GCC ACA GCT CTC ATG AGC GCT GCT GAG AAG GGC CAC       703
Lys Gln Gly Gly Ala Thr Ala Leu Met Ser Ala Ala Glu Lys Gly His
165                 170                 175                 180

CTG GAA GTC CTG AGA ATT CTC CTC AAT GAC ATG AAG GCA GAA GTC GAT       751
Leu Glu Val Leu Arg Ile Leu Leu Asn Asp Met Lys Ala Glu Val Asp
                185                 190                 195

GCT CGG GAC AAC ATG GGC AGA AAT GCC CTG ATC CGT ACT CTG CTG AAC       799
Ala Arg Asp Asn Met Gly Arg Asn Ala Leu Ile Arg Thr Leu Leu Asn
            200                 205                 210

TGG GAT TGT GAA AAT GTG GAG GAG ATT ACT TCA ATC CTG ATT CAG CAC       847
Trp Asp Cys Glu Asn Val Glu Glu Ile Thr Ser Ile Leu Ile Gln His
        215                 220                 225

GGG GCT GAT GTT AAC GTG AGA GGA GAA AGA GGG AAA ACA CCC CTC ATC       895
Gly Ala Asp Val Asn Val Arg Gly Glu Arg Gly Lys Thr Pro Leu Ile
    230                 235                 240

GCA GCA GTG GAG AGG AAG CAC ACA GGC TTG GTG CAG ATG CTC CTG AGT       943
Ala Ala Val Glu Arg Lys His Thr Gly Leu Val Gln Met Leu Leu Ser
245                 250                 255                 260

CGG GAA GGC ATA AAC ATA GAT GCC AGG GAT AAC GAG GGC AAG ACA GCT       991
Arg Glu Gly Ile Asn Ile Asp Ala Arg Asp Asn Glu Gly Lys Thr Ala
                265                 270                 275

CTG CTA ATT GCT GTT GAT AAA CAA CTG AAG GAA ATT GTC CAG TTG CTT      1039
Leu Leu Ile Ala Val Asp Lys Gln Leu Lys Glu Ile Val Gln Leu Leu
            280                 285                 290

CTT GAA AAG GGA GCT GAT AAG TGT GAC GAT CTT GTT TGG ATA GCC AGG      1087
Leu Glu Lys Gly Ala Asp Lys Cys Asp Asp Leu Val Trp Ile Ala Arg
        295                 300                 305

AGG AAT CAT GAC TAT CAC CTT GTA AAG CTT CTC CTC CCT TAT GTA GCT      1135
Arg Asn His Asp Tyr His Leu Val Lys Leu Leu Leu Pro Tyr Val Ala
    310                 315                 320

AAT CCT GAC ACC GAC CCT CCT GCT GGA GAC TGG TCG CCT CAC AGT TCA      1183
Asn Pro Asp Thr Asp Pro Pro Ala Gly Asp Trp Ser Pro His Ser Ser
325                 330                 335                 340

CGT TGG GGG ACA GCC TTG AAA AGC CTC CAC AGT ATG ACT CGA CCC ATG      1231
Arg Trp Gly Thr Ala Leu Lys Ser Leu His Ser Met Thr Arg Pro Met
                345                 350                 355

ATT GGC AAA CTC AAG ATC TTC ATT CAT GAT GAC TAT AAA ATT GCT GGC      1279
Ile Gly Lys Leu Lys Ile Phe Ile His Asp Asp Tyr Lys Ile Ala Gly
            360                 365                 370

ACT TCC GAA GGG GCT GTC TAC CTA GGG ATC TAT GAC AAT CGA GAA GTG      1327
Thr Ser Glu Gly Ala Val Tyr Leu Gly Ile Tyr Asp Asn Arg Glu Val
        375                 380                 385

GCT GTG AAG GTC TTC CGT GAG AAT AGC CCA CGT GGA TGT AAG GAA GTC      1375
Ala Val Lys Val Phe Arg Glu Asn Ser Pro Arg Gly Cys Lys Glu Val
    390                 395                 400

TCT TGT CTG CGG GAC TGC GGT GAC CAC AGT AAC TTA GTG GCT TTC TAT      1423
Ser Cys Leu Arg Asp Cys Gly Asp His Ser Asn Leu Val Ala Phe Tyr
405                 410                 415                 420
```

-continued

```
GGA AGA GAG GAC GAT AAG GGC TGT TTA TAT GTG TGT GTG TCC CTG TGT     1471
Gly Arg Glu Asp Asp Lys Gly Cys Leu Tyr Val Cys Val Ser Leu Cys
                425                 430                 435

GAG TGG ACA CTG GAA GAG TTC CTG AGG TTG CCC AGA GAG GAA CCT GTG     1519
Glu Trp Thr Leu Glu Glu Phe Leu Arg Leu Pro Arg Glu Glu Pro Val
            440                 445                 450

GAG AAC GGG GAA GAT AAG TTT GCC CAC AGC ATC CTA TTA TCT ATA TTT     1567
Glu Asn Gly Glu Asp Lys Phe Ala His Ser Ile Leu Leu Ser Ile Phe
        455                 460                 465

GAG GGT GTT CAA AAA CTA CAC TTG CAT GGA TAT TCC CAT CAG GAC CTG     1615
Glu Gly Val Gln Lys Leu His Leu His Gly Tyr Ser His Gln Asp Leu
    470                 475                 480

CAA CCA CAA AAC ATC TTA ATA GAT TCC AAG AAA GCT GTC CGG CTG GCA     1663
Gln Pro Gln Asn Ile Leu Ile Asp Ser Lys Lys Ala Val Arg Leu Ala
485                 490                 495                 500

GAT TTT GAT CAG AGC ATC CGA TGG ATG GGA GAG TCA CAG ATG GTC AGG     1711
Asp Phe Asp Gln Ser Ile Arg Trp Met Gly Glu Ser Gln Met Val Arg
                505                 510                 515

AGA GAC TTG GAG GAT CTT GGA CGG CTG GTT CTC TAC GTG GTA ATG AAA     1759
Arg Asp Leu Glu Asp Leu Gly Arg Leu Val Leu Tyr Val Val Met Lys
            520                 525                 530

GGT GAG ATC CCC TTT GAG ACA CTA AAG ACT CAG AAT GAT GAA GTG CTG     1807
Gly Glu Ile Pro Phe Glu Thr Leu Lys Thr Gln Asn Asp Glu Val Leu
        535                 540                 545

CTT ACA ATG TCT CCA GAT GAG GAG ACT AAG GAC CTC ATT CAT TGC CTG     1855
Leu Thr Met Ser Pro Asp Glu Glu Thr Lys Asp Leu Ile His Cys Leu
    550                 555                 560

TTT TCT CCT GGA GAA AAT GTC AAG AAC TGC CTG GTA GAC CTG CTT GGC     1903
Phe Ser Pro Gly Glu Asn Val Lys Asn Cys Leu Val Asp Leu Leu Gly
565                 570                 575                 580

CAT CCT TTC TTT TGG ACT TGG GAG AAC CGC TAT AGA ACA CTC CGG AAT     1951
His Pro Phe Phe Trp Thr Trp Glu Asn Arg Tyr Arg Thr Leu Arg Asn
                585                 590                 595

GTG GGA AAT GAA TCT GAC ATC AAA GTA CGG AAA TGT AAA AGT GAT CTT     1999
Val Gly Asn Glu Ser Asp Ile Lys Val Arg Lys Cys Lys Ser Asp Leu
            600                 605                 610

CTC AGA CTA CTG CAG CAT CAG ACA CTT GAG CCT CCC AGA AGC TTT GAC     2047
Leu Arg Leu Leu Gln His Gln Thr Leu Glu Pro Pro Arg Ser Phe Asp
        615                 620                 625

CAG TGG ACA TCT AAG ATC GAC AAA AAT GTT ATG GAT GAA ATG AAT CAT     2095
Gln Trp Thr Ser Lys Ile Asp Lys Asn Val Met Asp Glu Met Asn His
    630                 635                 640

TTC TAC GAA AAG AGA AAA AAA AAC CCT TAT CAG GAT ACT GTA GGT GAT     2143
Phe Tyr Glu Lys Arg Lys Lys Asn Pro Tyr Gln Asp Thr Val Gly Asp
645                 650                 655                 660

CTG CTG AAG TTT ATT CGG AAT ATA GGC GAA CAC ATC AAT GAG GAA AAA     2191
Leu Leu Lys Phe Ile Arg Asn Ile Gly Glu His Ile Asn Glu Glu Lys
                665                 670                 675

AAG CGG GGG                                                         2200
Lys Arg Gly
```

( 2 ) INFORMATION FOR SEQ ID NO:4:

( i ) SEQUENCE CHARACTERISTICS:
( A ) LENGTH: 679 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Glu Thr Pro Asp Tyr Asn Thr Pro Gln Gly Gly Thr Pro Ser Ala
```

-continued 1 5 10 15

Gly Ser Gln Arg Thr Val Val Glu Asp Asp Ser Ser Leu Ile Lys Ala
20 25 30

Val Gln Lys Gly Asp Val Val Arg Val Gln Gln Leu Leu Glu Lys Gly
35 40 45

Ala Asp Ala Asn Ala Cys Glu Asp Thr Trp Gly Trp Thr Pro Leu His
50 55 60

Asn Ala Val Gln Ala Gly Arg Val Asp Ile Val Asn Leu Leu Leu Ser
65 70 75 80

His Gly Ala Asp Pro His Arg Arg Lys Lys Asn Gly Ala Thr Pro Phe
85 90 95

Ile Ile Ala Gly Ile Gln Gly Asp Val Lys Leu Leu Glu Ile Leu Leu
100 105 110

Ser Cys Gly Ala Asp Val Asn Glu Cys Asp Glu Asn Gly Phe Thr Ala
115 120 125

Phe Met Glu Ala Ala Glu Arg Gly Asn Ala Glu Ala Leu Arg Phe Leu
130 135 140

Phe Ala Lys Gly Ala Asn Val Asn Leu Arg Arg Gln Thr Thr Lys Asp
145 150 155 160

Lys Arg Arg Leu Lys Gln Gly Gly Ala Thr Ala Leu Met Ser Ala Ala
165 170 175

Glu Lys Gly His Leu Glu Val Leu Arg Ile Leu Leu Asn Asp Met Lys
180 185 190

Ala Glu Val Asp Ala Arg Asp Asn Met Gly Arg Asn Ala Leu Ile Arg
195 200 205

Thr Leu Leu Asn Trp Asp Cys Glu Asn Val Glu Glu Ile Thr Ser Ile
210 215 220

Leu Ile Gln His Gly Ala Asp Val Asn Val Arg Gly Glu Arg Gly Lys
225 230 235 240

Thr Pro Leu Ile Ala Ala Val Glu Arg Lys His Thr Gly Leu Val Gln
245 250 255

Met Leu Leu Ser Arg Glu Gly Ile Asn Ile Asp Ala Arg Asp Asn Glu
260 265 270

Gly Lys Thr Ala Leu Leu Ile Ala Val Asp Lys Gln Leu Lys Glu Ile
275 280 285

Val Gln Leu Leu Leu Glu Lys Gly Ala Asp Lys Cys Asp Asp Leu Val
290 295 300

Trp Ile Ala Arg Arg Asn His Asp Tyr His Leu Val Lys Leu Leu Leu
305 310 315 320

Pro Tyr Val Ala Asn Pro Asp Thr Asp Pro Pro Ala Gly Asp Trp Ser
325 330 335

Pro His Ser Ser Arg Trp Gly Thr Ala Leu Lys Ser Leu His Ser Met
340 345 350

Thr Arg Pro Met Ile Gly Lys Leu Lys Ile Phe Ile His Asp Asp Tyr
355 360 365

Lys Ile Ala Gly Thr Ser Glu Gly Ala Val Tyr Leu Gly Ile Tyr Asp
370 375 380

Asn Arg Glu Val Ala Val Lys Val Phe Arg Glu Asn Ser Pro Arg Gly
385 390 395 400

Cys Lys Glu Val Ser Cys Leu Arg Asp Cys Gly Asp His Ser Asn Leu
405 410 415

Val Ala Phe Tyr Gly Arg Glu Asp Asp Lys Gly Cys Leu Tyr Val Cys
420 425 430

Val Ser Leu Cys Glu Trp Thr Leu Glu Glu Phe Leu Arg Leu Pro Arg
435 440 445

Glu Glu Pro Val Glu Asn Gly Glu Asp Lys Phe Ala His Ser Ile Leu
450 455 460

Leu Ser Ile Phe Glu Gly Val Gln Lys Leu His Leu His Gly Tyr Ser
465 470 475 480

His Gln Asp Leu Gln Pro Gln Asn Ile Leu Ile Asp Ser Lys Lys Ala
485 490 495

Val Arg Leu Ala Asp Phe Asp Gln Ser Ile Arg Trp Met Gly Glu Ser
500 505 510

Gln Met Val Arg Arg Asp Leu Glu Asp Leu Gly Arg Leu Val Leu Tyr
515 520 525

Val Val Met Lys Gly Glu Ile Pro Phe Glu Thr Leu Lys Thr Gln Asn
530 535 540

Asp Glu Val Leu Leu Thr Met Ser Pro Asp Glu Glu Thr Lys Asp Leu
545 550 555 560

Ile His Cys Leu Phe Ser Pro Gly Glu Asn Val Lys Asn Cys Leu Val
565 570 575

Asp Leu Leu Gly His Pro Phe Phe Trp Thr Trp Glu Asn Arg Tyr Arg
580 585 590

Thr Leu Arg Asn Val Gly Asn Glu Ser Asp Ile Lys Val Arg Lys Cys
595 600 605

Lys Ser Asp Leu Leu Arg Leu Leu Gln His Gln Thr Leu Glu Pro Pro
610 615 620

Arg Ser Phe Asp Gln Trp Thr Ser Lys Ile Asp Lys Asn Val Met Asp
625 630 635 640

Glu Met Asn His Phe Tyr Glu Lys Arg Lys Lys Asn Pro Tyr Gln Asp
645 650 655

Thr Val Gly Asp Leu Leu Lys Phe Ile Arg Asn Ile Gly Glu His Ile
660 665 670

Asn Glu Glu Lys Lys Arg Gly
675

( 2 ) INFORMATION FOR SEQ ID NO:5:

( i ) SEQUENCE CHARACTERISTICS:
( A ) LENGTH: 190 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( v i ) ORIGINAL SOURCE:
( A ) ORGANISM: E. coli ( x i ) SEQUENCE DESCRIPTION: SEQ ID NO:5:

Asp Arg Arg Lys Pro Arg Gln Asn Asn Arg Arg Asp Arg Asn Glu Arg
1 5 10 15

Arg Asp Thr Arg Ser Glu Arg Thr Glu Gly Ser Asp Asn Arg Glu Glu
20 25 30

Asn Arg Arg Asn Arg Arg Gln Ala Gln Gln Gln Thr Ala Glu Thr Arg
35 40 45

Glu Ser Arg Gln Gln Ala Glu Val Thr Glu Lys Ala Arg Thr Ala Asp
50 55 60

Glu Gln Gln Ala Pro Arg Arg Glu Arg Ser Arg Arg Arg Asn Asp Asp
65 70 75 80

Lys Arg Gln Ala Gln Gln Glu Ala Lys Ala Leu Asn Val Glu Glu Gln
85 90 95

Ser Val Gln Glu Thr Glu Gln Glu Glu Arg Val Arg Pro Val Gln Pro
100 105 110

Arg Arg Lys Gln Arg Gln Leu Asn Gln Lys Val Arg Tyr Glu Gln Ser
115 120 125

Val Ala Glu Glu Ala Val Val Ala Pro Val Val Glu Glu Thr Val Ala
130 135 140

Ala Glu Pro Ile Val Gln Glu Ala Pro Ala Pro Arg Thr Glu Leu Val
145 150 155 160

Lys Val Pro Leu Pro Val Val Ala Gln Thr Ala Pro Glu Gln Gln Glu
165 170 175

Glu Asn Asn Ala Asp Asn Arg Asp Asn Gly Gly Met Pro Ser
180 185 190

( 2 ) INFORMATION FOR SEQ ID NO:6:

( i ) SEQUENCE CHARACTERISTICS:
( A ) LENGTH: 33 amino acids
( B ) TYPE: amino acid
( C ) STRANDEDNESS:
( D ) TOPOLOGY: linear ( i i ) MOLECULE TYPE: peptide ( v ) FRAGMENT TYPE: internal ( i x ) FEATURE:
( A ) NAME/KEY: Modified-site
( B ) LOCATION: 4
( D ) OTHER INFORMATION: /note= "Xaa at residue 4 is Thr or Ser"

( i x ) FEATURE:
( A ) NAME/KEY: Modified-site
( B ) LOCATION: 5
( D ) OTHER INFORMATION: /note= "Xaa at residue 5 is Pro or Ala"

( i x ) FEATURE:
( A ) NAME/KEY: Modified-site
( B ) LOCATION: 8..17
( D ) OTHER INFORMATION: /note= "Xaa at residues 8 and 17 is a hydrophobic amino acid"

( i x ) FEATURE:
( A ) NAME/KEY: Modified-site
( B ) LOCATION: 18
( D ) OTHER INFORMATION: /note= "Xaa at residue 18 is Val or Ala"

( i x ) FEATURE:
( A ) NAME/KEY: Modified-site
( B ) LOCATION: 29
( D ) OTHER INFORMATION: /note= "Xaa at residue 29 is Asp or Asn"

( x i ) SEQUENCE DESCRIPTION: SEQ ID NO:6:

Xaa Gly Xaa Xaa Xaa Leu His Xaa Ala Ala Xaa Xaa Gly His Xaa Xaa
1 5 10 15

Xaa Xaa Xaa Xaa Leu Leu Xaa Xaa Gly Ala Xaa Xaa Xaa Xaa Xaa Xaa
20 25 30

Xaa ( 2 ) INFORMATION FOR SEQ ID NO:7:

( i ) SEQUENCE CHARACTERISTICS:
( A ) LENGTH: 36 amino acids ( B ) TYPE: amino acid
( C ) STRANDEDNESS:
( D ) TOPOLOGY: linear ( i i ) MOLECULE TYPE: peptide ( v ) FRAGMENT TYPE: internal ( x i ) SEQUENCE DESCRIPTION: SEQ ID NO:7:

```
Cys Xaa Xaa Xaa Xaa Cys Xaa Xaa Xaa Cys Xaa Xaa Xaa Xaa Xaa Xaa
1               5                   10                  15

Xaa Xaa Xaa Xaa Xaa Xaa Xaa Xaa Xaa Xaa Xaa Cys Xaa Xaa Xaa Cys
            20                  25                  30

Xaa Xaa Xaa Cys
        35
```

( 2 ) INFORMATION FOR SEQ ID NO:8:

( i ) SEQUENCE CHARACTERISTICS:
( A ) LENGTH: 50 amino acids
( B ) TYPE: amino acid
( C ) STRANDEDNESS:
( D ) TOPOLOGY: linear ( i i ) MOLECULE TYPE: peptide ( v ) FRAGMENT TYPE: internal ( x i ) SEQUENCE DESCRIPTION: SEQ ID NO:8:

```
Cys Xaa Xaa Xaa Xaa Xaa Xaa Xaa Xaa Xaa Xaa Xaa Cys Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Cys Xaa Xaa Xaa Cys Xaa Xaa Xaa Xaa Xaa
        35                  40                  45

Xaa Cys
    50
```